US007037722B1

(12) United States Patent
Hein et al.

(10) Patent No.: US 7,037,722 B1
(45) Date of Patent: *May 2, 2006

(54) TRANSGENIC PLANTS EXPRESSING ASSEMBLED SECRETORY ANTIBODIES

(75) Inventors: Mich B. Hein, Fallbrook, CA (US); Andrew Hiatt, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 09/512,568

(22) Filed: Feb. 24, 2000

Related U.S. Application Data

(63) Continuation of application No. 09/199,534, filed on Nov. 25, 1998, now Pat. No. 6,417,429, which is a continuation of application No. 08/642,406, filed on May 3, 1996, now Pat. No. 5,959,177, which is a continuation-in-part of application No. 07/971,951, filed on Nov. 5, 1992, now Pat. No. 5,639,947, which is a continuation of application No. 07/591,823, filed on Oct. 2, 1990, now Pat. No. 5,202,422, which is a continuation-in-part of application No. 07/427,765, filed on Oct. 27, 1989, now abandoned.

(51) Int. Cl.
*C12N 15/82* (2006.01)
*C12N 15/13* (2006.01)
*A01H 5/00* (2006.01)
*A01H 13/00* (2006.01)

(52) U.S. Cl. .................. 435/419; 530/387.1; 536/23.53; 800/296; 800/298; 800/317.3

(58) Field of Classification Search ............. 424/130.1, 424/141.1; 435/183, 410, 419, 320.1; 514/44; 530/350, 387.1; 536/23.53, 24.1; 800/278, 800/288, 295, 296, 298, 317.3
See application file for complete search history.

(56) References Cited

U.S. PATENT DOCUMENTS

| 4,762,785 | A | 8/1988 | Comai |
| 4,771,002 | A | 9/1988 | Gelvin |
| 4,816,397 | A | 3/1989 | Bois et al. |
| 4,816,567 | A | 3/1989 | Cabilly et al. |
| 4,956,282 | A | 9/1990 | Goodman et al. |
| 6,417,429 | B1 * | 7/2002 | Hein et al. .................. 800/288 |

FOREIGN PATENT DOCUMENTS

| WO | WO87/00865 | 2/1987 |
| WO | WO88/04936 | 7/1988 |

OTHER PUBLICATIONS

Bonifacino et al. Pre-Golgi degradation of newly synthesized T-cell antigen chains: intrinsic sensitivity and the role of subunit assembly. J Cell Biol. Jul. 1989;109(1):73-83.*
Lippincott-Schwartz et al. Degradation from the endoplasmic reticulum: disposing of newly synthesized proteins. Cell. Jul. 15, 1988;54(2):209-20.*
Waldmann et al. Molecular cloning and functional expression of a novel amiloride-sensitive Na+ channel. J Biol Chem. 1995 N 17;270(46):27411-4.*
Yu et al. Biosynthesis of the phagocyte NADPH oxidase cytochrome b558. Role of heme incorporation and heterodimer formation in maturation and stability of gp91phox and p22phox subunits. J Biol Chem. Oct. 24, 1997;272(43):27288-94.*
U.S. Appl. No. 09/491,322, filed Jan. 2000, Hein et al.*
U.S. Appl. No. 10/372,614, filed Feb. 2003, Hein et al.*
Hiatt, et al., "Production of Antibodies in Transgenic Plants", *Nature*, 342:76-78 (1989).
Horsch, et al., "A Simple and General Method for Transferring Genes into Plants", *Science*, 227:1229-1231 (1985).
Hunt, et al., "Plant Cells Do Not Properly Recognize Animal Gene Polyadenylation Signals", *Plant Molecular Biology*, 8:23-35 (1987).
Lefebvre, et al., "Mammalian Metallothionein Functions in Plants", *Biotechnology*, 5:1053-1056 (1987).
Lutcke, et al., "Selection of AUG Initiation Codons Differs in Plants and Animals", *Embo Journal*, 6(1):43-48 (1987).
Ma, et al., "Assembly of Monoclonal Antibodies with IgG1 and IgA Heavy Chain Domains in Transgenic Tobacco Plants", *Eur. J. Immunol.*, 24:131-138 (1994).
Mach, Jean-Pierre, "In Vitro Combination of Human Bovine Free Secretory Component with IgA of Various Species", *Nature*, 228:1278-1282 (1970).
Pautot, et al., "Expression of a Mouse Metallothionein Gene in Transgenic Plant Tissues", *Gene*, 77:133-140 (1989).
Poehlman, John M., Breeding Field Crops; AVI Publishing Co. Inc., Chapter 3: Gene Recombination in Plant Breeding pp. 38-63 (1986).
Thiele, et al, "Mammalian Metallothionein is Function in Yeast", *Science*, 231:854-856 (1986).
Thorens and Vassalli, "Chloroquine and Ammonium Chloride Prevent Terminal Glycosylation of Immunoglobulins in Plasma Cells without Affecting Secretion", *Nature*, 321:618-620 (1986).
Vandekerckhove, et al, "Enkephalins Produced in Transgenic Plants Using Modified 2S Seed Storage Proteins", *Biotechnology*, 7:929-932 (1989).

(Continued)

Primary Examiner—Cynthia Collins
(74) Attorney, Agent, or Firm—Foley & Lardner LLP

(57) ABSTRACT

The present invention relates to expression and assembly of foreign multimeric proteins—e.g., antibodies—in plants, as well as to transgenic plants that express such proteins. In one of several preferred embodiments, the generation and assembly of functional secretory antibodies in plants is disclosed. The invention also discloses compositions produced by the transgenic plants of the present invention and methods of using same.

31 Claims, 8 Drawing Sheets

OTHER PUBLICATIONS von Heijne, Gunnar, "Signal Sequences: The Limits of Variation", *J. Mol. Biol.*, 184:99-105 (1985).

Azipura, et al., "Oral Vaccination: Identification of Classes of Proteins that Provoke an Immune Response upon Oral Feeding", *J Exp. Med.*, 167:440-451 (1988).

Carayannopoulos, et al., "Recombinant Human IgA Expressed in Insect Cells", *Proc. Natl. Acad. Sci., USA*, 91;8348-8352 (1994).

Chrisppels, Maarten J., "Sorting of Proteins in the Secretory System", *Annu. Rev. Plant Physiol. Plant Mol. Biol.*, 42:21-53 (1991).

Cocking, et al., "Gene Transfer in Cereals", *Science*, 236:1259-1262 (1987).

During, (Jul. 9, 1988), Wundinduzier bare Expression und Sekretion von T4 Lysozym and monoklonalen Antikorpern in Nicotiana Tabacum. Dissertation, University of Koln, FRG. pp. 13-16, 65-78, 87-89, 103-105, 108-110, 112-118, 120-126, and 135-158. Also, English translation.

During, et al., "Synthesis and Self-Assembly of a Functional Monoclonal Antibody in Transgenic Nicotiana Tabacum", *Plant Molecular Biology*, 15:281-293 (1990).

During and Hippe, "Synthesis, Assembly and Targeting of Foreign Chimeric Proteins in Transgenic Nicotiana Tabacum Cells", *Biol. Chem. Hoppe Seyler, Gesellschaft fur biologische Chemie*, 370:888 (1989).

Edelman, et al., "The Covalent Structure of an Entire γG1 Immunoglobulin Molecule", *Proc. Natl. Acad. Sci., USA*, 63:78-85 (1969).

Eicholtz, et al., "Expression of Mouse Dihydrofolate Reductase Gene Confers Methotrexate Resistance in Transgenic Petunia Plants", *Somatic Cell and Molecular Genetics*, 13(1):67-76 (1987).

Graves and Goldman, "The Transformation of Zea mays Seedlings with Agrobacterium Tumefaciens Detection of T-DNA Specific Enzyme Activities", *Plant Molecular Biology*, 7:43-50 (1986).

Hein, et al., "Evaluation of Immunoglobulins from Plant Cells", *Biotechnol. Prog.*, 7:455-461 (1991).

Beachy, et al., "Accumulation and assembly of soybean β-conglycinin in seeds of transformed petunia plants," *EMBO J.*, 4:3047-3053 (1985).

Jefferson, et al., "GUS fusions: β-glucuronidase as a sensitive and versatile gene fusion marker in higher plants," *EMBO Journal*, 6(13):3901-3907 (1987).

Harpster, et al., "Relative strengths of the 35S cauliflower mosaic virus, 1', 2', and nopaline synthase promoters in transformed tobacco sugarbeet and oilseed rape callus tissue," *Mol. Gen. Genet*, 212:182-190 (1988).

Kavanaugh, et al., "Targeting a foreign protein to chloroplasts using fusions to the transit peptide of a chlorophyll a/b protein," *Mol. Gen Genet*, 215:38-45 (1988).

Iturriaga, et al., "Endoplasmic Reticulum Targeting and Glycosylation of Hybrid Proteins in Transgenic Tobacco," *The Plant Cell*, 1:381-390 (1989).

Hofte & Whiteley, "Insecticidal Crystal Proteins of *Bacillus thuringiensis*," *Microbiological Reviews*, 53(2):242-255 (1989).

Kusnadi, et al., "Production of Recombinant Proteins in Transgenic Plants: Practical Considerations," *Biotechnology and Bioengineering*, 56(5):473-484 (1997).

* cited by examiner

HYBRID

HIGH MANNOSE

```
                          SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

CCTTGACCGT AAGACATG                                              18

(2) INFORMATION FOR SEQ ID NO: 2:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

AATTCATGTC TTACGGTCAA GG                                         22

(2) INFORMATION FOR SEQ ID NO: 3:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

TGTGAAAACC ATATTGAATT CCACCAATAC AAA                             33
```

```
(2) INFORMATION FOR SEQ ID NO: 4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

ATTTAGCACA ACATCCATGT CGACGAATTC AATCCAAAAA AGCAT                45

(2) INFORMATION FOR SEQ ID NO: 5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 5:

GGGGAGCTGG TGGTGGAATT CGTCGACCTT TGTCTCTAAC AC                   42

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 6:

CCATCCCATG GTTGAATTCA GTGTCGTCAG                                 30

(2) INFORMATION FOR SEQ ID NO: 7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

CTGCAACTGG ACCTGCATGT CGACGAATTC AGCTCCTGAC AGGAG                45
```

```
(2) INFORMATION FOR SEQ ID NO: 8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

CCTGTAGGAC CAGAGGAATT CGTCGACACT GGGATTATTT AC                     42

(2) INFORMATION FOR SEQ ID NO: 9:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

GAATTCATTC AAGAATAGTT CAAACAAGAA GATTACAAAC TATCAATTTC ATACACAATA    60

TAAACGATTA AAAGA                                                    75

(2) INFORMATION FOR SEQ ID NO: 10:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO: 10:

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Leu Lys Arg Asp Val Val Leu
                85                  90
```

-continued (2) INFORMATION FOR SEQ ID NO: 11:

(i) SEQUENCE CHARACTERISTICS:
        (A) LENGTH: 90 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO: 11:

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Leu Lys Arg Glu Val Glu Leu
            85                  90
```

(2) INFORMATION FOR SEQ ID NO: 12:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (xi) SEQUENCE DESCRIPTION: SEQ ID NO: 12:

```
Met Glu Leu Asp Leu Ser Leu Pro Leu Ser Gly Ala Ala Gly Gly Thr
1               5                   10                  15
```

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 13:

ACCAGATCTA TGGAATGGAC CTGGGTTTTT C                          31

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
    (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

CCCAAGCTTG GTTTTGGAGA TGGTTTTCTC                                  30

(2) INFORMATION FOR SEQ ID NO: 15:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 15:

GATAAGCTTG GTCCTACTCC TCCTCCTCCT A                                31

(2) INFORMATION FOR SEQ ID NO: 16:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 16:

AATCTCGAGT CAGTAGCAGA TGCCATCTCC                                  30

(2) INFORMATION FOR SEQ ID NO: 17:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

GGAAAGCTTT GTACATATGC AAGGCTTACA                                  30

(2) INFORMATION FOR SEQ ID NO: 18:

(i) SEQUENCE CHARACTERISTICS:
         (A) LENGTH: 23 base pairs
         (B) TYPE: nucleic acid
         (C) STRANDEDNESS: single
         (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO: 18:

GATCTATGGC TCTCTTCTTG CTC                                              23

(2) INFORMATION FOR SEQ ID NO: 19:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 19:

AATTCTTATT CCGCACTCTG CACTGC                                           26

(2) INFORMATION FOR SEQ ID NO: 20:

(i) SEQUENCE CHARACTERISTICS:
            (A) LENGTH: 3517 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 20:

GGCCGGGGTT ACGGGCTGGC CAGCAGGCTG TGCCCCCGAG TCCGGTCAGC AGGAGGGGAA         60

GAAGTGGCCT AAAATCTCTC CCGCATCGGC AGCCCAGGCC TAGTGCCCTA CCAGCCACCA        120

GCCATGGCTC TCTTCTTGCT CACCTGCCTG CTGGCTGTCT TTTCAGCGGC CACGGCACAA        180

AGCTCCTTAT TGGGTCCCAG CTCCATATTT GGTCCCGGGG AGGTGAATGT TTTGGAAGGC        240

GACTCGGTGT CCATCACATG CTACTACCCA ACAACCTCCG TCACCCGGCA CAGCCGGAAG        300

TTCTGGTGCC GGGAAGAGGA GAGCGGCCGC TGCGTGACGC TTGCCTCGAC CGGCTACACG        360

TCCCAGGAAT ACTCCGGGAG AGGCAAGCTC ACCGACTTCC CTGATAAAGG GGAGTTTGTG        420

GTGACTGTTG ACCAACTCAC CCAGAACGAC TCAGGGAGCT ACAAGTGTGG CGTGGGAGTC        480

AACGGCCGTG GCCTGGACTT CGGTGTCAAC GTGCTGGTCA GCCAGAAGCC AGAGCCTGAT        540

GACGTTGTTT ACAAACAATA TGAGAGTTAT ACAGTAACCA TCACCTGCCC TTTCACATAT        600

GCGACTAGGC AACTAAAGAA GTCCTTTTAC AAGGTGGAAG ACGGGAACT TGTACTCATC         660

ATTGATTCCA GCAGTAAGGA GGCAAAGGAC CCCAGGTATA AGGCAGAAT AACGTTGCAG         720

ATCCAAAGTA CCACAGCAAA AGAATTCACA GTCACCATCA AGCATTTGCA GCTCAATGAT        780

GCTGGGCAGT ATGTCTGCCA GAGTGGAAGC GACCCCACTG CTGAAGAACA GAACGTTGAC        840

CTCCGACTGC TAACTCCTGG TCTGCTCTAT GGAAACCTGG GGGCTCGGT GACCTTTGAA         900

TGTGCCCTGG ACTCTGAAGA CGCAAACGCG GTAGCATCCT TGCGCCAGGT TAGGGGTGGC        960

AATGTGGTCA TTGACAGCCA GGGGACAATA GATCCAGCCT TCGAGGGCAG GATCCTGTTC       1020

```
ACCAAGGCTG AGAACGGCCA CTTCAGTGTA GTGATCGCAG GCCTGAGGAA GGAAGACACA     1080

GGGAACTATC TGTGCGGAGT CCAGTCCAAT GGTCAGTCTG GGGATGGGCC CACCCAGCTT     1140

CGGCAACTCT TCGTCAATGA AGAGATCGAC GTGTCCCGCA GCCCCCCTGT GTTGAAGGGC     1200

TTTCCAGGAG GCTCCGTGAC CATACGCTGC CCCTACAACC CGAAGAGAAG CGACAGCCAC     1260

CTGCAGCTGT ATCTCTGGGA AGGGAGTCAA ACCCGCCATC TGCTGGTGGA CAGCGGCGAG     1320

GGGCTGGTTC AGAAAGACTA CACAGGCAGG CTGGCCCTGT TCGAAGAGCC TGGCAATGGC     1380

ACCTTCTCAG TCGTCCTCAA CCAGCTCACT GCCGAGGATG AAGGCTTCTA CTGGTGTGTC     1440

AGCGATGACG ATGAGTCCCT GACGACTTCG GTGAAGCTCC AGATCGTTGA CGGAGAACCA     1500

AGCCCCACGA TCGACAAGTT CACTGCTGTG CAGGGAGAGC CTGTTGAGAT CACCTGCCAC     1560

TTCCCATGCA AATACTTCTC CTCCGAGAAG TACTGGTGCA AGTGGAATGA CCATGGCTGC     1620

GAGGACCTGC CCACTAAGCT CAGCTCCAGC GGCGACCTTG TGAAATGCAA CAACAACCTG     1680

GTCCTCACCC TGACCTTGGA CTCGGTCAGC GAAGATGACG AGGGCTGGTA CTGGTGTGGC     1740

GCGAAAGACG GGCACGAGTT TGAAGAGGTT GCGGCCGTCA GGGTGGAGCT GACAGAGCCA     1800

GCCAAGGTAG CTGTCGAGCC AGCCAAGGTA CCTGTCGACC CAGCCAAGGC AGCCCCCGCG     1860

CCTGCTGAGG AGAAGGCCAA GGCGCGGTGC CCAGTGCCCA GGAGAAGGCA GTGGTACCCA     1920

TTGTCAAGGA AGCTGAGAAC AAGTTGTCCA GAACCTCGGC TCCTTGCGGA GGAGGTAGCA     1980

GTGCAGAGTG CGGAAGACCC AGCCAGTGGG AGCAGAGCGT CTGTGGATGC CAGCAGTGCT     2040

TCGGACAAA GCGGGAGTGC CAAAGTACTG ATCTCCACCC TGGTGCCCTT GGGGCTGGTG     2100

CTGGCAGCGG GGGCCATGGC CGTGGCCATA GCCAGAGCCC GGCACAGGAG GAACGTGGAC     2160

CGAGTTTCCA TCGGAAGCTA CAGGACAGAC ATTAGCATGT CAGACTTGGA GAACTCCAGG     2220

GAGTTCGGAG CCATTGACAA CCCAAGCGCC TGCCCCGATG CCCGGGAGAC GGCCCTCGGA     2280

GGAAAGGATG AGTTAGCGAC GGCCACCGAG AGCACCGTGG AGATTGAGGA GCCCAAGAAG     2340

GCAAAACGGT CATCCAAGGA AGAAGCCGAC CTGGCCTACT CAGCTTTCCT GCTCCAATCC     2400

AACACCATAG CTGCTGAGCA CCAAGATGGC CCCAAGGAGG CCTAGGCACA GCCGGCCACC     2460

GCCGCCGCCG CCACCGCCGC CGCCGCCGCC ACCTGTGAAA ATCACCTTCC AGAATCACGT     2520

TGATCCTCGG GGTCCCCAGA GCCGGGGGCT CAACCGCCCT GCACCCCCCA TGTCCCCACC     2580

ACCTAAACTT CCCTACCTGT GCCCAGAGGT GTGCTGGTCC CCTCCTCCAC GGCATCCAGG     2640

CCTGGCTCAA TGTTCCCGTT GGGGTGGGGG TGTGAGGGGT TCCTACTTGC AGCCCGGTTC     2700

TCCCGAGAGA AGCTAAGGAT CCAGGTCCTG AGGGAGGGGC CTCTCGAAGG CAGACAGACC     2760

AGAGAGGGGG GAGGAGCCCT TGGATGGGAG GCCAGAGGCG CTTTCCGGCC ACCCCCTCCC     2820

TCCCTGCCCC CACCCTCCTT CCTTCATTCA AAAGTCCCAG TGGCTGCTGC CTAGGGTCCA     2880

GGCGCTGGCC GCACGCCTCC TCGAAGCCGT TGTGCAAACA TCACTGGAGG AAGCCAGGGC     2940

TCCTCCCGGG CTGTGTATCC TCACTCAGGC ATCCTGTCCT CCCCAGTATC AGGAGATGTC     3000

AAGCGTCTGA AGGCTGTGTG CCCTGGGCGT GTCTGCAAGT CACCCCAGAC ACATGTTCTC     3060

GCCATTTTAC AGATGAGAAC ACTGAGGTTG TACTCAAGGG CACCCTGCGA GATGGAGCAA     3120

CAGCAAACTA GATGGGCTTC TGCTGTCCTC TTGGCCAGAG GTCTCTCCAC AGGAGCCCCT     3180

GCCCCTGTAG GAAGCAGAGT TTTAGAACAT GGAAGAAGAA GAGGGGGATG GCCCTGGACG     3240

CTGACCTCTC CCAAGCCCCC ACGGGGGAAA AGGCCCCCTC CTTTTCTGTC ACTCTCGGGG     3300

ACCTGCGGAG TTGAGCATTC GTGCCCCGTG TGTCTGAAGA GTTCCAGTG GAAAGAAGAA     3360

AAGAGGGTGT TTGTCAGTGC CGGGGAGGGC CTGATCCCCA GACAGCTGAA GTTTAAGGTC     3420
```

```
CTTGTCCCTG TGAGCTTTAA CCAGCACCTC CGGGCTGACC CTTGCTAACA CATCAGAAAT      3480

GTGATTTAAT CATTAAACAT TGTGATTGCC ACTGGGA                               3517
```

(2) INFORMATION FOR SEQ ID NO: 21:

(i) SEQUENCE CHARACTERISTICS:
        (A) LENGTH: 1875 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..1875

(xi) SEQUENCE DESCRIPTION: SEQ ID NO: 21:

```
ATG GCT CTC TTC TTG CTC ACC TGC CTG CTG GCT GTC TTT TCA GCG GCC        48
Met Ala Leu Phe Leu Leu Thr Cys Leu Leu Ala Val Phe Ser Ala Ala
 1               5                  10                  15

ACG GCA CAA AGC TCC TTA TTG GGT CCC AGC TCC ATA TTT GGT CCC GGG        96
Thr Ala Gln Ser Ser Leu Leu Gly Pro Ser Ser Ile Phe Gly Pro Gly
                20                  25                  30

GAG GTG AAT GTT TTG GAA GGC GAC TCG GTG TCC ATC ACA TGC TAC TAC       144
Glu Val Asn Val Leu Glu Gly Asp Ser Val Ser Ile Thr Cys Tyr Tyr
            35                  40                  45

CCA ACA ACC TCC GTC ACC CGG CAC AGC CGG AAG TTC TGG TGC CGG GAA       192
Pro Thr Thr Ser Val Thr Arg His Ser Arg Lys Phe Trp Cys Arg Glu
 50                  55                  60

GAG GAG AGC GGC CGC TGC GTG ACG CTT GCC TCG ACC GGC TAC ACG TCC       240
Glu Glu Ser Gly Arg Cys Val Thr Leu Ala Ser Thr Gly Tyr Thr Ser
 65                  70                  75                  80

CAG GAA TAC TCC GGG AGA GGC AAG CTC ACC GAC TTC CCT GAT AAA GGG       288
Gln Glu Tyr Ser Gly Arg Gly Lys Leu Thr Asp Phe Pro Asp Lys Gly
                85                  90                  95

GAG TTT GTG GTG ACT GTT GAC CAA CTC ACC CAG AAC GAC TCA GGG AGC       336
Glu Phe Val Val Thr Val Asp Gln Leu Thr Gln Asn Asp Ser Gly Ser
            100                 105                 110

TAC AAG TGT GGC GTG GGA GTC AAC GGC CGT GGC CTG GAC TTC GGT GTC       384
Tyr Lys Cys Gly Val Gly Val Asn Gly Arg Gly Leu Asp Phe Gly Val
        115                 120                 125

AAC GTG CTG GTC AGC CAG AAG CCA GAG CCT GAT GAC GTT GTT TAC AAA       432
Asn Val Leu Val Ser Gln Lys Pro Glu Pro Asp Asp Val Val Tyr Lys
    130                 135                 140

CAA TAT GAG AGT TAT ACA GTA ACC ATC ACC TGC CCT TTC ACA TAT GCG       480
Gln Tyr Glu Ser Tyr Thr Val Thr Ile Thr Cys Pro Phe Thr Tyr Ala
145                 150                 155                 160

ACT AGG CAA CTA AAG AAG TCC TTT TAC AAG GTG GAA GAC GGG GAA CTT       528
Thr Arg Gln Leu Lys Lys Ser Phe Tyr Lys Val Glu Asp Gly Glu Leu
                165                 170                 175

GTA CTC ATC ATT GAT TCC AGC AGT AAG GAG GCA AAG GAC CCC AGG TAT       576
Val Leu Ile Ile Asp Ser Ser Ser Lys Glu Ala Lys Asp Pro Arg Tyr
            180                 185                 190

AAG GGC AGA ATA ACG TTG CAG ATC CAA AGT ACC ACA GCA AAA GAA TTC       624
Lys Gly Arg Ile Thr Leu Gln Ile Gln Ser Thr Thr Ala Lys Glu Phe
        195                 200                 205
```

```
ACA GTC ACC ATC AAG CAT TTG CAG CTC AAT GAT GCT GGG CAG TAT GTC      672
Thr Val Thr Ile Lys His Leu Gln Leu Asn Asp Ala Gly Gln Tyr Val
    210             215             220

TGC CAG AGT GGA AGC GAC CCC ACT GCT GAA GAA CAG AAC GTT GAC CTC      720
Cys Gln Ser Gly Ser Asp Pro Thr Ala Glu Glu Gln Asn Val Asp Leu
225             230             235             240

CGA CTG CTA ACT CCT GGT CTG CTC TAT GGA AAC CTG GGG GGC TCG GTG      768
Arg Leu Leu Thr Pro Gly Leu Leu Tyr Gly Asn Leu Gly Gly Ser Val
            245             250             255

ACC TTT GAA TGT GCC CTG GAC TCT GAA GAC GCA AAC GCG GTA GCA TCC      816
Thr Phe Glu Cys Ala Leu Asp Ser Glu Asp Ala Asn Ala Val Ala Ser
                260             265             270

TTG CGC CAG GTT AGG GGT GGC AAT GTG GTC ATT GAC AGC CAG GGG ACA      864
Leu Arg Gln Val Arg Gly Gly Asn Val Val Ile Asp Ser Gln Gly Thr
        275             280             285

ATA GAT CCA GCC TTC GAG GGC AGG ATC CTG TTC ACC AAG GCT GAG AAC      912
Ile Asp Pro Ala Phe Glu Gly Arg Ile Leu Phe Thr Lys Ala Glu Asn
290             295             300

GGC CAC TTC AGT GTA GTG ATC GCA GGC CTG AGG AAG GAA GAC ACA GGG      960
Gly His Phe Ser Val Val Ile Ala Gly Leu Arg Lys Glu Asp Thr Gly
305             310             315             320

AAC TAT CTG TGC GGA GTC CAG TCC AAT GGT CAG TCT GGG GAT GGG CCC     1008
Asn Tyr Leu Cys Gly Val Gln Ser Asn Gly Gln Ser Gly Asp Gly Pro
            325             330             335

ACC CAG CTT CGG CAA CTC TTC GTC AAT GAA GAG ATC GAC GTG TCC CGC     1056
Thr Gln Leu Arg Gln Leu Phe Val Asn Glu Glu Ile Asp Val Ser Arg
                340             345             350

AGC CCC CCT GTG TTG AAG GGC TTT CCA GGA GGC TCC GTG ACC ATA CGC     1104
Ser Pro Pro Val Leu Lys Gly Phe Pro Gly Gly Ser Val Thr Ile Arg
        355             360             365

TGC CCC TAC AAC CCG AAG AGA AGC GAC AGC CAC CTG CAG CTG TAT CTC     1152
Cys Pro Tyr Asn Pro Lys Arg Ser Asp Ser His Leu Gln Leu Tyr Leu
370             375             380

TGG GAA GGG AGT CAA ACC CGC CAT CTG CTG GTG GAC AGC GGC GAG GGG     1200
Trp Glu Gly Ser Gln Thr Arg His Leu Leu Val Asp Ser Gly Glu Gly
385             390             395             400

CTG GTT CAG AAA GAC TAC ACA GGC AGG CTG GCC CTG TTC GAA GAG CCT     1248
Leu Val Gln Lys Asp Tyr Thr Gly Arg Leu Ala Leu Phe Glu Glu Pro
            405             410             415

GGC AAT GGC ACC TTC TCA GTC GTC CTC AAC CAG CTC ACT GCC GAG GAT     1296
Gly Asn Gly Thr Phe Ser Val Val Leu Asn Gln Leu Thr Ala Glu Asp
                420             425             430

GAA GGC TTC TAC TGG TGT GTC AGC GAT GAC GAT GAG TCC CTG ACG ACT     1344
Glu Gly Phe Tyr Trp Cys Val Ser Asp Asp Asp Glu Ser Leu Thr Thr
        435             440             445

TCG GTG AAG CTC CAG ATC GTT GAC GGA GAA CCA AGC CCC ACG ATC GAC     1392
Ser Val Lys Leu Gln Ile Val Asp Gly Glu Pro Ser Pro Thr Ile Asp
450             455             460

AAG TTC ACT GCT GTG CAG GGA GAG CCT GTT GAG ATC ACC TGC CAC TTC     1440
Lys Phe Thr Ala Val Gln Gly Glu Pro Val Glu Ile Thr Cys His Phe
465             470             475             480

CCA TGC AAA TAC TTC TCC TCC GAG AAG TAC TGG TGC AAG TGG AAT GAC     1488
Pro Cys Lys Tyr Phe Ser Ser Glu Lys Tyr Trp Cys Lys Trp Asn Asp
            485             490             495

CAT GGC TGC GAG GAC CTG CCC ACT AAG CTC AGC TCC AGC GGC GAC CTT     1536
His Gly Cys Glu Asp Leu Pro Thr Lys Leu Ser Ser Ser Gly Asp Leu
                500             505             510

GTG AAA TGC AAC AAC AAC CTG GTC CTC ACC CTG ACC TTG GAC TCG GTC     1584
Val Lys Cys Asn Asn Asn Leu Val Leu Thr Leu Thr Leu Asp Ser Val
        515             520             525
```

-continued

```
AGC GAA GAT GAC GAG GGC TGG TAC TGG TGT GGC GCG AAA GAC GGG CAC    1632
Ser Glu Asp Asp Glu Gly Trp Tyr Trp Cys Gly Ala Lys Asp Gly His
    530                 535                 540

GAG TTT GAA GAG GTT GCG GCC GTC AGG GTG GAG CTG ACA GAG CCA GCC    1680
Glu Phe Glu Glu Val Ala Ala Val Arg Val Glu Leu Thr Glu Pro Ala
545                 550                 555                 560

AAG GTA GCT GTC GAG CCA GCC AAG GTA CCT GTC GAC CCA GCC AAG GCA    1728
Lys Val Ala Val Glu Pro Ala Lys Val Pro Val Asp Pro Ala Lys Ala
                565                 570                 575

GCC CCC GCG CCT GCT GAG GAG AAG GCC AAG GCG CGG TGC CCA GTG CCC    1776
Ala Pro Ala Pro Ala Glu Glu Lys Ala Lys Ala Arg Cys Pro Val Pro
            580                 585                 590

AGG AGA AGG CAG TGG TAC CCA TTG TCA AGG AAG CTG AGA ACA AGT TGT    1824
Arg Arg Arg Gln Trp Tyr Pro Leu Ser Arg Lys Leu Arg Thr Ser Cys
        595                 600                 605

CCA GAA CCT CGG CTC CTT GCG GAG GAG GTA GCA GTG CAG AGT GCG GAA    1872
Pro Glu Pro Arg Leu Leu Ala Glu Glu Val Ala Val Gln Ser Ala Glu
    610                 615                 620

TAA                                                                1875
```

(2) INFORMATION FOR SEQ ID NO: 22:

(i) SEQUENCE CHARACTERISTICS:
        (A) LENGTH: 624 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Ala Leu Phe Leu Leu Thr Cys Leu Leu Ala Val Phe Ser Ala Ala
1               5                   10                  15

Thr Ala Gln Ser Ser Leu Leu Gly Pro Ser Ser Ile Phe Gly Pro Gly
            20                  25                  30

Glu Val Asn Val Leu Glu Gly Asp Ser Val Ser Ile Thr Cys Tyr Tyr
        35                  40                  45

Pro Thr Thr Ser Val Thr Arg His Ser Arg Lys Phe Trp Cys Arg Glu
    50                  55                  60

Glu Ser Gly Arg Cys Val Thr Leu Ala Ser Thr Gly Tyr Thr Ser
65                  70                  75                  80

Gln Glu Tyr Ser Gly Arg Gly Lys Leu Thr Asp Phe Pro Asp Lys Gly
                85                  90                  95

Glu Phe Val Val Thr Val Asp Gln Leu Thr Gln Asn Asp Ser Gly Ser
            100                 105                 110

Tyr Lys Cys Gly Val Gly Val Asn Gly Arg Gly Leu Asp Phe Gly Val
        115                 120                 125

Asn Val Leu Val Ser Gln Lys Pro Glu Pro Asp Asp Val Val Tyr Lys
    130                 135                 140

Gln Tyr Glu Ser Tyr Thr Val Thr Ile Thr Cys Pro Phe Thr Tyr Ala
145                 150                 155                 160

Thr Arg Gln Leu Lys Lys Ser Phe Tyr Lys Val Glu Asp Gly Glu Leu
                165                 170                 175

Val Leu Ile Ile Asp Ser Ser Lys Glu Ala Lys Asp Pro Arg Tyr
            180                 185                 190

Lys Gly Arg Ile Thr Leu Gln Ile Gln Ser Thr Thr Ala Lys Glu Phe
        195                 200                 205

Thr Val Thr Ile Lys His Leu Gln Leu Asn Asp Ala Gly Gln Tyr Val
    210                 215                 220
```

-continued

```
Cys Gln Ser Gly Ser Asp Pro Thr Ala Glu Glu Gln Asn Val Asp Leu
225                 230                 235                 240

Arg Leu Leu Thr Pro Gly Leu Leu Tyr Gly Asn Leu Gly Gly Ser Val
            245                 250                 255

Thr Phe Glu Cys Ala Leu Asp Ser Glu Asp Ala Asn Ala Val Ala Ser
        260                 265                 270

Leu Arg Gln Val Arg Gly Gly Asn Val Val Ile Asp Ser Gln Gly Thr
    275                 280                 285

Ile Asp Pro Ala Phe Glu Gly Arg Ile Leu Phe Thr Lys Ala Glu Asn
290                 295                 300

Gly His Phe Ser Val Val Ile Ala Gly Leu Arg Lys Glu Asp Thr Gly
305                 310                 315                 320

Asn Tyr Leu Cys Gly Val Gln Ser Asn Gly Gln Ser Gly Asp Gly Pro
                325                 330                 335

Thr Gln Leu Arg Gln Leu Phe Val Asn Glu Ile Asp Val Ser Arg
            340                 345                 350

Ser Pro Pro Val Leu Lys Gly Phe Pro Gly Gly Ser Val Thr Ile Arg
            355                 360                 365

Cys Pro Tyr Asn Pro Lys Arg Ser Asp Ser His Leu Gln Leu Tyr Leu
        370                 375                 380

Trp Glu Gly Ser Gln Thr Arg His Leu Leu Val Asp Ser Gly Glu Gly
385                 390                 395                 400

Leu Val Gln Lys Asp Tyr Thr Gly Arg Leu Ala Leu Phe Glu Glu Pro
                405                 410                 415

Gly Asn Gly Thr Phe Ser Val Val Leu Asn Gln Leu Thr Ala Glu Asp
            420                 425                 430

Glu Gly Phe Tyr Trp Cys Val Ser Asp Asp Glu Ser Leu Thr Thr
        435                 440                 445

Ser Val Lys Leu Gln Ile Val Asp Gly Glu Pro Ser Pro Thr Ile Asp
450                 455                 460

Lys Phe Thr Ala Val Gln Gly Glu Pro Val Glu Ile Thr Cys His Phe
465                 470                 475                 480

Pro Cys Lys Tyr Phe Ser Ser Glu Lys Tyr Trp Cys Lys Trp Asn Asp
                485                 490                 495

His Gly Cys Glu Asp Leu Pro Thr Lys Leu Ser Ser Ser Gly Asp Leu
            500                 505                 510

Val Lys Cys Asn Asn Asn Leu Val Leu Thr Leu Thr Leu Asp Ser Val
        515                 520                 525

Ser Glu Asp Asp Glu Gly Trp Tyr Trp Cys Gly Ala Lys Asp Gly His
530                 535                 540

Glu Phe Glu Glu Val Ala Ala Val Arg Val Glu Leu Thr Glu Pro Ala
545                 550                 555                 560

Lys Val Ala Val Glu Pro Ala Lys Val Pro Val Asp Pro Ala Lys Ala
                565                 570                 575

Ala Pro Ala Pro Ala Glu Glu Lys Ala Lys Ala Arg Cys Pro Val Pro
            580                 585                 590

Arg Arg Arg Gln Trp Tyr Pro Leu Ser Arg Lys Leu Arg Thr Ser Cys
    595                 600                 605

Pro Glu Pro Arg Leu Leu Ala Glu Glu Val Ala Val Gln Ser Ala Glu
610                 615                 620
```

(2) INFORMATION FOR SEQ ID NO: 23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 23:

```
GATCTATGAA GACCCACCTG CTT                                          23
```

(2) INFORMATION FOR SEQ ID NO: 24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 24:

```
AATTCTTAGA CAGGGTAGCA AGA                                          23
```

(2) INFORMATION FOR SEQ ID NO: 25:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..480

(xi) SEQUENCE DESCRIPTION: SEQ ID NO: 25:

```
ATG AAG ACC CAC CTG CTT CTC TGG GGA GTC CTC GCC ATT TTT GTT AAG    48
Met Lys Thr His Leu Leu Leu Trp Gly Val Leu Ala Ile Phe Val Lys
 1               5                  10                  15

GTT GTC CTT GTA ACA GGT GAC GAC GAA GCG ACC ATT CTT GCT GAC AAC    96
Val Val Leu Val Thr Gly Asp Asp Glu Ala Thr Ile Leu Ala Asp Asn
                20                  25                  30

AAA TGC ATG TGT ACC CGA GTT ACC TCT AAA ATC ATC CCT TCC ACC GAG   144
Lys Cys Met Cys Thr Arg Val Thr Ser Lys Ile Ile Pro Ser Thr Glu
         35                  40                  45

GAT CCT AAT GAG GAC ATT GTG GAG AGA AAT ATC CGA ATT GTT GTC CCT   192
Asp Pro Asn Glu Asp Ile Val Glu Arg Asn Ile Arg Ile Val Val Pro
     50                  55                  60

TTG AAC AAC AGG GAG AAT ATC TCT GAT CCC ACC TCC CCA CTG AGA AGG   240
Leu Asn Asn Arg Glu Asn Ile Ser Asp Pro Thr Ser Pro Leu Arg Arg
 65                  70                  75                  80
```

-continued

```
AAC TTT GTA TAC CAT TTG TCA GAC GTC TGT AAG AAA TGC GAT CCT GTG      288
Asn Phe Val Tyr His Leu Ser Asp Val Cys Lys Lys Cys Asp Pro Val
             85                  90                  95

GAA GTG GAG CTG GAA GAT CAG GTT GTT ACT GCC ACC CAG AGC AAC ATC      336
Glu Val Glu Leu Glu Asp Gln Val Val Thr Ala Thr Gln Ser Asn Ile
            100                 105                 110

TGC AAT GAA GAC GAT GGT GTT CCT GAG ACC TGC TAC ATG TAT GAC AGA      384
Cys Asn Glu Asp Asp Gly Val Pro Glu Thr Cys Tyr Met Tyr Asp Arg
            115                 120                 125

AAC AAG TGC TAT ACC ACT ATG GTC CCA CTT AGG TAT CAT GGT GAG ACC      432
Asn Lys Cys Tyr Thr Thr Met Val Pro Leu Arg Tyr His Gly Glu Thr
        130                 135                 140

AAA ATG GTG CAA GCA GCC TTG ACC CCC GAT TCT TGC TAC CCT GAC TAA      480
Lys Met Val Gln Ala Ala Leu Thr Pro Asp Ser Cys Tyr Pro Asp
145                 150                 155
```

(2) INFORMATION FOR SEQ ID NO: 26:

(i) SEQUENCE CHARACTERISTICS:
        (A) LENGTH: 159 amino acids
        (B) TYPE: amino acid
        (D) TOPOLOGY: linear (ii) MOLECULE TYPE: protein (xi) SEQUENCE DESCRIPTION: SEQ ID NO: 26:

```
Met Lys Thr His Leu Leu Leu Trp Gly Val Leu Ala Ile Phe Val Lys
 1               5                  10                  15

Val Val Leu Val Thr Gly Asp Asp Glu Ala Thr Ile Leu Ala Asp Asn
            20                  25                  30

Lys Cys Met Cys Thr Arg Val Thr Ser Lys Ile Ile Pro Ser Thr Glu
        35                  40                  45

Asp Pro Asn Glu Asp Ile Val Glu Arg Asn Ile Arg Ile Val Val Pro
    50                  55                  60

Leu Asn Asn Arg Glu Asn Ile Ser Asp Pro Thr Ser Pro Leu Arg Arg
65                  70                  75                  80

Asn Phe Val Tyr His Leu Ser Asp Val Cys Lys Lys Cys Asp Pro Val
                85                  90                  95

Glu Val Glu Leu Glu Asp Gln Val Val Thr Ala Thr Gln Ser Asn Ile
            100                 105                 110

Cys Asn Glu Asp Asp Gly Val Pro Glu Thr Cys Tyr Met Tyr Asp Arg
            115                 120                 125

Asn Lys Cys Tyr Thr Thr Met Val Pro Leu Arg Tyr His Gly Glu Thr
        130                 135                 140

Lys Met Val Gln Ala Ala Leu Thr Pro Asp Ser Cys Tyr Pro Asp
145                 150                 155
```

TRANSGENIC PLANTS EXPRESSING ASSEMBLED SECRETORY ANTIBODIES

CROSS REFERENCE TO RELATED APPLICATION

This application is a Continuation application of U.S. Ser. No. 09/199,534, filed Nov. 25, 1998, now issued as U.S. Pat. No. 6,417,429 on Jul. 9, 2002, which is a Continuation application of U.S. Ser. No. 08/642,406, filed May 3, 1996, now issued as U.S. Pat. No. 5,959,177 on Sep. 28, 1999, which is a continuation-in-part of U.S. Ser. No. 07/971,951, filed Nov. 5, 1992, now issued as U.S. Pat. No. 5,639,947 on Jun. 17, 1997, which is a Continuation of U.S. Ser. No. 07/591,823, filed Oct. 2, 1990, now issued as U.S. Pat. No. 5,202,422, which is a continuation-in-part of U.S. Ser. No. 07/427,765, filed Oct. 27, 1989, now abandoned, the disclosures of all of which are herein incorporated by reference in their entirety.

TECHNICAL FIELD

The present invention relates to expression and assembly of foreign multimeric proteins—e.g., antibodies—in plants, as well as to transgenic plants that express such proteins.

BACKGROUND

It is known that polypeptides can be expressed in a wide variety of cellular hosts. A wide variety of structural genes have been isolated from mammals and viruses, joined to transcriptional and translational initiation and termination regulatory signals from a source other than the structural gene, and introduced into hosts into which these regulatory signals are functional.

For economic reasons, it would be desirable to utilize genetically engineered unicellular microorganisms to produce a wide variety of polypeptides. However, because of the inherent differences in the nature of unicellular organisms on one hand and mammalian cells on the other, the folding and processing of polypeptides in unicellular microorganisms appears to be quite different from the folding and processing that is effected in mammalian cells. As a result, mammalian polypeptides derived from unicellular microorganisms are not always properly folded or processed to provide the desired degree of biological or physiological activity in the obtained polypeptide.

To that end attempts have been made, with varying degrees of success, to express mammalian polypeptides in plants. One particularly important polypeptide is secretory immunoglobulin A.

Secretory immunoglobulin A (SIgA) is the most abundant form of immunoglobulin (Ig) in mucosal secretions, where it forms part of the first line of defense against infectious agents. The molecule exists mainly in the 11S dimeric form, in which two monomeric IgA antibody units are associated with the small polypeptide joining (J) chain and with a fourth polypeptide, secretory component (SC). The ability to produce monoclonal SIgA would be of substantial value, but the synthesis is complicated because it requires plasma cells secreting dimeric IgA (dIga) as well as epithelial cells expressing the polymeric Ig receptor (pIgR). Normally, pIgR on the epithelial basolateral surface binds dIgA, initiating a process of endocytosis, transcytosis, phosphorylation, proteolysis, and ultimate release of the SIgA complex at the apical surface into the secretion (Mostov, *Ann. Rev. Immunol.* 12: 63 (1994)). Thus, it is important to focus on the ability of transgenic plants to assemble secretory antibodies.

Secretory IgA is resistant to denaturation caused by harsh environments. This denaturation resistance requires that the complex secretory IgA molecule containing IgA molecules, J chain and secretory component be accurately and efficiently assembled. Until the present invention, assembly and expression of useful amounts of secretory IgA was impractical, due to low yields and due to the inability of the available mammalian systems to express and assemble SigA in a single cell. As disclosed herein, the foregoing problems have now been solved by the present invention.

The expression of a multimeric protein in plant cells requires that the genes coding for the polypeptide chains be present in the same plant cell. Until the advent of the procedures disclosed herein, the probability of actually introducing both genes into the same cell was extremely remote. Assembly of multimeric protein and expression of significant amounts of same has now been made feasible by use of the methods and constructs described herein.

Transgenic plants are emerging as an important system for the expression of many recombinant proteins, especially those intended for therapeutic purposes. One of their major attractions is the potential for protein production on an agricultural scale at an extremely competitive cost, but there are also many other advantages. Most plant transformation techniques result in the stable integration of the foreign DNA into the plant genome, so genetic recombination by crossing of transgenic plants is a simple method for introducing new genes and accumulating multiple genes into plants. Furthermore, the processing and assembly of recombinant proteins in plants may also complement that in mammalian cells, which may be an advantage over the more commonly used microbial expression systems.

One of the most useful aspects of using a recombinant expression system for antibody production is the ease with which the antibody can be tailored by molecular engineering. This allows the production of antibody fragments and single-chain molecules, as well as the manipulation of full-length antibodies. For example, a side range of functional recombinant-antibody fragments, such as Fab, $F_v$, single-chain and single-domain antibodies, may be generated. In addition, the ability of plant cells to produce full-length antibodies can be exploited for the production of antibody molecules with altered Fc-mediated properties. This is facilitated by the domain structure of immunoglobulin chains, which allows individual domains to be "cut and spliced" at the gene level. For example, the C-terminal domains of an IgG antibody heavy chain have been modified by replacing the $C\gamma2$ and $C\gamma3$ domains with $C\alpha2$ and $C\alpha3$ domains of an IgA antibody, while maintaining the correct assembly of the functional antibody in plants. These alterations have no effect on antigen binding or specificity, but may modify the protective functions of the antibody that are mediated through the Fc region.

It is also becoming more clear that specially engineered plants may provide an excellent source of various proteins, including therapeutic immunoglobulins, in large quantities and at a relatively low cost. Production of antibodies in plants may be of particular benefit in the area of topical and preventive immunotherapy.

For example, topically applied antibodies can prevent colonization by pathogenic bacteria, as well as modify the resident bacterial flora in a highly specific manner. In the case of dental caries, topically-applied monoclonal antibodies raised against the cell-surface adhesin of *Streptococcus mutans* prevents the bacteria from becoming established in non-human primates, and also reduces the level of disease (Lehner, et al., *Infect. Immun.* 50: 796–799 (1985)). In humans, the mAb was shown to confer long-term protection against *S. mutans* in adults (Ma, et al., *Infect. Immun.* 50: 3407–14 (1990)).

Thus, methods of providing useful immunoglobulins—particularly antibodies—in large quantities and at low cost confer a distinct advantage over other methodologies in current use. In addition, the relative ease with which one may engineer immunoglobulins and other large protein molecules using a recombinant expression system in plants, and the stability of those systems in succeeding generations, make transgenic plants an extremely attractive source of immunotherapeutic molecules.

SUMMARY OF THE INVENTION

Therefore, methods of producing active biomolecules with relative ease and in large quantities are now disclosed. In addition, the molecules and compositions produced thereby are disclosed as well.

Thus, in one embodiment, the present invention contemplates a method of generating and assembling secretory antibodies within a single cell, said method comprising: (a) introducing into the genome of a first member of a plant species a first mammalian nucleotide sequence encoding an immunoglobulin heavy chain portion-containing polypeptide including a leader sequence forming a secretion signal, to produce a first transformant; (b) introducing into the genome of a second member of said plant species a second mammalian nucleotide sequence encoding a polypeptide linker or joining chain, to produce a second transformant; (c) introducing into the genome of a third member of said plant species a third mammalian nucleotide sequence encoding a secretory component, to produce a third transformant; (d) sexually crossing said transformants to generate a progeny population containing all three mammalian sequences; and (e) isolating from said progeny population a transgenic plant species producing a secretory antibody. In one variation of the foregoing method, the nucleotide sequences are introduced via separate vectors. In alternative variations, the immunoglobulin heavy chain portion-containing polypeptide may be an alpha heavy chain portion-containing polypeptide, a single-chain antibody or fragment thereof, or a heavy chain portion-containing polypeptide comprising one or more variable regions.

Thus, in one embodiment, the present invention contemplates a method of generating and assembling secretory antibodies within a single cell, said method comprising: (a) introducing into the genome of a first member of a plant species a first mammalian nucleotide sequence encoding an immunoglobulin heavy chain portion-containing polypeptide including a leader sequence forming a secretion signal, to produce a first transformant; (b) introducing into the genome of a second member of said plant species a second mammalian nucleotide sequence encoding an immunoglobulin light chain portion-containing polypeptide including a leader sequence forming a secretion signal to produce a second transformant; (c) introducing into the genome of a third member of said plant species a third mammalian nucleotide sequence encoding a polypeptide linker or joining chain, to produce a third transformant; (d) introducing into the genome of a fourth member of said plant species a fourth mammalian nucleotide sequence encoding a secretory component, to produce a fourth transformant; (e) sexually crossing said transformants to generate a progeny population containing all four mammalian sequences; and (f) isolating from said progeny population a transgenic plant species producing a secretory antibody. In one variation of the foregoing method, the nucleotide sequences are introduced via separate vectors. In alternative variations, the immunoglobulin heavy chain portion-containing polypeptide may be an alpha heavy chain portion-containing polypeptide, a single-chain antibody or fragment thereof, or a heavy chain portion-containing polypeptide comprising one or more variable regions.

The invention further contemplates a method as described above, wherein isolated from said progeny population is a plant species that produces the corresponding Fab fragment. In another variation, a plant species that produces the corresponding $F_v$ fragment is isolated from the progeny population.

The invention also discloses a variety of transgenic plants. In one embodiment, a transgenic plant comprising (a) plant cells that containing nucleotide sequences encoding immunoglobulin heavy- and light-chain polypeptides, a nucleotide sequence encoding a polypeptide linker or joining chain, and a nucleotide sequence encoding a secretory component; and (b) immunologically active secretory antibodies encoded by said nucleotide sequences is disclosed. In one variation, all four nucleotide sequences are contained within a single cell. In still another variation, each of the nucleotide sequences is included on a separate vector. In other alternative variations, the immunoglobulin heavy chain portion-containing polypeptide may be an alpha heavy chain portion-containing polypeptide, a single-chain antibody or fragment thereof, or a heavy chain portion-containing polypeptide comprising one or more variable regions.

In another embodiment, a transgenic plant of the present invention comprises (a) plant cells that containing nucleotide sequences encoding immunoglobulin heavy-chain polypeptides, a nucleotide sequence encoding a polypeptide linker or joining chain, and a nucleotide sequence encoding a secretory component; and (b) immunologically active secretory antibodies encoded by said nucleotide sequences is disclosed. In one variation, all three nucleotide sequences are contained within a single cell. In still another variation, each of the nucleotide sequences is included on a separate vector. In other alternative variations, the immunoglobulin heavy chain portion-containing polypeptide may be an alpha heavy chain portion-containing polypeptide, a single-chain antibody or fragment thereof, or a heavy chain portion-containing polypeptide comprising one or more variable regions.

In various alternative embodiments, the immunoglobulin molecules comprise Fab fragments or $F_v$ fragments. In still other variations, the plant may be a dicot or a monocot. In one exemplary embodiment, the plant is a tobacco plant.

The invention also discloses methods of passively immunizing a human or animal subject against a preselected ligand, comprising administering to said subject a prophylactic amount of a biologically active immunoglobulin molecule capable of binding a preselected ligand, wherein said molecule is free from detectable sialic acid residues. In one variation, the immunoglobulin molecule is encapsulated in a plant cell. In another variation, the immunoglobulin molecule is administered as part of a composition, which composition further comprises a material having nutritional value. In alternative embodiments, the material having nutritional value is derived from a plant or an animal. In still another variation, the immunoglobulin molecule is administered as part of a composition, which composition further comprises a physiologically inert material.

In all the aforementioned embodiments, the immunoglobulin may be an antibody or an immunologically active derivative or fragment thereof. In one variation, the immunoglobulin is secretory IgA or an immunologically active derivative or fragment thereof.

In all the above-noted embodiments, the preselected ligand is an antigenic molecule. In one variation the ligand is a pathogen antigen.

Various combinations of the foregoing embodiments are contemplated by the present invention, as are embodiments including other aspects recited in the complete specification, of which this is but a part

BRIEF DESCRIPTION OF THE DRAWINGS

In FIG. 4A, plant extract binding to purified SA I/II, detected with HRP-labeled antiserum to the κ light chain is shown. In FIG. 4B, plant extract binding to purified SA I/II, detected with sheep antiserum to SC followed by alkaline phosphatase-labeled donkey antiserum to sheep Ig is shown. In FIG. 4C, plant extract binding to streptococcal cells, detected with sheep antiserum to SC followed by alkaline phosphatase-labeled donkey antiserum to sheep Ig is shown.

DETAILED DESCRIPTION OF THE INVENTION

A. Definitions

Figure 1A:
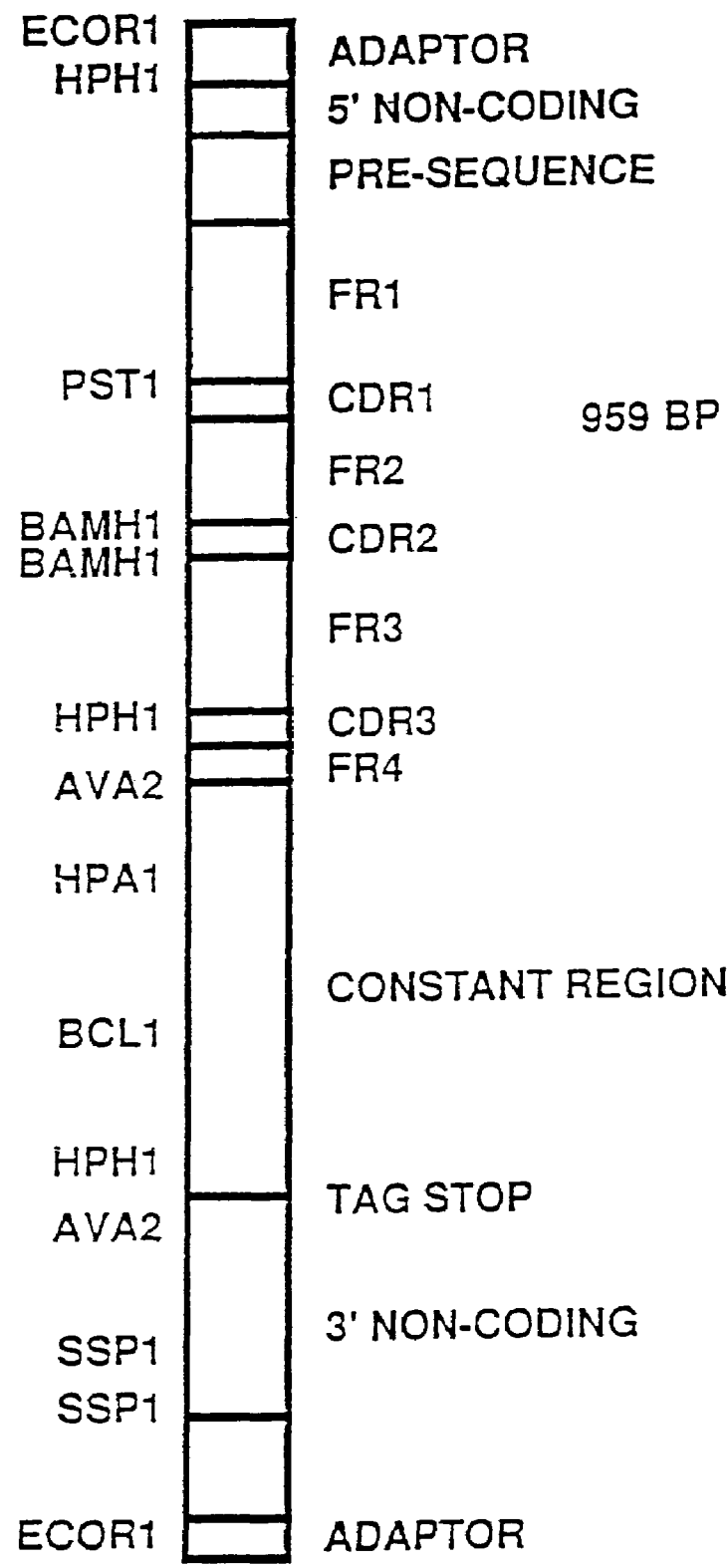
FIGS. 1A and 1B are schematics showing the major features of the kappa chain cDNA (FIG. 1A) and the gamma chain cDNA, (FIG. 1B), from the 6D4 hybridoma The location of important restriction endonuclease sites is also shown. The location of the complementarity determining regions, the framework regions and the constant regions are indicated.

Dicotyledon (dicot): A flowering plant whose embryos have two seed halves or cotyledons. Examples of dicots are: tobacco; tomato; the legumes including alfalfa; oaks; maples; roses; mints; squashes; daisies; walnuts; cacti; violets; and buttercups.

Monocotyledon (monocot): A flowering plant whose embryos have one cotyledon or seed leaf. Examples of monocots are: lilies; grasses; corn; grains, including oats, wheat and barley; orchids; irises; onions and palms.

Lower plant: Any non-flowering plant including ferns, gymnosperms, conifers, horsetails, club mosses, liver warts, hornworts, mosses, red algae, brown algae, gametophytes, sporophytes of pteridophytes, and green algae.

Eukaryotic hybrid vector: A DNA by means of which a DNA coding for a polypeptide (insert) can be introduced into a eukaryotic cell.

Extrachromosomal ribosomal DNA (rDNA): A DNA found in unicellular eukaryotes outside the chromosomes, carrying one or more genes coding for ribosomal RNA and replicating autonomously (independent of the replication of the chromosomes).

Palindromic DNA: A DNA sequence with one or more centers of symmetry.

DNA: Desoxyribonucleic acid.
T-DNA: A segment of transferred DNA.
rDNA: Ribosomal DNA.
RNA: Ribonucleic acid.
rRNA: Ribosomal RNA.
Ti-plasmid: Tumor-inducing plasmid.
Ti-DNA: A segment of DNA from Ti-plasmid.

Insert: A DNA sequence foreign to the rDNA, consisting of a structural gene and optionally additional DNA sequences.

Structural gene: A gene coding for a polypeptide and being equipped with a suitable promoter, termination sequence and optionally other regulatory DNA sequences, and having a correct reading frame.

Signal Sequence: A DNA sequence coding for an amino acid sequence attached to the polypeptide which binds the polypeptide to the endoplasmic reticulum and is essential for protein secretion. This sequence may also be referred to herein as a secretion signal or secretion signal sequence. The term "signal sequence" may also be used to refer to the sequence of amino acids that determines whether a protein will be formed on the rough endoplasmic reticulum or on free ribosomes. And while a "leader sequence" generally means a sequence near the 5' end of a nucleic acid strand or the amino terminus of a protein that functions in targeting or regulation, the term is sometimes used herein to include a "secretion signal" or a "signal sequence".

(Selective) Genetic mark e. A DNA sequence coding for a phenotypic trait by means of which transformed cells can be selected from untransformed cells.

Promoter: A recognition site on a DNA sequence or group of DNA sequences that provide an expression control element for a gene and to which RNA polymerase specifically binds and initiates RNA synthesis (transcription) of that gene.

Inducible promoter: A promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like.

Viral promoter: A promoter with a DNA sequence substantially similar to the promoter found at the 5' end of a viral gene. A typical viral promoter is found at the 5' end of the gene coding for the p21 protein of MMTV described by Huang et al., *Cell* 27: 245 (1981). (All references cited in this application are incorporated by reference.)

Synthetic promoter: A promoter that was chemically synthesized rather than biologically derived. Usually synthetic promoters incorporate sequence changes that optimize the efficiency of RNA polymerase initiation.

Constitutive promoter: A promoter where the rate of RNA polymerase binding and initiation is approximately constant and relatively independent of external stimuli. Examples of constitutive promoters include the cauliflower mosaic virus 35S and 19S promoters described by Poszkowski et al., *EMBO J.* 3: 2719 (1989) and Odell et al., *Nature* 313: 810 (1985).

Temporally regulated promoter A promoter where the rate of RNA polymerase binding and initiation is modulated at a specific time during development. Examples of temporally regulated promoters are given in Chua et al., *Science* 244: 174–181 (1989).

Spatially regulated promoter: A promoter where the rate of RNA polymerase binding and initiation is modulated in a specific structure of the organism such as the leaf, stem or root Examples of spatially regulated promoters are given in Chua et al., *Science* 244: 174–181 (1989).

Spatiotemporally regulated promoter: A promoter where the rate of RNA polymerase binding and initiation is modulated in a specific structure of the organism at a specific time during development. A typical spatiotemporally regulated promoter is the EPSP synthase-35S promoter described by Chua et al., Id. (1989).

Single-chain antigen-binding protein: A polypeptide composed of an immunoglobulin light-chain variable region amino acid sequence ($V_L$) tethered to an immunoglobulin heavy-chain variable region amino acid sequence ($V_H$) by a peptide that links the carboxyl terminus of the $V_L$ sequence to the amino terminus of the $V_H$ sequence.

Single-chain antigen-binding protein-coding gene: A recombinant gene coding for a single-chain antigen-binding protein.

Multimeric protein: A globular protein containing more than one separate polypeptide or protein chain associated with each other to form a single globular protein. Both heterodimeric and homodimeric proteins are multimeric proteins.

Polypeptide and peptide: A linear series of amino acid residues connected one to the other by peptide bonds between the alpha-amino and carboxy groups of adjacent residues.

Protein: A linear series of greater than about 50 amino acid residues connected one to the other as in a polypeptide.

Chelating agent: A chemical compound, peptide or protein capable of binding a metal. Examples of chelating agents include ethylene diamine tetra acetic acid (EDTA), ethyleneglycol-bis-(beta-aminoethyl ether) N,N,N',N'-tetaacetic acid (EGTA), 2,3-dimercaptopropanel-1-sulfonic acid (DMPS), and 2,3-dimercaptosuccinic acid (DMSA), and the like.

Metal chelation complex: A complex containing a metal bound to a chelating agent.

Immunoglobulin product: A polypeptide, protein or multimeric protein containing at least the immunologically active portion of an immunoglobulin heavy chain and is thus capable of specifically combining with an antigen. Exemplary immunoglobulin products are an immunoglobulin heavy chain, immunoglobulin molecules, substantially intact immunoglobulin molecules, any portion of an immunoglobulin that contains the paratope, including those portions known in the art as Fab fragments, Fab' fragment, $F(ab')_2$ fragment and Fv fragment.

Immunoglobulin molecule: A multimeric protein containing the immunologically active portions of an immunoglobulin heavy chain and immunoglobulin light chain covalently coupled together and capable of specifically combining with antigen.

Fab fragment: A multimeric protein consisting of the portion of an immunoglobulin molecule containing the immunologically active portions of an immunoglobulin heavy chain and an immunoglobulin light chain covalently coupled together and capable of specifically combining with antigen. Fab fragments are typically prepared by proteolytic digestion of substantially intact immunoglobulin molecules with papain using methods that are well known in the art. However, a Fab fragment may also be prepared by expressing in a suitable host cell the desired portions of immunoglobulin heavy chain and immunoglobulin light chain using methods well known in the art.

$F_v$ fragment: A multimeric protein consisting of the immunologically active portions of an immunoglobulin heavy chain variable region and an immunoglobulin light chain variable region covalently coupled together and capable of specifically combining with antigen. Fv fragments are typically prepared by expressing in suitable host cell the desired portions of immunoglobulin heavy chain variable region and immunoglobulin light chain variable region using methods well known in the art.

Asexual propagation: Producing progeny by regenerating an entire plant from leaf cuttings, stem cuttings, root cuttings, single plant cells (protoplasts) and callus.

Glycosylated core portion: The pentasaccharide core common to all asparagine-linked oligosaccharides. The pentasaccharide care has the structure Man$\alpha$1-3 (man$\alpha$1-6) Man$\beta$1-46LcNAc$\beta$1-4 6LcNac-(ASN amino acid). The pentasaccharide core typically has 2 outer branches linked to the pentasaccharide core.

N-acetylglucosamine containing outer branches: The additional oligosaccharides that are linked to the pentasaccharide core (glycosylated core portion) of asparaginelinked oligosaccharides. The outer branches found on both mammalian and plant glycopolypeptides contain N-acetylglucosamine in direct contrast with yeast outer branches that only contain mannose. Mammalian outer branches have sialic acid residues linked directly to the terminal portion of the outer branch.

Glycopolypeptide multimer: A globular protein containing a glycosylated polypeptide or protein chain and at least one other polypeptide or protein chain bonded to each other to form a single globular protein. Both heterodimeric and homodimeric glycoproteins are multimeric proteins. Glycosylated polypeptides and proteins are n-glycans in which the C(1) of N-acetylglucosamine is linked to the amide group of asparagine.

Immunoglobulin superfamily molecule: A molecule that has a domain size and amino acid residue sequence that is significantly similar to immunoglobulin or immunoglobulin related domains. The significance of similarity is determined statistically using a computer program such as the Align program described by Dayhoff et al., *Meth Enzymol.* 91: 524–545 (1983). A typical Align score of less than 3 indicates that the molecule being tested is a member of the immunoglobulin gene superfamily.

The immunoglobulin gene superfamily contains several major classes of molecules including those shown in Table A and described by Williams and Barclay, in *Immunoglobulin Genes*, p361, Academic Press, New York, N.Y. (1989).

TABLE A

The Known Members of The Immunoglobulin Gene Superfamily*

Immunoglobulin

Heavy chains (IgM)
Light chain kappa
Light chain lambda
T cell receptor (Tcr) complex Tcr α-chain
Tcr β chain
Tcr gamma chain
Tcr X-chain
CD3 gamma chain
CD3 δ-chain
CD3 ε-chain
Major histocompatibility complex (MHC) antigens Class I H-chain
$β_2$-microglobulin
Class II α
Class II β
$β_2$-m associated antigens TL H chain
Qa-2 H chain
CD1a H chain
T lymphocyte antigens CD2
CD4
CD7
CD8 chain I
CD8 Chain IId
CD28
CTLA4
Haemopoietic/endothelium antigens LFA-3
MRC OX-45
Brain/lymphoid antigens Thy-1
MRC OX-2
Immunoglobulin receptors Poly Ig R
Fc gamma 2b/gamma 1R
FcεRI(α)
Neural molecules Neural adhesion molecule (MCAM)
Myelin associated gp (MAG)
$P_0$ myelin protein
Tumor antigen Carcinoembryonic antigen (CEA)
Growth factor receptors Platelet-derived growth factor (PDGF) receptor
Colony stimulating factor-1 (CSF1) receptor
Non-cell surface molecules $α_1$ B-glycoprotein
Basement membrane link protein

*See Williams and Barclay, in Immunoglobin Genes, p 361, Academic Press, NY (1989); and Sequences of Proteins of Immunological Interest 4th ed., U.S. Dept. of Health and Human Serving (1987).

Catalytic site: The portion of a molecule that is capable of binding a reactant and improving the rate of a reaction. Catalytic sites may be present on polypeptides or proteins, enzymes, organics, organo-metal compounds, metals and the lice. A catalytic site may be made up of separate portions present on one or more polypeptide chains or compounds. These separate catalytic portions associate together to form a larger portion of a catalytic site. A catalytic site may be formed by a polypeptide or protein that is bonded to a metal.

Enzymatic site: The portion of a protein molecule that contains a catalytic site. Most enzymatic sites exhibit a very high selective substrate specificity. An enzymatic site may be comprised of two or more enzymatic site portions present on different segments of the same polypeptide chain. These enzymatic site portions are associated together to form a greater portion of an enzymatic site. A portion of an enzymatic site may also be a metal.

Self-pollination: The transfer of pollen from male flower parts to female flower parts on the same plant. This process typically produces seed. Cross-pollination: The transfer of pollen from the male flower parts of one plant to the female flower parts of another plant. This process typically produces seed from which viable progeny can be grown.

Epitope: A portion of a molecule that is specifically recognized by an immunoglobulin product It is also referred to as the determinant or antigenic determinant.

Abzyme: An immunoglobulin molecule capable of acting as an enzyme or a catalyst.

Enzyme: A protein, polypeptide, peptide RNA molecule, or multimeric protein capable of accelerating or producing by catalytic action some change in a substrate for which it is often specific.

B. Methods of Producing Transgenic Plants Containing A Multimeric Protein

The present invention provides a novel method for producing a plant containing a multimeric protein comprised of first and second polypeptides. Generally, the method combines the following elements:

1. Inserting into the genome of a first member of a plant species a gene coding for a first polypeptide to produce a first transformant
2. Inserting into the genome of a second member of a plant species a gene coding for a second polypeptide to produce a second transformant
3. Producing a population of progeny from the fist and second transformants.
4. Isolating from the population, a progeny having the multimeric protein.

A plant produced by the present invention contains a multimeric protein comprised of a first and second polypeptides associated together in such a way as to assume a biologically functional conformation. In one embodiment of this invention, the multimeric protein is a ligand binding polypeptide (receptor) that forms a ligand binding site which specifically binds to a preselected ligand to form a complex having a sufficiently strong binding between the ligand and the ligand binding site for the complex to be isolated. In another embodiment, the multimeric protein is an immunoglobulin molecule comprised of an immunoglobulin heavy chain and an immunoglobulin light chain. The immunoglobulin heavy and light chains are associated with each other and assume a conformation having an antigen binding site specific for, as evidenced by its ability to be competitively inhibited, a preselected or predetermined antigen. When the multimeric protein is an antigen binding protein its affinity or avidity is generally greater than $10^5$ $M^{-1}$ or usually greater than $10^6$ M-1, and preferably greater than $10^8$ $M^{-1}$.

In a further embodiment, the multimeric protein is a Fab fragment consisting of a portion of an immunoglobulin heavy chain and a portion of an immunoglobulin light chain.

The immunoglobulin heavy and light chains are associated with each other and assume a conformation having an antigen binding site specific for a preselected or predetermined antigen. The antigen binding site on a Fab fragment has a binding affinity or avidity similar to the antigen binding site on an immunoglobulin molecule.

In yet another embodiment, the present transgenic plant contains a multimeric protein that is a $F_v$ fragment comprised of at least a portion of an immunoglobulin heavy chain variable region and at least a portion of an immunoglobulin light chain variable region. The immunoglobulin heavy and light chain variable regions autogenously associate with each other within the plant cell to assume a biologically active conformation having a binding site specific for a preselected or predetermined antigen. The antigen binding site on the $F_v$ fragment has an affinity or avidity for its antigen similar to the affinity displayed by the antigen binding site present on an immunoglobulin molecule.

In still another embodiment, the multimeric protein is an enzyme that binds a substrate and catalyzes the formation of a product from the substrate. While the topology of the substrate binding site (ligand binding site) of the catalytic multimeric protein is probably more important for its activity than affinity (association constant or pKa) for the substrate, the subject multimeric protein has an association constant for its preselected substrate greater than $10^3 \mu M^{-1}$, more usually greater than $10^5 M^{-1}$ or $10^6 M^{-1}$ and preferably greater than $10^7 M^{-1}$.

When the multimeric protein produced in accordance with the present invention is an abzyme comprised of at least a portion of the immunoglobulin heavy chain variable region in association with another polypeptide chain, this other polypeptide chain includes at least the biologically active portion of an immunoglobulin light chain variable region. Together, these two polypeptides assume a conformation having a binding affinity or association constant for a preselected ligand that is different, preferably higher, than the affinity or association constant of either of the polypeptides alone, i.e., as monomers. Useful multimeric proteins contain one or both polypeptide chains derived from the variable region of the light and heavy chains of an immunoglobulin. Typically, polypeptides comprising the light (VL) and heavy (VH) variable regions are employed together for binding the preselected antigen.

1. Inserting Genes Coding for a First Polypeptide into a First Member of a Plant Species Methods for isolating a gene coding for a desired first polypeptide are well known in the art. See, for example, Guide To Molecular Cloning Techniques in Methods In Enzymology. Volume 152, Berger and Kimmel, eds. (1987); and *Current Protocols in Molecular Biology*, Ausubel et al., eds., John Wiley and Sons, New York (1987) whose disclosures are herein incorporated by reference.

Genes useful in practicing this invention include genes coding for a polypeptide contained in immunoglobulin products, immunoglobulin molecules, Fab fragments, $F_v$ fragments, enzymes, receptors and abzymes. Particularly preferred are genes coding for immunoglobulin heavy and light chain variable regions. Typically, the genes coding for the immunoglobulin heavy chain variable region and immunoglobulin light chain variable region of an immunoglobulin capable of binding a preselected antigen are used. These genes are isolated from cells obtained from a vertebrate, preferably a mammal which has been immunized with an antigenic ligand (antigen) against which activity is sought, i.e., a preselected antigen. The immunization can be carried out conventionally and antibody titer in the animal can be monitored to determine the stage of immunization desired, which corresponds to the affinity or avidity desired. Partially immunized animals typically receive only one immunization and cells are collected therefrom shortly after a response is detected. Fully immunized animals display a peak titer which is achieved with one or more repeated injections of the antigen into the host mammal, normally at two to three week intervals.

Usually three to five days after the last challenge, the spleen is removed and the genes coding for immunoglobulin heavy and immunoglobulin light chain are isolated from the rearranged B cells present in the spleen using standard procedures. See *Current Protocols in Molecular Biology*, Ausubel et al., eds., John Wiley and Sons, New York (1987) and *Antibodies: A Laboratory Manual*, Harlowe and Lane, eds., Cold Spring Harbor, N.Y. (1983).

Genes coding for VH and VL polypeptides can be derived from cells producing IgA, IgD, IgE, IgG or IgM, most preferably from IgM and IgG, producing cells. Methods for preparing fragments of genomic DNA from which immunoglobulin variable region genes can be cloned are well known in the art. See for example, Herrmann et al., *Methods in Enzymol.* 152: 180–183 (1987); Frischauf, *Methods in Enzymol.* 152: 183–190 (1987); Frischauf, *Methods in Enzymol.* 152: 199–212 (1987). (The teachings of the references cited herein are hereby incorporated by reference).

Probes useful for isolating the genes coding for immunoglobulin products include the sequences coding for the constant portion of the $V_H$ and $V_L$ sequences coding for the framework regions of $V_H$ and $V_L$ and probes for the constant region of the entire rearranged immunoglobulin gene, these sequences being obtainable from available sources. See for example, Early and Hood, *Genetic Engineering*, Setlow and Hollaender eds., Vol. 3: 157–138, Plenum Publishing Corporation, New York (1981); and Kabat et al., *Sequences of Immunological Interests*, National Institutes of Health, Bethesda, Md. (1987).

Genes coding for a polypeptide subunit of a multimeric protein can be isolated from either the genomic DNA containing the gene expressing the polypeptide or the messenger RNA (mRNA) which codes for the polypeptide. The difficulty in using genomic DNA is in juxtaposing the sequences coding for the polypeptide where the sequences are separated by introns. The DNA fragment(s) containing the proper exons must be isolated, the introns excised, and the exons spliced together in the proper order and orientation. For the most part, this will be difficult so the alternative technique employing mRNA will be the method of choice because the sequence is contiguous (free of introns) for the entire polypeptide. Methods for isolating mRNA coding for peptides or proteins are well known in the art See, for example, *Current Protocols in Molecular Biology*, Ausubel et al., John Wiley and Sons, New York (1987), *Guide to Molecular Cloning Techniques*, in *Methods In Enzymology*, Volume 152, Berger and Kimmel, eds. (1987), and *Molecular Cloning: A Laboratory Manual*, Maniatis et al., eds., Cold Spring Harbor Laboratory, Cold Spring Harbor, N.Y. (1982).

The polypeptide coding genes isolated above are typically operatively linked to an expression vector. Expression vectors compatible with the host cells, preferably those E 15 compatible with plant cells are used to express the genes of the present invention. Typical expression vectors useful for expression of genes in plants are well known in the art and include vectors derived from the tumor-inducing (Ti) plasmid of *Agrobacterium tumefaciens* described by Rogers et al., *Meth. in Enzymol.* 153: 253–277 (1987).

However, several other expression vector systems are known to function in plants. See for example, Verma et al., PCT Publication No. WO87/00551; and Cocking and Davey, Science, 236: 1259–1262 (1987).

The expression vectors described above contain expression control elements including the promoter. The polypeptide coding genes are operatively linked to the expression vector to allow the promoter sequence to direct RNA polymerase binding and synthesis of the desired polypeptide coding gene. Useful in expressing the polypeptide coding gene are promoters which are inducible, viral, synthetic, constitutive, temporally regulated, spatially regulated, and spatiotemporally regulated. The choice of which expression vector and ultimately to which promoter a polypeptide coding gene is operatively linked depends directly, as is well known in the art, on the functional properties desired, e.g. the location and timing of protein expression, and the host cell to be transformed, these being limitations inherent in the art of constructing recombinant DNA molecules. However, an expression vector useful in practicing the present invention is at least capable of directing the replication, and preferably also the expression of the polypeptide coding gene included in the DNA segment to which it is operatively linked.

In preferred embodiments, the expression vector used to express the polypeptide coding gene includes a selection marker that is effective in a plant cell preferably a drug resistance selection marker. A preferred drug resistance marker is the gene whose expression results in kanamycin resistance, i.e., the chimeric gene containing the nopaline synthase promoter, Tn5 neomycin phosphotransferase II and nopaline synthase 3' nontranslated region described by Rogers et al., in *Methods For Plant Molecular Biology*, a Weissbach and H. Weissbach, eds., Academic Press Inc., San Diego, Calif. (1988). A useful plant expression vector is commercially available from Pharmacia, Piscataway, N.J.

A variety of methods have been developed to operatively link DNA to vectors via complementary cohesive termini. For instance, complementary homopolymer tracks can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteria phage T4 DNA ligase. Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass.

Methods for introducing polypeptide coding genes into plants include *Agrobacterium*-mediated plant transformation, protoplast transformation, gene transfer into pollen, injection into reproductive organs and injection into immature embryos. Each of these methods has distinct advantages and disadvantages. Thus, one particular method of introducing genes into a particular plant species may not necessarily be the most effective for another plant species.

*Agrobacterium tumefaciens*-mediated transfer is a widely applicable system for introducing genes into plant cells because the DNA can be introduced into whole plant tissues, bypassing the need for regeneration of an intact plant from a protoplast. The use of *Agrobacterium*-mediated expression vectors to introduce DNA into plant cells is well known in the art. See, for example, the methods described by Fraley et al., *Biotechnology*. 3: 629 (1985) and Rogers et al., *Methods in Enzymology*. 153: 253–277 (1987). Further, the integration of the Ti-DNA is a relatively precise process resulting in few rearrangements. The region of DNA to be transferred is defined by the border sequences and intervening DNA is usually inserted into the plant genome as described by Spielmann et al., *Mol. Gen. Genet*. 205: 34 (1986) and Jorgensen et al., *Mol. Gen. Genet*. 207: 471 (1987). Modern *Agrobacterium* transformation vectors are capable of replication in *Escherichia coli* as well as *Agrobacterium*, allowing for convenient manipulations as described by Klee et al., in *Plant DNA Infectious Agents*, T. Hohn and J. Schell, eds., Springer-Verlag, New York (1985) pp. 179–203. Further recent technological advances in vectors for *Agrobacterium*-mediated gene transfer have improved the arrangement of genes and restriction sites in the vectors to facilitate construction of vectors capable of expressing various polypeptide coding genes. The vectors described by Rogers et al., *Methods in Enzymology*, 153: 253 (1987), have convenient multi-linker regions flanked by a promoter and a polyadenylation site for direct expression of inserted polypeptide coding genes and are suitable for present purposes.

In those plant species where *Agrobacterium*-mediated transformation is efficient, it is the method of choice because of the facile and defined nature of the gene transfer. However, few monocots appear to be natural hosts for *Agrobacterium*, although transgenic plants have been produced in asparagus using *Agrobacterium* vectors as described by Bytebier et al., *Proc. Natl. Acad. Sci. U.S.A.*, 84: 5345 (1987). Therefore, commercially important cereal grains such as rice, corn, and wheat must be transformed using alternative methods. Transformation of plant protoplasts can be achieved using methods based on calcium phosphate precipitation, polyethylene glycol treatment, electroporation, and combinations of these treatments. See, for example, Potrykus et al., *Mol. Gen. Genet*. 199: 183 (1985); Lorz et al., *Mol. Gen. Genet.*, 199: 178 (1985); Fromm et al., *Nature*, 319: 791 (1986); Uchimiya et al., *Mol. Gen. Genet*. 204: 204 (1986); Callis et al., *Genes and Development* 1: 1183 (1987); and Marcotte et al., *Nature*, 335: 454 (1988).

Application of these systems to different plant species depends upon the ability to regenerate that particular plant species from protoplasts. Illustrative methods for the regeneration of cereals from protoplasts are described in Fujimura et al., *Plant Tissue Culture Letters*, 2: 74 (1985); Toriyama et al., *Theor Appl. Genet.*, 73: 16 (1986); Yamada et al., *Plant Cell Rep*. 4: 85 (1986); Abdullah et al., *Biotechnology*, 4: 1087 (1986).

*Agrobacterium*-mediated transformation of leaf disks and other tissues appears to be limited to plant species that *Agrobacterium tumefaciens* naturally infects. Thus, *Agrobacterium*-mediated transformation is most efficient in dicotyledonous plants. However, the transformation of Asparagus using *Agrobacterium* can also be achieved. See, for example, Bytebier, et al., *Proc. Natl. Acad. Sci*. 84: 5345 (1987).

To transform plant species that cannot be successfully regenerated from protoplast, other ways to introduce DNA into intact cells or tissues can be utilized. For example, regeneration of cereals from immature embryos or explants can be effected as described by Dasil, *Biotechnology,* 6: 397 (1988). In addition, "particle gun" or high-velocity microprojectile technology can be utilized as well. Using such technology, DNA is carried through the cell wall and into the cytoplasm on the surface of small (0.525 μm) metal particles that have been accelerated to speeds of one to several hundred meters per second as described in Klein et al., *Nature.* 327: 70 (1987); Klein et al., *Proc. Natl. Acad. Sci. U.S.A.* 85: 8502 (1988); and McCabe et al., *Biotechnology* 6: 923 (1988). The metal particles penetrate through several layers of cells and thus allow the transformation of cells within tissue explants. Metal particles have been used to successfully transform corn cells and to produce fertile, stably transformed tobacco and soybean plants. Transformation of tissue explants eliminates the need for passage through a protoplast stage and thus speeds the production of transgenic plants.

DNA can be introduced into plants also by direct DNA transfer into pollen as described by Zhou et al., *Methods in Enzmmology.* 101: 433 (1983); D. Hess, *Intern Rev. Cytol.* 107: 367 (1987); Luo et al., *Plant Mol. Biol. Reporter.* 6: 165 (1988). Expression of polypeptide coding genes can be obtained by injection of the DNA into reproductive organs of a plant as described by Pena et al., *Nature,* 325: 274 (1987). DNA can also be injected directly into the cells of immature embryos and the rehydration of desiccated embryos as described by Neuhaus et al, *Theor. Appl. Genet.* 75: 30 (1987); and Benbrook et al., in *Proceedings Bio Expo* 1986, Butterworth, Stoneham, Mass., pp. 27–54 (1986).

The regeneration of plants from either single, plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil.

The regeneration of plants containing the foreign gene introduced by *Agrobacterium* tumefaciens from leaf explants can be achieved as described by Horsch et al., *Science,* 227: 1229–1231 (1985). In this procedure, transformants are grown in the presence of a selection agent and in a medium that induces the regeneration of shoots in the plant species being transformed as described by Fraley et al., *Proc. Nat. Acad. Sci. U.S.A.,* 80: 4803 (1983). This procedure typically produces shoots within two to four weeks and these transformant shoots are then transferred to an appropriate root-inducing medium containing the selective agent and an antibiotic to prevent bacterial growth. Transformant shoots that rooted in the presence of the selective agent to form plantlets are then transplanted to soil to allow the production of roots. These procedures will vary depending upon the particular plant species employed, such variations being well known in the art.

2. Inserting a Gene Coding for a Second Polypeptide into a Second Member of a Plant Species Useful genes include those genes coding for a second polypeptide that can autogenously associate with the first polypeptide in such a way as to form a biologically functional multimeric protein. The methods used to introduce a gene coding for this second polypeptide into a second member of a plant species are the same as the methods used to introduce a gene into the first member of the same plant species and have been described above.

3. Producing a Population of Progeny from the First and Second Transformants

A population of progeny can be produced from the first and second transformants of a plant species by methods well known in the art including those methods known as cross fertilization described by Mendel in 1865 (an English translation of Mendel's original paper together with comments and a bibliography of Mendel by others can be found in Experiments In Plant Hybridization. Edinburgh, Scotland, Oliver Boyd, eds., 1965).

4. Isolating Progeny Containing the Multimeric Protein

Progeny containing the desired multimeric protein can be identified by assaying for the presence of the biologically multimeric protein using assay methods well known in the art. Such methods include Western blotting, immunoassays, binding assays, and any assay designed to detect a biologically functional multimeric protein. See, for example, the assays described in Immunology: The Science of Self-Nonself Discrimination, Klein, John Wiley and Sons, New York, N.Y. (1982).

Preferred screening assays are those where the biologically active site on the multimeric protein is detected in such a way as to produce a detectible signal. This signal may be produced directly or indirectly and such signals include, for example, the production of a complex, formation of a catalytic reaction product, the release or uptake of energy, and the like. For example, a progeny containing an antibody molecule produced by this method may be processed in such a way to allow that antibody to bind its antigen in a standard immunoassay such as an ELISA or a radio-immunoassay similar to the immunoassays described in *Antibodies: A Laboratory Manual*, Harlow and Lane, eds., Cold Spring Harbor Laboratory, Cold Spring Harbor, N.Y. (1988).

A further aspect of the present invention is a method of producing a multimeric protein comprised of a first and a second polypeptide. Generally, the method combines the elements of cultivating a plant of the present invention, and harvesting the plant that was cultivated to produce the desired multimeric protein.

A plant of the present invention containing the desired multimeric protein comprised of a first polypeptide and a second polypeptide is cultivated using methods well known to one skilled in the art. Any of the transgenic plants of the present invention may be cultivated to isolate the desired multimeric protein they contain.

After cultivation, the transgenic plant is harvested to recover the produced multimeric protein. This harvesting step may consist of harvesting the entire plant, or only the leaves, or roots of the plant. This step may either kill the plant or if only the portion of the transgenic plant is harvested may allow the remainder of the plant to continue to grow.

In preferred embodiments this harvesting step further comprises the steps of:
   (i) homogenizing at least a portion of said transgenic plant to produce a plant pulp;
   (ii) extracting said multimeric protein from said plant pulp to produce a multimeric protein containing solution; and
   (iii) isolating said multimeric protein from said solution.

At least a portion of the transgenic plant is homogenized to produce a plant pulp using methods well known to one skilled in the art. This homogenization may be done manually, by a machine, or by a chemical means as long as the transgenic plant portions are broken up into small pieces to produce a plant pulp. This plant pulp consists of a mixture of varying sizes of transgenic plant particles. The size of the plant particles and the amount of variation in size that can be tolerated will depend on the exact method used to extract the multimeric protein from the plant pulp and these parameters are well known to one skilled in the art.

The multimeric protein is extracted from the plant pulp produced above to form a multimeric protein containing solution. Such extraction processes are common and well known to one skilled in this art. For example, the extracting step may consist of soaking or immersing the plant pulp in a suitable solvent. This suitable solvent is capable of dissolving the multimeric protein present in the plant pulp to produce a multimeric protein containing solution. Solvents useful for such an extraction process are well known to those skilled in the art and include aqueous solvents, organic solvents and combinations of both.

The multimeric protein is isolated from the solution produced above using methods that are well known to those skilled in the art of protein isolation. These methods include, but are not limited to, immuno-affinity purification and purification procedures based on the specific size, electrophoretic mobility, biological activity, and/or net charge of the multimeric protein to be isolated.

C. Utilization of the Transgenic Plant

The present invention also provides a novel method for separating a preselected ligand from a fluid sample. The method combines the following elements:

1. Commingling the fluid sample with plant cells from a transgenic plant from the present invention to form an admire.
2. Maintaining this admixture for a time period sufficient for the ligand to enter the plant cells and bind the multimeric protein to form a complex within the plant cells.
3. Removing the complex-containing plant cells from the admixture and thereby separating the ligand from the fluid sample.

The fluid sample is commingled with the plant cells from a transgenic plant of the present invention that contain a multimeric protein. This multimeric protein can be a receptor, an enzyme, an immunoglobulin product, an immunoglobulin molecule or fragment thereof, or an abzyme. One skilled in the art will understand that this multimeric protein must be capable of binding the preselected ligand. The fluid sample can be a liquid or a gas. In either case the commingling may consist of placing the plant cells in either the liquid or the gas. Alternatively, the plant cells may be thoroughly mixed with the fluid sample. This commingling must bring the fluid sample in intimate contact with the plant cells to form an admixture.

This admixture is maintained for a time period sufficient to allow the ligand present in the fluid sample to enter the cells. This process may be a passive process as in diffusion or may occur through the application of energy to the system, such as applying high pressure to the fluid sample to force it into the plant cells. The amount of time required for the ligand to enter the plant cells is known to one skilled in the art and can be predetermined to optimize such time period. After entering the plant cells the ligand binds the multimeric protein to form a complex. When the multimeric protein is a receptor, the complex formed is a receptor-ligand complex. When the multimeric protein is an immunoglobulin, immunoglobulin molecule, a portion of an immunoglobulin molecule, a Fab fragment, or a Fv fragment the complex formed is an immuno-reaction complex. When the multimeric protein is an enzyme and the ligand is a substrate the complex formed is an enzyme-substrate complex. When the multimeric protein is an abzyme the complex formed is an immuno-reaction complex.

After the complex is formed in the plant cells, the complex-containing plant cells are removed from the admixture thereby separating the ligand from the fluid sample. Methods for removing the plant cells from the admixtures are well known to those skilled in the art and include mechanical removal, filtration, sedimentation and other separation means.

When the plant cells utilized for this method constitute a viable plant, this expedient concentrates the ligand within the plant. When the ligand is an important nutrient, this results in that plant concentrating that particular nutrient within its cells, thereby enhancing the nutritional value of the plant. When the ligand is an environmental pollutant, this pollutant is concentrated within the plant cells and thus is removed from the environment. Of course, for this method to be applicable, the ligand must be able to enter the plant cells. The ligands that can enter the plant cells are well known to those skilled in the art.

The present invention also contemplates a method of separating a metal ion from a fluid sample containing the metal ion. This particular method includes the following steps:

1. Admixing to the fluid sample a chelating agent to form a chelating admixture.
2. Maintaining the chelating admixture for a time period sufficient for the metal ion to bind the chelating agent and form a metal ion chelation complex.
3. Commingling the metal ion chelation complex with plant cells of the present invention to form a binding admixture.
4. Maintaining the binding admixture for a time period sufficient for the metal ion chelation complex to enter the plant cells and bind the multimeric protein to form a reaction complex.
5. Removing the reaction complex-containing plant cells from the binding admixture and thereby separating the metal ion from the fluid sample.

Chelating agents useful in practicing this method include ethylene diamine tetraacetic acid (EDTA) and Bis(bis-carboxy methyl amino propyl) phenyl isothiocyanate (CITC). See for example, Meares, et al., *Analytical Biochemistry* 142: 68–78 (1984). The fluid sample may be either a gas or liquid sample and, when admixed with a chelating agent, forms a chelating admixture.

The chelating admixture is maintained for a time period sufficient for the metal to bind the chelating agent and form a metal ion chelation complex. The amount of time required for the metal ion to bind the chelating agent will depend upon at least the type of chelating agent employed and the concentration of the metal. The metal ion chelation complex is formed when at least one metal ion associates with its chelating agent and becomes bound to that chelating agent to form a complex.

This metal ion chelation complex is commingled with plant cells of the present invention. These plant cells contain a multimeric protein capable of specifically binding the metal ion chelation complex. For example, the plant cells may contain an immunoglobulin that is immunospecific for a metal chelation complex similar to those immunoglobulin molecules described by Reardon, et al., *Nature.* 316: 265–268 (1985) and Meares, et al., *Analytical Biochemistry,* 142: 68–78 (1984).

The binding admixture is maintained for a time period sufficient for the metal ion chelation complex to enter the plant cells and bind the multimeric protein to form a reaction complex with the plant cells. The binding admixture must be maintained under conditions allow the metal ion chelation complex to bind the multimeric protein. Such conditions are well known to those skilled in the art. The amount of time required for the metal ion chelation complex to enter the plant cell will vary and will depend at least upon the concentration and size of the metal chelation complex. The metal ion chelation complex may enter the plant cells passively, for example by diffusion, or may be forced under pressure into the plant cells. The reaction complex formed when the metal ion chelation complex binds to the multimeric protein present in the plant cells consists of the metal ion bound to the chelating agent, the chelating agent and the multimeric protein. The reaction complex-containing plant cells are then removed from the binding admixture thereby separating the metal ion from the fluid sample. The plant cells may be removed using the methods well known to those skilled in the art and include mechanically removing, filtration, sedimentation and other separation means. When the plant cells utilized for this method constitute a viable plant, this method concentrates the metal within the plant.

Transgenic plants of the present invention can be produced from any sexually crossable plant species that can be transformed using any method known to those skilled in the art. Useful plant species are dicotyledons including tobacco, tomato, the legumes, alfalfa, oaks, and maples, monocotyledons including grasses, corn, grains, oats, wheat, and barley; and lower plants including gymnosperms, conifers, horsetails, club mosses, liver warts, horn warts, mosses, algae, gametophytes, sporophytes of pteridophytes.

The transgenic plants of the present invention contain polypeptide coding genes operatively linked to a promoter. Useful promoters are known to those skilled in the art and include inducible promoters, viral promoters, synthetic promoters, constitutive promoters, temporally regulated promoters, spatially regulated promoters, and spatiotemporally regulated promoters.

In preferred embodiments, the transgenic plants of the present invention contain an immunoglobulin product. Useful immunoglobulin products are well known to one skilled in the immunoglobulin art and include an immunoglobulin heavy chain, an immunoglobulin molecule comprised of a heavy and a light chain. One half of an immunoglobulin molecule, a Fab fragment, a Fv fragment, and proteins known as single chain antigen binding proteins. The structures of immunoglobulin products are well known to those skilled in the art and described in *Basic and Clinical Immunology*, by Stites, et al., 4th ed, Lange Medical Publications, Los Altos, Calif. The structure of single chain antigen binding proteins has been described by Bird et al., *Science*. 242: 423–426 (1988) and U.S. Pat. No. 4,704,692 by Ladner.

The immunoglobulins, or antibody molecules, are a large family of molecules that include several types of molecules, such as IgD, IgG, IgA, IgM and IgE. The antibody molecule is typically comprised of two heavy (H) and light (L) chains with both a variable (V) and constant (C) region present on each chain. Several different regions of an immunoglobulin contain conserved sequences useful for isolating the immunoglobulin genes using the polymerase chain reaction. Extensive amino acid and nucleic acid sequence data displaying exemplary conserved sequences is compiled for immunoglobulin molecules by Kabat et al., in *Sequences of Proteins of Immunological Interest*, National Institute of Health, Bethesda, Md. (1987).

The V region of the H or L chain typically comprises four framework (FR) regions (FIG. 1) each containing relatively lower degrees of variability that includes lengths of conserved sequences. The use of conserved sequences from the FR1 and FR4 (J region) framework regions of the VH is a preferred exemplary embodiment and is described herein in the Examples. Framework regions are typically conserved across several or all immunoglobulin types and thus conserved sequences contained therein are particularly suited for isolating the variable types.

One particularly useful immunoglobulin product is an immunoglobulin heavy chain. An immunoglobulin heavy chain consists of an immunoglobulin heavy chain variable region and an immunoglobulin constant region. The immunoglobulin heavy chain variable region is a polypeptide containing an antigen binding site (and antibody combining site). Therefore, the immunoglobulin heavy chain variable region is capable of specifically binding a particular epitope. Preferably, the $V_H$ will be from about 110 to about 125 amino acid residues in length. The amino acid residue sequence will vary widely, depending the particular antigen the $V_H$ is capable of binding. Usually, there will be at least two cysteines separated by about 60–75 amino acid residues that are joined to one another by a disulfide bond.

The immunoglobulin constant region (CH) can be of the alpha, gamma 1, gamma 2, gamma 3, delta, mu, or epsilon human isotypes. If the immunoglobulin heavy chain is derived from a mouse the $C_H$ may be of the alpha, gamma 1, gamma 2a, gamma 2b, gamma 3, delta, mu, or epsilon isotypes. The $C_H$ will be of an isotype that is normally present in the animal species that it was isolated from. The $C_H$ may also consist of domains derived from different isotypes to enhance or confer a given biological function. Genes containing the DNA sequence from several different constant region isotypes may be combined to produce a chimeric gene that encodes a chimeric $C_H$ polypeptide. The DNA and protein sequences are easily obtained from available sources. See for example, Early Hood, *Genetic Engineering*, Setlow and Hollaender, eds., Vol. 3, Plenum Publishing Corporation, (1981), pages 157–188; and Kabat, et al., *Sequences of Immunological Interest*, National Institutes Of Health, Bethesda, Md. (1987). These two sources also contain a number of sequences for $V_H$, $V_L$ and $C_L$ genes and proteins.

Preferred immunoglobulin products are those that contain an immunoglobulin heavy chain described above and an immunoglobulin light chain. Immunoglobulin light chains consist of an immunoglobulin light chain variable region ($V_L$) and an immunoglobulin light chain constant region. The $V_L$ will be from about 95 to about 115 amino acid residues in length. One skilled in the art will understand that there are two isotypes of CL that are present in both human and mouse, the lambda isotype and the kappa isotype.

In other preferred embodiments the immunoglobulins product consists of $V_H$ alone, or of a $V_H$ associated with a $V_L$ to form a Fv fragment.

The contemplated transgenic plants contain a multimeric protein. This multimeric protein may be an immunoglobulin product described above, an enzyme, a receptor capable of binding a specific ligand, or an abzyme.

An enzyme of the present invention is a multimeric protein wherein at least two polypeptide chains are present. These two polypeptide chains are encoded by genes introduced into the transgenic plant by the method of the present invention. Useful enzymes include aspartate transcarbamylase and the like.

In another preferred embodiment is a receptor capable of binding a specific ligand. Typically this receptor is made up of at least two polypeptide chains encoded by genes introduced into the transgenic plant by a method of the present invention. Examples of such receptors and their respective ligands include hemoglobin, $O_2$; protein kinases, cAMP; and the like.

In another preferred embodiment of the present invention the immunoglobulin product present is an abzyme constituted by either an immunoglobulin heavy chain and its associated variable region, or by an immunoglobulin heavy chain and an immunoglobulin light chain associated together to form an immunoglobulin molecule, a Fab, Fv or a substantial portion of an immunoglobulin molecule. Illustrative abzymes include those described by Tramontano et al., Science, 234: 1566–1570 (1986): Pollack et al., Science, 234: 1570–1573 (1986): Janda et al., Science, 241: 1188–1191 (1988); and Janda et at, Science 244: 437–440 (1989).

Typically a multimeric protein of the present invention contains at least two polypeptides; however, more than two peptides can also be present. Each of these polypeptides is encoded by a separate polypeptide coding gene. The polypeptides are associated with one another to form a multimeric protein by disulfide bridges, by hydrogen bonding, or like mechanisms.

Included as part of the present invention are transgenic plants that are produced from or are the progeny of a transgenic plant of the present invention. These transgenic plants contain the same multimeric protein as that contained in the parental transgenic plant. Such plants may be generated either by asexually propagating the parental plant or by self-pollination. The process of asexually propagating and self-pollinating a plant are well known.

In a further aspect, the present invention contemplates a transgenic plant that contains a complex. Generally, such a complex-conning transgenic plant is obtained by adding a chelating agent to a fluid sample to form a chelating admixture, maintaining the admixture for a time period sufficient for any metal present in the fluid sample to bind the chelating agent and form a metal chelation complex, commingling the metal chelation complex with transgenic plant cells of the present invention to form a binding admixture, and maintaining the binding admixture for a time period sufficient for the metal chelation complex to enter the plant cells and bind the multimeric protein present in the plant cells to form a complex within the plant cells.

Also contemplated by the present invention are transgenic plants containing a reaction complex consisting of a metal chelation complex and an immunoglobulin product. Typically, this transgenic plant will be produced by a method the present invention.

D. Biologically Active Glycopolypeptide Multimers

The present invention contemplates a biologically active glycopolypeptide multimer comprising at least two polypeptides, one of the polypeptides having (a) an immunoglobulin amino acid residue sequence, and (b) an oligosaccharide comprising a core portion and N-acetylglucosamine-containing outer branches, such that the multimer is free from sialic acid residues.

In preferred embodiments, the biologically active glycopolypeptide multimer includes an amino acid residue sequence of an immunoglobulin superfamily molecule, such as an amino acid residue sequence of an immunoglobulin, a molecule of the T cell receptor complex, a major histocompatibility complex antigen and the like. Particularly preferred are biologically active glycopolypeptide multimers that contain an amino acid residue sequence of an immunoglobulin heavy chain, an immunoglobulin heavy chain variable region or a portion of an immunoglobulin heavy chain variable region. Glycopolypeptide multimers having an amino acid residue sequence of an immunoglobulin light chain, and immunoglobulin light chain variable region and portions of an immunoglobulin light chain variable region are also preferred.

In a preferred embodiment, the biologically active glycopolypeptide multimer comprises a polypeptide having a glycosylated core portion as well as N-acetylglucosamine containing outer branches and an amino acid residue sequence of an immunoglobulin molecule that is bonded to at least one other polypeptide including another amino acid residue sequence. In preferred embodiments, the other polypeptide may include an amino acid residue sequence of an immunoglobulin superfamily molecule, an immunoglobulin molecule, an immunoglobulin heavy chain, an immunoglobulin heavy chain variable region, a portion of an immunoglobulin heavy chain variable region, an immunoglobulin light chain, an immunoglobulin light chain variable region, or a portion of an immunoglobulin light chain region.

In other preferred embodiments, the glycopolypeptide multimer further comprises immunoglobulin light chain bonded to the immunoglobulin molecule or a portion of the immunoglobulin molecule present in the glycopolypeptide multimer. J chain is a polypeptide that is associated with polymeric IgA and IgM and other immunoglobulins such as IgG, IgD, IgE, and the other various subclasses of these immunoglobulin isotypes.

The amino acid composition of both human and mouse J chain has been described by Mole et al., Biochemistry. 16: 3507 (1977), Max and Korsmeyer, J. Exp. Med., 161: 832 (1985), Cann et al., Proc. Natl. Acad. Sci. USA 79: 6656 (1982), and Koshland, Annu. Rev. Immunol. 3: 425 (1985). J chain has 137 amino acid residues with a high proportion of acidic amino acids, low numbers of glycine, threonine, cysteine, and only one methionine. The J chain contains 8 cysteine residues, 6 of which are involved in the formation of intrachain disulfide bonds and 2 are connected to the penultimate cysteine residues of the immunoglobulin heavy chain such as the alpha or mu heavy chain as described by Mendez et al., Biochem. Biophys. Res. Commun. 55: 1291 (1973), Mesteckey et al., Proc. Natl. Acad. Sci. USA. 71: 544 (1974), Mesteckey and Schrohenloher, Nature. 249: 650 (1974).

In preferred embodiments, the glycopolypeptide multimer also comprises a secretory component bonded to the Fc region of the immunoglobulin heavy chain amino acid residue sequence present in the glycopolypeptide multimer. Secretory component is comprised of a single polypeptide chain with 549 to 558 amino acid residues and large amounts of carbohydrates attached by N-glycosidic bonds to asparagine residues as 5–7 oligosaccharide side chains. See, Mostov et al., Nature. 308: 37 (1984); Eiffert et al., Hoppe Seyler's C. Physiol. Chem. 365: 1489 (1984); Heremans, N The Antigens. M. Sela ed., 2: 365, Academic Press New York (1974); Tomana et al., Ana. Biochem., 89: 110 (1978); Purkayasthaa et al., J. Biol. Chem. 254: 6583 (1979); and Mizoguchi et al., J. Biol. Chem. 257: 9612 (1982). Secretory component contains 20 cysteine residues that are involved in intrachain disulfide bonding. In preferred embodiments, secretory component is disulfide bonded to a cysteine residue present in the Fc region of the immunoglobulin heavy chain present in the glycopolypeptide multimer.

Figure 3A:
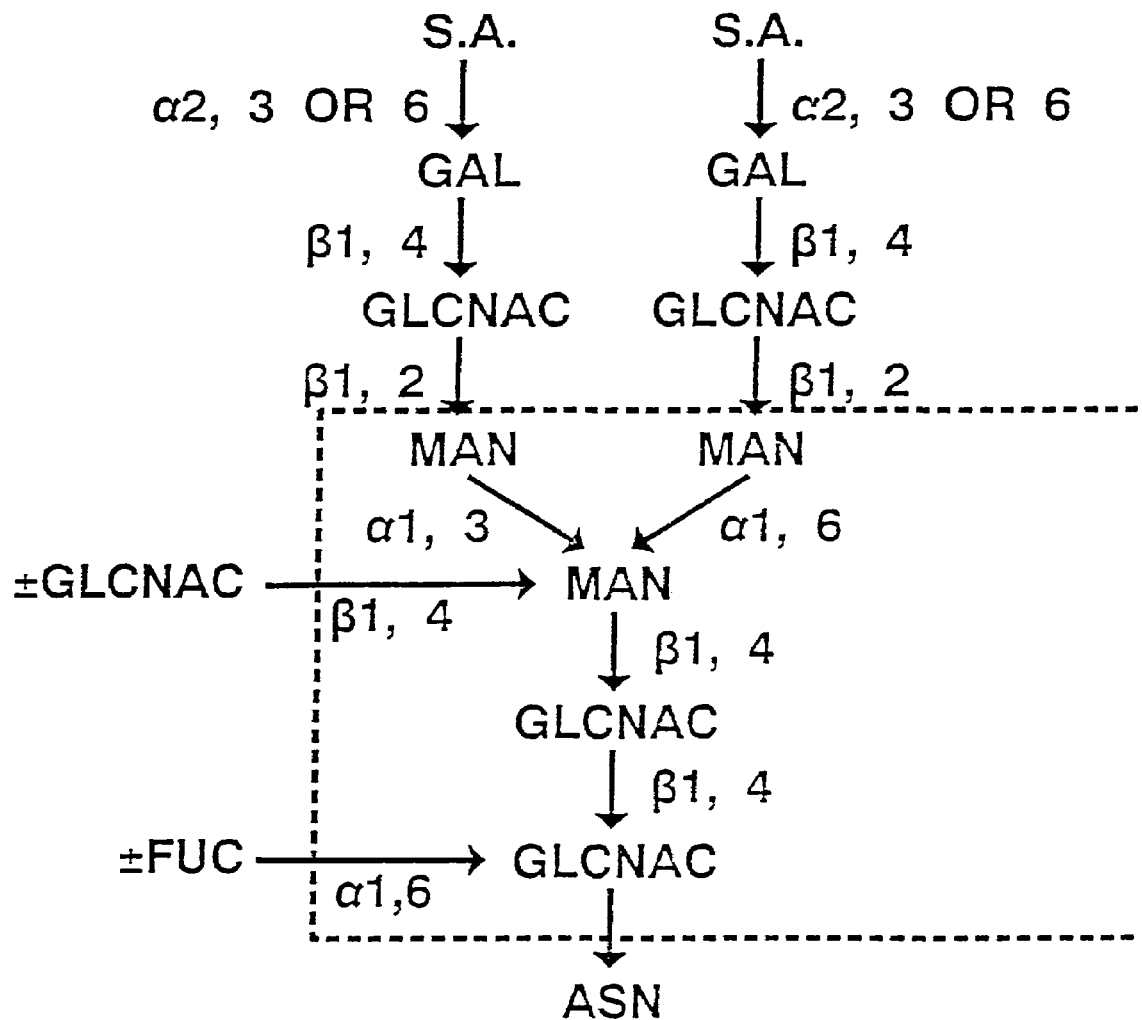
FIGS. 3A–3C illustrate the structures of the major types of asparagine-linked oligosaccharides (in-linked oligosaccharides). The boxed area encloses the pentasaccharide core (glycosylated core portions) common to all N-linked oligosaccharides. The complex (FIG. 3A) and hybrid (FIG. 3B) N-linked oligosaccharides have N-acetylglucosamine containing outer branches, and the high mannose (FIG. 3C)N-linked oligosaccharides do not.
Figure 3B:
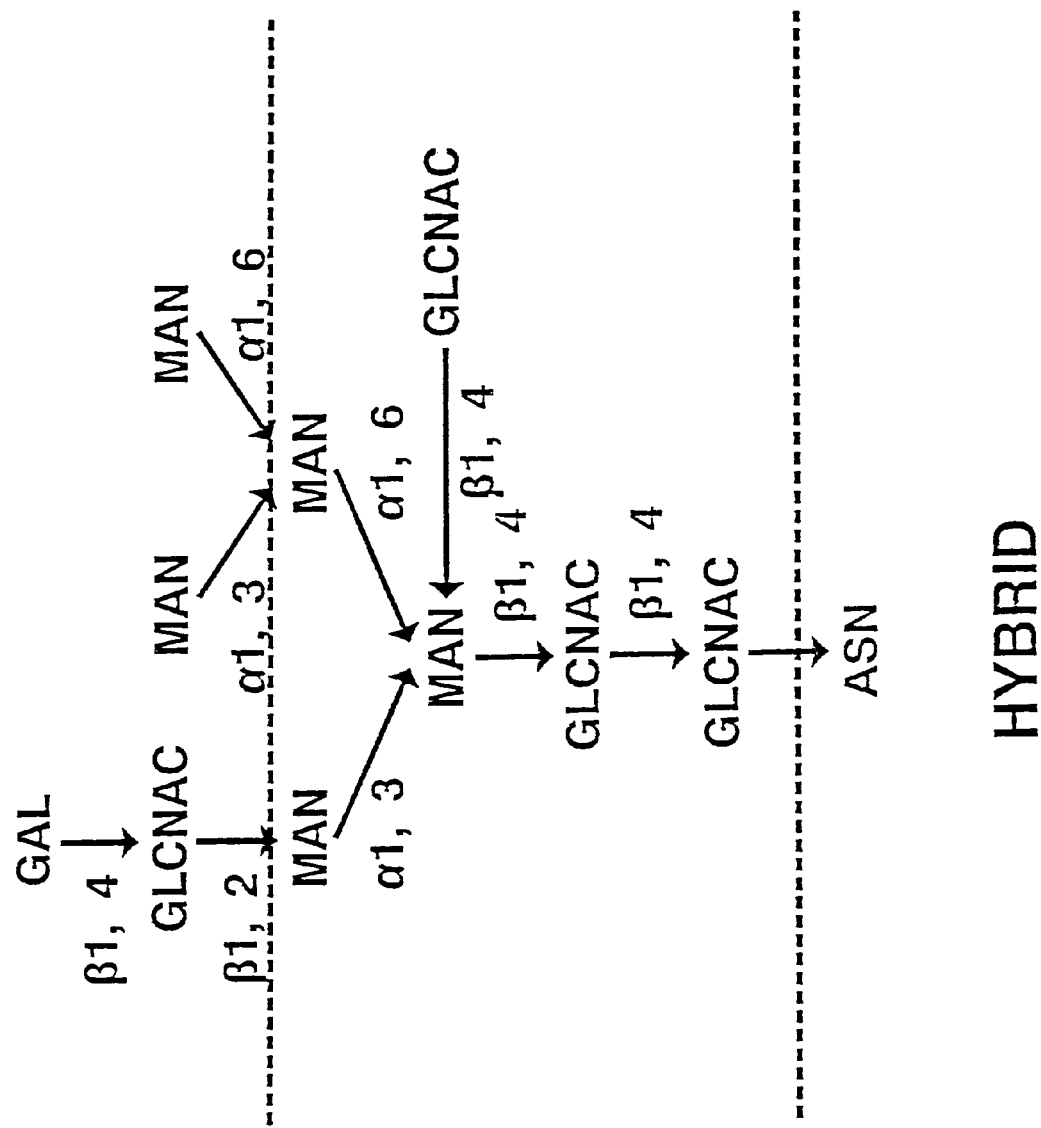
Figure 3C:
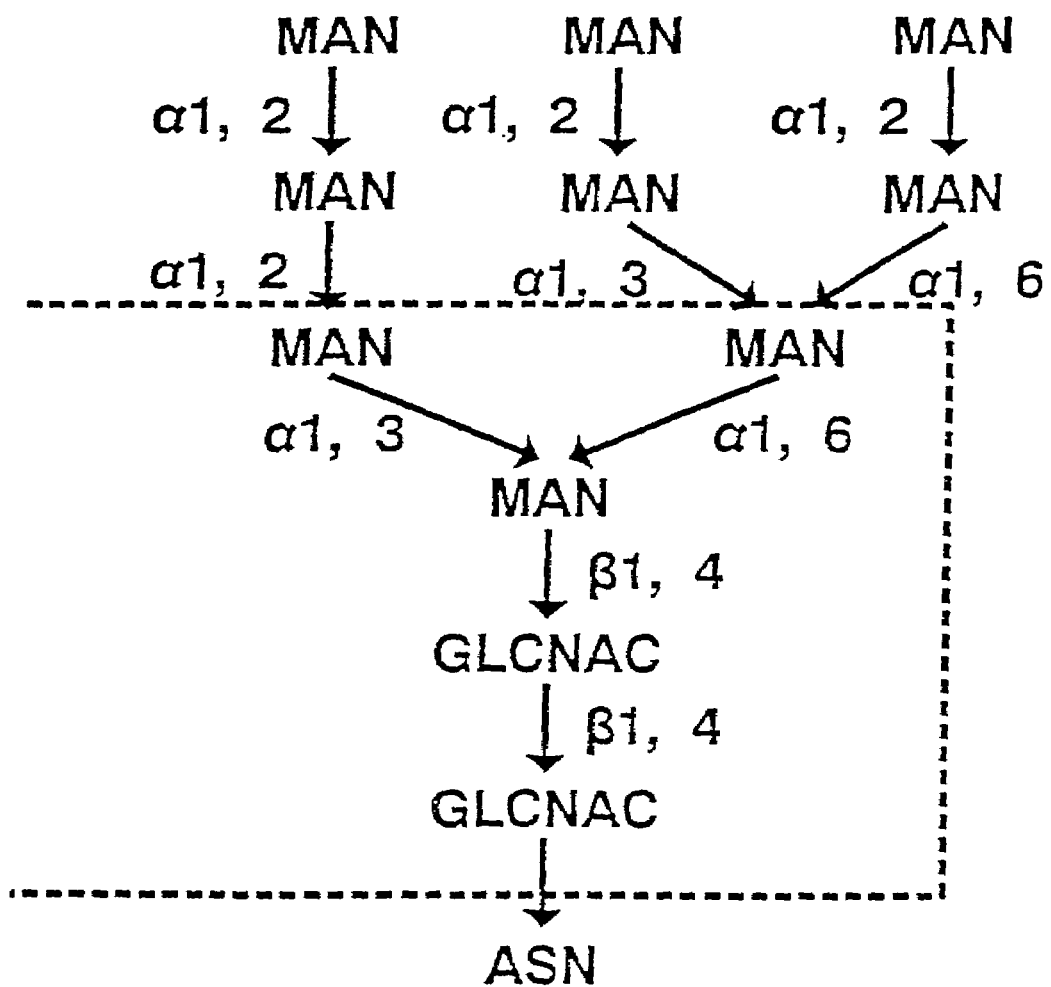

The present invention contemplates a glycopolypeptide multimer comprises a polypeptide having a glycosylated core portion as well as a N-acetylglucosamine containing outer branches and the multimer is free from detectable sialic acid residues. The polypeptide has a glycosylated core portion including an N-acetylglucosamine oligosaccharide bonded via its C(1) carbon directly to the amide group of an asparagine amino acid residue present in the polypeptide. The glycosylated core portion has the structure Manα1-3 (Manαβ1-6) Manβ11-4 GlcNAcβ1-4 GlcNAc-Asn contained within the boxed area in FIGS. 3A–3C. The polypeptide also has outer oligosaccharide branches (outer branches) that contain N-acetylglucosamine. Both complex and hybrid asparagine-linked oligosaccharides contain N-acetylglucosamine containing outer branches, while high mannose oligosaccharides do not. Bacterial cells do not include glycosylated core portions attached to asparagine amino acids. Yeast cells do not have asparagine-linked oligosaccharides of either the complex or hybrid type and therefore yeast do not have N-acetylglucosamine containing outer branches. Plant cells are capable of producing a polypeptide having a glycosylated core portion linked to an asparagine amino acid as well as N-acetylglucosamine containing outer branches.

The glycopolypeptide multimer comprises a polypeptide that has a glycosylated core portion as well N-acetylglucosamine containing outer branches and in detectable sialic acid residues and the entire the multimer is free from detectable sialic acid residues. Sialic acid, the predominant terminal carbohydrate of mammalian glycoproteins, has not been identified as a carbohydrate residue of plant proteins. The terminal carbohydrate residues found in plants include xylose, fucose, N-acetylglucosamine, mannose or galactose as has been described by Sturm et al., *J. Biol. Chem.* 262: 13392 (1987). In other respects, plant glycoproteins and carbohydrates attached to those proteins are very similar to mammalian glycoproteins. A glycopolypeptide multimer produced in a plant comprises a polypeptide having a glycosylated core portion as well as N-acetylglucosamine containing outer branches but is free from detectable sialic acid residues.

A gene coding for a polypeptide having within its amino acid residue sequence, the N-linked glycosylation signal, asparagine-X-serine/threonine, where X can be any amino acid residue except possibly proline or aspartic acid, when introduced into a plant cell would be glycosylated via oligosaccharides linked to the asparagine residue of the sequence (N-linked). See, Marshall, *Ann. Rev. Biochem.* 41: 673 (1972) and Marshall, *Biochem. Soc. Symp.* 40: 17 (1974) for a general review of the polypeptide sequences that function as glycosylation signals. These signals are recognized in both mammalian and plant cells. However in plant cells these signals do not result in asparagine-linked oligosaccharides that contain terminal sialic acid residues as are found in mammalian cells when expressed in a plant cell, a polypeptide containing the N-linked glycosylation signal sequence would be glycosylated to contain a glycosylated core portion as well as N-acetylglucosamine containing outer branches and would be free from detectable sialic acid residues.

A glycopolypeptide multimer, a protein, or a polypeptide of the present invention is free from detectable sialic acid residues as evidenced by its lack of specific binding to lectins specific for sialic acid such as wheat germ agglutinin or *Ricinus communis*, agglutinin. Methods for determining the binding of a glycosylated polypeptide chain to a particular lectin are well known in the art. See, e.g., Faye et al., *Ana. Biochem.* 149: 218 (1985) and Goldstein et al., *Adv. Carbohydr. Chem. Biochem.*, 35: 127 (1978). Typical methods for determining whether a glycosylated polypeptide chain binds to a particular lectin include methods using lectin columns, and methods where the glycosylated polypeptide is bound to nitrocellulose and probed with a biotinylated lectin. The exact specificity of the lectin may be determined by competing the lectin binding with a particular oligosaccharide such as a sialic acid residue.

Immunoglobulin superfamily molecules, and immunoglobulins may have various carbohydrate groups attached to them. Typically the carbohydrate is found on the immunoglobulin heavy chain constant region except for a few instances when the tripeptide acceptor sequence asparagine-X-serine/threonine(N-linked signal), is found within the heavy chain variable region. Other immunoglobulin superfamily molecules containing the tripeptide acceptor sequence (N-linked glycosylation sequence) within its amino acid residue sequence would also contain carbohydrate groups attached to the asparagine of that tripeptide acceptor sequence. The typical carbohydrate groups attached to 7 human heavy chains are described by Jeske and Capra, in *Fundamental Immunology*. W. E. Paul, ed., Raven Press, New York, N.Y. (1984). The carbohydrate attachment sites are highly conserved between various species and the comparable classes of immunoglobulin heavy chains. Table B shows the various oligosaccharides on each of the human immunoglobulin heavy chains.

TABLE B

Structural Characteristics of Human Immunoglobulin Heavy Chains Constant Region

| Chain | Whole Chain | | | Oligosacchrides | | No. of residues | |
|---|---|---|---|---|---|---|---|
| | | | Position of | | | (approximate) | |
| | Domains | Inter-chain bridges | H–L bridge | GlcN | GalN | Hinge | C Region |
| gamma 1 | 4 | 3 | 220 | 1 | 0 | 15 | 330 |
| gamma 2 | 4 | 5 | 131 | 1 | 0 | 12 | 325 |
| gamma 3 | 4 | 12 | 131 | 1 | 0 | 62 | 375 |
| gamma 4 | 4 | 3 | 131 | 1 | 0 | 14 | 325 |
| α 1 | 4 | 5 | 133 | 2 | 5 | 26 | 350 |
| α 2 A2m(1) | 4 | 4 | missing | 4 | 0 | 13 | 340 |
| α 2 A2m(2) | 4 | 5 | 133 | 5 | 0 | 13 | 340 |
| mu | 5 | 4 | 140 | 5 | 0 | 0 | 450 |
| epsilon | 5 | 3 | 127 | 6 | 0 | 0 | 420 |
| delta | 4 | 2 | 128 | 3 | 4 or 5 | 64 | 380 |

Preferably, the polypeptide present in the glycopolypeptide multimer includes the N-linked glycosylation signal within the immunoglobulin molecule amino acid residue sequence. In other preferred embodiments, the N-linked glycosylation is present in the region of the polypeptide that is not an immunoglobulin residue sequence.

In preferred embodiments, the biologically active glycopolypeptide multimer comprises secretory IgA. Secretory IgA is made up of four immunoglobulin alpha heavy chains, four immunoglobulin light chains, J chain and secretory component all bonded together to form a secretory IgA molecule containing an IgA dimer. The secretory IgA molecule contains heavy and light chain variable regions that bind specifically to an antigen. The secretory IgA molecule may contain either IgA$_1$ or IgA$_2$ molecules. For a general discussion of secretory IgA, see Mesteckey et al., *Advances in Immunology*. 40: 153 (1937).

The final assembled secretory IgA, of animals is the product of two distinct cell types: plasma cells that produce IgA with attached J chain and epithelial cells that produce secretory IgA. The transcytosis and secretion of the complex is the result of the membrane only at the luminal surface of the cell. The interaction of the four components of the complex (alpha, gamma, J, SC) results in an immunoglobulin structure which is exceptionally resistant to the degradative environment associated with mucosal surfaces.

In other preferred embodiments the biologically active glycopolypeptide multimer is a secretory IgM molecule that contains five IgM molecules, three J chain molecules and secretory component all disulfide bonded together.

Both secretory immunoglobulins (IgM and IgA) are resistant to proteolysis and degradation and therefore are active when present on mucosal surfaces such as the lungs or the gastrointestinal tract. See, Tomasi, N. *Basic and Clinical Immunology*. 198, Lange Medical Publications, Los Altos, Calif. (1982).

In preferred embodiments, a biologically active glycopolypeptide multimer has within it at least on catalytic site. This catalytic site may be an enzymatic site that is formed by one or more polypeptides. The catalytic site present is typically defined by an amino acid residue sequence that is known to form a catalytic site alone or together with the amino acid residue sequences of other polypeptides. This catalytic site may be the active site of an enzyme, or the binding site of an immunoglobulin. See, e.g., Tramontano et al., *Science*, 234: 1566 (1986). The present invention also contemplates other enzymes containing a catalytic site such as the enzymes described in Biochemistry Worth Publishers, Inc., New York (1975).

In other preferred embodiments, the present invention contemplates a biologically active glycopolypeptide multimer comprising a polypeptide having a glycosylated core portion as well as N-acetylglucosamine containing outer branches and includes an immunoglobulin molecule amino acid residue sequence, bonded to another polypeptide including a different immunoglobulin molecule amino acid residue sequence where the multimer is free from detectable sialic acid.

Catalytic glycopolypeptide multimers are contemplated wherein the catalytic site of the glycopolypeptide multimer is comprised of a first and second portion. The first portion of the catalytic site is also defined by an immunoglobulin amino acid residue sequence. The second portion of the catalytic site is defined by a different immunoglobulin amino acid residue sequence. The first and second portions of the catalytic site are associated together to form a greater portion of the catalytic site. In more preferred embodiments, the first portion of the catalytic site is defined by an immunoglobulin heavy chain variable region amino acid residue sequence and the second portion of the catalytic site is defined by an immunoglobulin light chain variable region amino acid residue sequence that is associated with the heavy chain amino acid residue sequence to form a larger portion at the catalytic site.

The present invention also contemplates a biologically active glycopolypeptide multimer comprising:

(i) A polypeptide having a glycosylated core portion as well as a N-acetylglucosamine-containing outer branches and an immunoglobulin molecule amino acid residue sequence and the polypeptide does not bind to a mouse immunoglobulin binding lectin; and (ii) another polypeptide containing a different immunoglobulin molecule amino acid residue sequence, where this another polypeptide is bonded to the polypeptide.

Mouse immunoglobulin binding lectins include lectins that specifically bind terminal sialic acid residues such as wheat germ agglutinin and *Ricinus communis* agglutinin. A mouse immunoglobulin binding lectin is specific for terminal sialic acid residues and thus does not bind an immunoglobulin produced in a plant cell because immunoglobulins produced in plants do not contain terminal sialic acid residues. See, Osawa et al., *Ana. Rev. Biochem.* 56: 21–42 (1987) for a general discussion of lectin binding properties.

E. Passive Immunizations Using Immunoglobulins Produced in Plants

Methods of passively immunizing an animal against a preselected ligand by contacting a composition comprising a biologically active glycopolypeptide multimer of the present invention that is capable of binding a preselected ligand with a mucosal surface of an animal are contemplated by the present invention.

Biologically active glycopolypeptide multimers such as immunoglobulin molecules capable of binding a preselected antigen can be efficiently and economically produced in plant cells. These immunoglobulin molecules do not contain sialic acid yet do contain core glycosylated portions and N-acetylglucosamine containing outer branches. In preferred embodiments, the immunoglobulin molecule is either IgA, IgM, secretory IgM or secretory IgA.

Secretory immunoglobulins, such as secretory IgM and secretory IgA are resistant to proteolysis and denaturation and therefore are desirable for use in harsh environments. Contemplated harsh environments include acidic environments, protease containing environments, high temperature environments, and other harsh environments. For example, the Gastrointestinal tract of an animal is a harsh environment where both proteases and acid are present. See, Kobayishi et al., *Immunochemistry*, 10: 73 (1973). Passive immunization of the animal is produced by contacting the glycopolypeptide multimer with a mucosal surface of the animal. Animals contain various mucosal surfaces including the lungs, the digestive tract, the nasopharyngeal cavity, the urogenital system, and the like. Typically, these mucosal surfaces contain cells that produce various secretions including saliva, lacrimal fluid, nasal fluid, tracheobronchial fluid, intestinal fluid, bile, cervical fluid, and the like.

In preferred embodiments the glycopolypeptide multimer, such as the immunoglobulin molecule is immunospecific for a preselected antigen. Typically, this antigen is present on a pathogen that causes a disease that is associated with the mucosal surface such as necrotizing enterocolitis, diarrheal disease, and cancer caused by carcinogen absorption in the intestine. See e.g., McNabb and Tomasi, *Ann. Rev. Microbiol.* 35: 477 (1981) and Lawrence et al., *Science*, 243: 1462 (1989). Typical pathogens that cause diseases associated with a mucosal surface include both bacterial and viral pathogens such as *E. coli, S. typhimurium, V. cholera*, and *S. mutans*. The glycopolypeptide multimer is capable of binding to these pathogens and preventing them from causing mucosal associated or mucosal penetrating diseases.

In preferred embodiments, the composition contacted with the animal mucosal surface comprises a plant material and a biologically active glycopolypeptide multimer that is capable of binding a preselected ligand. The plant material present may be plant cell walls, plant organelles, plant cytoplasm, intact plant cells containing the glycopolypeptide multimer, viable plants, and the like. This plant cell material is present in a ratio from about 10,000 grams of plant material to about 100 nanograms of glycopolypeptide multimer, to about 100 nanograms of plant material for each 10 grams of glycopolypeptide multimer present. In more preferred embodiments, the plant material is present in a ratio from about 10,000 grams of plant material for each 1 mg of glycopolypeptide multimer present, to about a ratio of 100 nanograms of plant material present for each gram of glycopolypeptide multimer present. In other preferred embodiments, the plant material is present in a ratio from about 10,000 grams of plant material for each milligram of glycopolypeptide multimer present to about 1 mg of plant material present for each 500 mg of glycopolypeptide multimer present.

In preferred embodiments, the composition comprising the biologically active glycopolypeptide multimer is a therapeutic composition. The preparation of therapeutic compositions which contain polypeptides or proteins as active ingredients is well understood in the art. Therapeutic compositions may be liquid solutions or suspensions, solid forms suitable for solution in, or suspension in a liquid prior to ingestion may also be prepared. The therapeutic may also be emulsified. The active therapeutic ingredient is typically mixed with inorganic and/or organic carriers which are pharmaceutically acceptable and compatible with the active ingredient. The carriers are typically physiologically acceptable excipients comprising more or less inert substances when added to the therapeutic composition to confer suitable consistencies and form to the composition. Suitable carriers are for example, water, saline, dextrose, glycerol, and the like and combinations thereof. In addition, if desired the composition can contain minor amounts of auxiliary substances such as wetting or emulsifying agents and pH buffering agents which enhance the effectiveness of the active ingredient. Therapeutic compositions containing carriers that have nutritional value are also contemplated.

In preferred embodiments, a composition containing a biologically active glycopolypeptide multimer comprises an immunoglobulin molecule that is immunospecific for a pathogen antigen. Pathogens are any organism that causes a disease in another organism. Particularly preferred are immunoglobulins that are immunospecific for a mucosal pathogen antigen. A mucosal pathogen antigen is present on a pathogen that invades an organism through mucosal tissue or causes mucosal associated diseases. Mucosal pathogens include lung pathogens, nasal pathogens, intestinal pathogens, dental pathogens, and the like. For a general discussion of pathogens, including mucosal pathogens, see, Davis et al., *Microbiology*, 3rd ed., Harper and Row, Hagerstown, Md. (1980).

Antibodies immunospecific for a pathogen may be produced using standard monoclonal antibody production techniques. See, *Antibodies: A Laboratory Manual*, Harlow et al., eds., Cold Spring Harbor, N.Y. (1988). The genes coding for the light chain and heavy chain variable regions can then be isolated using the polymerase chain reaction and appropriately selected primers. See, Orlandi er al., *Proc. Natl. Acad. Sci., U.S.A.* 86: 3833 (1989) and Huse et al., *Science*, 246: 1275 (1989). The variable regions are then inserted into plant expression vectors, such as the expression vectors described by Hiatt et al., *Nature*, 342: 76–78 (1989).

In a preferred embodiment, the biologically active glycopolypeptide multimer is a immunoglobulin immunospecific for an intestinal pathogen antigen. Particularly preferred are immunoglobulins immunospecific for intestinal pathogens such as bacteria, viruses, and parasites that cause disease in the gastrointestinal tract, such as *E. coli, Salmonellae, Vibrio cholerae*, Salmonellae typhimurium, and *Streptococcus mutans*. Also contemplated by the present invention are glycopolypeptide multimers that are immunoglobulins immunospecific for Diphtheria toxin, such as the antibody produced by the hybridoma ATCC No. HB 8329; antibodies immunospecific *Pseudomonas aeruginosa* exotoxin A, such as the antibody produced by the hybridoma D253-15-6 (ATCC No. H 8789); immunoglobulins immunospecific for Ricin A or B chain, such as the immunoglobulins produced by hybridomas TFT A1 (ATCC No. CRL 1771) or TFTB1 (ATCC No. 1759); immunoglobulins immunospecific for *Schistosoma mansoni* glycoprotein, such as the antibody produced by hybridoma 130 C/2B/8 (ATCC No. 8088); immunoglobulins immunospecific for *Shigella* SHIGA toxin and *Shigella*-like toxin, such as the antibodies produced by hybridoma 13C4 (ATCC No. 1794); immunoglobulins immunospecific for tetanus toxoid, such as the immunoglobulins produced by hybridomas 9F12 (ATCC No. HB8177) and hebridoma SAI3 (ATCC No. B8501); immunoglobulins immunospecific for Trichinella spiralis, such as hybridoma $7C_2C_5C_{12}$ (ATCC No. HB 8678); immunoglobulins immunospecific for Dengue viruses or complexes, such as the immunoglobulins produced by D3-2H2-9-21 (ATCC No. HB 114), hybridoma 15F3-1 (ATCC No. HB 47), hybridoma 3H5-1 (ATCC No. HB 46), hybridoma 5D4-11 (ATCC No. HB 49), hybridoma $1H10^{-6}$ (ATCC No. HB 48); immunoglobulins immunospecific for Hepatitis B surface antigen, such as hybridoma $H_{25}B10$ (ATCC No. CRL 8017), hybridoma $H_{21}F8-1$ (ATCC No. CRL 8018); immunoglobulins immunospecific for Herpes simplex viruses, such as the immunoglobulin produced by hybridoma 1D4 (ATCC No. HB 8068), hybridoma 39-S (ATCC No. HB 8180), hybridoma 52-S (ATCC No. HB 8181), hybridoma 3N1 (ATCC No. HB 8067); immunoglobulins immunospecific for influenza virus, such as the immunoglobulins produced by HK-PEG-1 (ATCC No. CL 139), hybridoma M2-1C6-4R3 (ATCC No. HB64); immunoglobulins immunospecific for parainfluenza virus, such as the immunoglobulin produced by hybridoma 9-3-4 (ATCC No. 8935); and immunoglobulins immunospecific for parvoviruses, such as the immunoglobulin produced by 3C9-D11-H11 (ATCC No. CRL 1745).

In other preferred embodiments, the glycopolypeptide multimer present in the composition is an immunoglobulin molecule that is immunospecific for a dental pathogen antigen such as *Streptococcus mutans* and the like. Particularly preferred are immunoglobulins immunospecific for a *Streptococcus mutans* antigen such as the immunoglobulin produced by hybridoma 15B2 (ATCC No. HB 8510).

The present invention contemplates producing passive immunity in an animal, such as a vertebrate. In preferred embodiments, passive immunity is produced in fish, birds, reptiles, amphibians, or insects. In other preferred embodiments passive is produced in a mammal, such as a human, a domestic animal, such as a ruminant, a cow, a pig, a horse, a dog, a cat, and the like. In particularly preferred embodiments, passive immunity is produced in an adult mammal.

In preferred embodiments, passive immunity is produced in an animal, such as a mammal that is weaned and therefore no longer nurses to obtain milk from its mother. Passive immunity is produced in such an animal by administering to the animal a sufficient amount of a composition containing a glycopolypeptide multimer immunospecific for a preselected ligand to produce a prophylactic concentration of the glycopolypeptide multimer within the animal. A prophylactic concentration of a glycopolypeptide multimer, such as an immunoglobulin is an amount sufficient to bind to a pathogen present and prevent that pathogen from causing detectable disease within the animal. The amount of composition containing the glycopolypeptide multimer required to produce a prophylactic concentrations will vary as is well known in the art with the size of the animal, the amount of pathogen present, the affinity of the particular glycopolypeptide multimer for the pathogen, the efficiency with which the particular glycopolypeptide multimer is delivered to its active location within the animal, and the like.

The present invention also contemplates a method for providing passive immunity against a pathogen to an animal, by administering to the animal an encapsulated, biologically active glycopolypeptide multimer capable of binding a pathogen antigen in an amount sufficient to establish within the animal a prophylactic concentration of the multimer that contains a polypeptide having a glycosylated core portion as well as N-acetylglucosamine containing outer branches and an amino acid residue sequence of an immunoglobulin molecule and where the multimer is free from detectable sialic acid residues.

In preferred embodiments, the biologically active glycopolypeptide multimer is encapsulated in a protective coating. The encapsulation material may be a membrane, a gel, a polymer or the like. The encapsulation material functions to protect the material it contains and to control the flow of material in and out of the encapsulation device. In preferred embodiments, the glycopolypeptide multimer is encapsulated within a plant cell wall, a plant cell, a micelle, an enteric coating, and the like.

In preferred embodiments, glycopolypeptide multimers, such as, tissue plasminogen activator, recombinant human insulin, recombinant alpha interferon and growth hormone, have been successfully administered and are therapeutically effective through buccal, nasal, and rectal mucosa using various approaches. Eppstein et al., *Alternative Delivery Systems for Peptides and Proteins as Drugs*, CRC Critical. Rev. in Therapeutic Drug Carrier Systems, 5: 99–139 (1988).

In preferred embodiments, the biologically active glycopolypeptide multimer is administered by intranasal formulations in solution. The formulation is administered by one of three ways: a single dose through a catheter, multiple doses through metered dose pumps (also called nebulizers); and multiple doses through the use of metered dose pressurized aerosols. If desired, the absorption of the peptide or protein across the nasal mucosa, may be promoted by adding absorption enhancers including nonionic polyoxyethylene ethers, bile salts such as sodium glycocholate (SGC) and deoxycholate (DOC), and derivative of fusidic acid such as sodium taurodihydrofusidate (STDHF).

Nasal insulin formulations containing 0.9% weight per volume of sodium chloride and 1% DOC, 0.5 U/kg of insulin administered as a spray using a metered dose spray pump resulted in rapid elevations of serum insulin. Moses et al., *Diabetes* 32: 1040 (1983). Dosages of biologically active glycopolypeptide multimers can range from 0.15 mg/kg up to 600 mg/kg, preferred dosages range from 0.15 mg/ml up to 200 mg/kg, and most preferred dosages range from 1 mg/kg up to 200 mg/kg in a nasal spray formulation. In preferred embodiments, the multimer does not cross the mucosal membrane and thus absorption enhancers are not required. Several dosage forms are available for the rectal delivery of biologically active glycopolypeptide multimers. These include suppositories (emulsion and suspension types), rectal gelatin capsules (solutions and suspensions), and enemas (macro: 100 milliliters (ml) or more; and micro: 1 to 20 ml). Osmotic pumps designed to deliver a volume of 2 ml in a 24 to 40 hour period have also been developed for rectal delivery. Absorption enhancers described for nasal formulations are included in the formulations if increased transport across rectal mucosa is desired. A preferred formulation for rectal administration of the biologically active glycopolypeptide multimer consists of the preferred ranges listed above in any one of the acceptable dosage forms.

Biologically active glycopolypeptide multimers can be administered in a liposome (micelle) formulation which can be administered by application to mucous membranes of body cavities. Juliano et al., *J. Pharmacol. Exp. Ther.*, 214: 381 (1980). Liposomes are prepared by a variety of techniques well known to those skilled in the art to yield several different physical structures, ranging from the smallest unilammelar vesicles of approximately 20 to 50 nanometers in diameter up to multilamellar vesicles of tens of microns in diameter. Gregoriadias, Ed., *Liposome Technology*, 1: CRC Press (1984). The biologically active glycopolypeptide multimers in the preferred dosages listed for nasal formulations are hydrated with a lyophilized powder of multilamellar vesicles to form glycopolypeptide containing-liposomes.

In a more preferred embodiment, biologically active glycopolypeptide multimers in the above mentioned preferred dosages are orally administered in gelatin capsules which are coated with a azoaromatic cross-linked polymer. The azopolymer-coated glycopolypeptide is protected from digestion in the stomach and the small intestine. When the azopolymer-coated glycopolypeptide reaches the large intestine, the indigenous microflora reduce the azo bonds, break the cross-links, and degrade the polymer film. This results in the release of the glycopolypeptide multimers into the lumen of the colon for subsequent local action or absorption.

Preferably, the pathogen specific glycopolypeptide multimer is administered in an amount sufficient to establish a prophylactic concentration of the multimer at a particular location in the animal. The amount of multimer that is administered to produce a particular prophylactic concentration will vary, as is well known in the art, with the amount of pathogen present, the exact location in the animal desired to be immunized, the affinity of the multimer for the pathogen, the resistance of the multimer to denaturation or degradation, the mode of pathogen inactivation, the dosage formulation and the like.

Preferably, the multimer is administered in 10 g to 100,000 g of plant material containing about 0.1 mg to 2,000 mg of multimer in 1 to 4 separate doses each day. This amount of multimer produces a prophylactic concentration of about 0.01 mg/kg of body weight to about 2,000 mg/kg of body weight. In preferred embodiments, the prophylactic concentration of multimer is from about 0.01 mg/kg of body weight to about 600 mg/kg of body weight. In other preferred embodiments, the prophylactic concentration is from about 0.01 mg/kg body weight to about 200 mg/kg of body weight.

The present invention contemplates a method for providing passive immunity to an animal against a preselected ligand, which method comprises administering to the animal biologically active glycopolypeptide multimers capable of binding a preselected ligand in an amount sufficient to establish within the animal a prophylactic concentration of the multimer. The multimer administered comprises a polypeptide having a glycosylated core portion as well as N-acetylglucosamine-containing outer branches and an amino acid sequence of an immunoglobulin molecule, such that the multimer is free from detectable sialic acid residues.

Particularly preferred, is a method for providing passive immunity to an animal against a pathogen, which method comprises administering to the animal a biologically active glycopolypeptide multimer capable of binding a pathogen in amounts sufficient to establish within the animal a prophylactic concentration of the multimer. The multimer administered comprises a polypeptide having a glycosylated core portion as well as N-acetylglucosamine-containing outer branches and an amino acid residue sequence of an immunoglobulin molecule, such that the multimer is free from detectable sialic acid residues.

In preferred embodiments, the multimer is administered as a composition constituted by the multimer and a material having nutritional value. A material having nutritional value is a substance or compound from which the animal can derive calories. Typical materials having nutritional value include proteins, carbohydrates, lipids, fats, glycoproteins, glycogen, and the like. Particularly preferred are materials having nutritional value that are plant materials or animal materials.

In other preferred embodiments, the multimer is administered as a composition constituted by the multimer and a physiologically inert material. Physiologically inert materials include solutions such as water and carrier compounds.

In other preferred embodiments, a method of passively immunizing an animal against a preselected ligand comprising introducing into the gastrointestinal tract of an animal a composition comprising plant cell walls and a biologically active glycopolypeptide multimer that is capable of binding a preselected antigen; said glycopolypeptide multimer comprising at least two polypeptides, one of said polypeptides having (a) an immunoglobulin amino acid residue sequence, and (b) an oligosaccharide comprising a core portion and a N-acetylglucosamine-containing outer branches, said multimer being free from sialic acid residues.

Other preferred embodiments contemplate a method of passively immunizing an animal against a preselected antigen, comprising:

(1) introducing into the gastrointestinal tract of an animal a composition comprising plant cells containing a biologically active glycopolypeptide multimer that is capable binding a preselected ligand; said multimer comprising at least two polypeptides, one of said polypeptides having (a) an immunoglobulin amino acid residue sequence, and (b) an oligosaccharide comprising a core portion and a N-acetylglucosamine-containing outer branches, such that the multimer is free from sialic acid residues; and (2) disrupting the plant cell within the gastrointestinal tract, thereby releasing the biologically active glycopolypeptide multimer into the gastrointestinal tract, and passively immunizing the animal.

D. Compositions Containing Glycopolypeptide Multimer

The present invention also contemplates biologically active compositions which comprise an encapsulated glycopolypeptide multimer comprising at least two polypeptides, one of said polypeptides having (a) an immunoglobulin amino acid residue sequence, and (b) an oligosaccharide comprising a core portion and a N-acetylglucosamine-containing outer branches, such that the multimer is free from sialic acid residues.

In preferred embodiments the glycopolypeptide multimer is encapsulated in a plant cell, a plant cell wall, an enteric coating, a coating, and the like.

Particularly preferred are compositions containing ratios of about 10,000 grams of plant material to each 100 nanograms of glycopolypeptide multimer present to ratios of about 100 nanograms of plant material for each 10 grams of glycopolypeptide multimer present in the composition. In more preferred embodiments, the plant material is present in a ratio from about 10,000 grams of plant material for each one milligram of glycopolypeptide multimer present, to a ratio of about 100 nanograms of plant material present for each gram of glycopolypeptide multimer present. In other preferred embodiments, the plant material is present in a ratio from about 10,000 grams of plant material for each milligram of glycopolypeptide multimer present to about one milligram of plant material present for each 500 milligrams of glycopolypeptide multimer present in the composition.

In other embodiments, the composition further comprises chlorophyll, synergistic compounds, medicines, compounds derived from medicinal plants, and various pharmaceuticals and the like. Compounds from a medicinal plant may be added to the composition by expressing the glycopolypeptide multimer in the medicinal plant and then harvesting the plant.

The present invention also contemplates a glycopolypeptide multimer produced according to the method comprising:

(a) introducing into the genome of a first member of the plant species a first mammalian gene coding for an autogenously linking monomeric polypeptide having a N-linked glycosylation signal that is a constituent part of the glycopolypeptide multimer to produce a first transformant;

(b) introducing into the genome of a second member of the same plant species another mammalian gene coding for another autogenously linking monomeric polypeptide that is a constituent part of the glycopolypeptide multimer to produce a second transformant;

(c) generating from said first and second transformants a progeny population; and (d) isolating from said progeny population a transgenic plant species that produces the glycopolypeptide multimer.

Other multimers produced by the methods of this invention are contemplated.

G. Generation of Biologically Important Proteins

The production of biologically or physiologically active multimeric proteins such as abzymes, immunoglobulins, enzymes, and the like, in relatively high yields is achieved in a transgenic, sexually reproducible plant constituted by plant cells that each contain integrated within the nuclear genome plural mammalian genes coding for autogenously linking polypeptides as well as the autogenously linking polypeptides themselves. These polypeptides are present in the plant cells as a biologically active polypeptide multimer such as a homomultimer or a heteromultimer. These transgenic plants are morphologically normal but for the presence of the mammalian genes is substantially all of their cells. The respective gene products can be present in substantially all or a portion of the plant cells, i.e., the products can be localized to a cell type, tissue or organ.

The foregoing transgenic plants are produced by introducing into the nuclear genome of a first member of the plant species a first mammalian gene that codes for an autogenously linkable monomeric polypeptide which is a constituent part of the multimeric protein to produce a viable first transformant. Similarly, another mammalian gene, coding for another autogenously linkable monomeric polypeptide which also is a constituent part of the multimeric protein is introduced into the nuclear genome of a second member of the same plant species to produce a viable second transformant. The so-obtained first and second transformants are then sexually crossed and cultivated to generate a progeny population from which transgenic plant species that produce the multimeric protein are isolated.

Transgenic plants embodying the present invention are useful not only to produce economically, and in relatively high yields, the desired multimeric protein but also as means for separating and/or concentrating a preselected ligand, such as a metal ion, from a fluid, i.e., gas or liquid.

The transgenic plants produce a glycopolypeptide multimer containing a polypeptide having a glucosylated core portion as well as N-acetylglucosamine containing outer ranches and an amino acid residue sequence of an immunoglobulin molecule, where the multimer is free from detectable sialic acid residues.

Passive immunity against a preselected pathogen is achieved in an animal by administering to the animal an encapsulated, biologically active glycopolypeptide multimer capable of binding a pathogen antigen in an amount sufficient to establish within the animal a prophylactic concentration of the multimer. The glycopolypeptide multimer administered is free from detectable sialic acid residues and contains a polypeptide having a glycosylated core portion as well as N-acetylglucosamine containing outer branches and an amino acid residue sequence of an immunoglobulin molecule.

The present invention also contemplates biologically active compositions comprising a glycopolypeptide multimer containing a polypeptide having a glycosylated core portion as well as a N-acetylglucosamine containing outer branches and an amino acid residue sequence of an immunoglobulin molecule, where the multimer is free from detectable sialic acid residues and is encapsulated in a protective coating such as a plant cell.

Thus, in one embodiment of the invention, a biologically active glycopolypeptide multimer is disclosed, which multimer comprises at least two polypeptides, one of the polypeptides having (a) an immunoglobulin amino acid residue sequence, and (b) an oligosaccharide comprising a core portion and N-acetylglucosamine-containing outer branches, the multimer being free from sialic acid residues. In one variation, the amino acid residue sequence includes an immunoglobulin heavy chain variable region amino acid residue sequence. In another variation, the amino acid residue sequence includes an immunoglobulin light chain variable region amino acid residue sequence. In still another embodiment, the amino acid residue sequence defines a catalytic or enzymatic site.

In another aspect, a biologically active glycopolypeptide as described above is contemplated, and further comprises another polypeptide including another amino acid residue sequence bonded to the polypeptide. In one alternative embodiment, a biologically active glycopolypeptide multimer according to the invention includes at least one catalytic site. In another embodiment, it includes at least one enzymatic site.

The invention also contemplates biologically active glycopolypeptide multimers comprising a polypeptide having a glycosylated core portion as well as N-acetylglucosamine-containing outer branches and an immunoglobulin molecule amino acid residue sequence, bonded to another polypeptide including a different immunoglobulin molecule amino acid residue sequence, the multimer being free from detectable sialic acid. In one variation, the immunoglobulin molecule amino acid residue sequence includes an immunoglobulin heavy chain variable region amino acid residue sequence. In another variation, the different immunoglobulin molecule amino acid residue sequence includes an immunoglobulin light chain variable region amino acid residue sequence.

In another aspect of the present invention, the immunoglobulin molecule amino acid residue sequence includes an immunoglobulin heavy chain variable region amino acid residue sequence and the different immunoglobulin molecule amino acid residue sequence includes an immunoglobulin light chain variable region amino acid residue sequence. In still another aspect, the immunoglobulin amino acid residue sequence defines a first portion of a catalytic site and the different immunoglobulin molecule amino acid residue sequence defines a second portion of the catalytic site, whereby the first and second portions are associated together to form a greater portion of the catalytic site. In other variations, the immunoglobulin molecule amino acid residue sequence includes an amino acid residue sequence of an immunoglobulin heavy chain variable region defining a portion of a catalytic site; and the different immunoglobulin molecule amino acid residue sequence includes the amino acid residue sequence of an immunoglobulin light chain variable region defining a portion of a catalytic site.

The invention also contemplates biologically active complex glycopolypeptide multimers as described hereinabove, wherein the immunoglobulin molecule amino acid residue sequence includes an immunoglobulin heavy chain variable region amino acid residue sequence defining a first portion of a catalytic site and the different immunoglobulin molecule amino acid residue sequence includes an immunoglobulin light chain variable region amino acid residue sequence defining a second portion of a catalytic site, whereby the first and second portions of the catalytic site are associated together to form a greater portion of the catalytic site.

The invention also discloses biologically active glycopolypeptide multimers comprising (i) a polypeptide having an oligosaccharide defined by a glycosylated core portion with N-acetylglucosamine-containing outer branches and an immunoglobulin molecule amino acid residue sequence, wherein the polypeptide does not bind to a mouse immunoglobulin-binding lectin; and (ii) another polypeptide containing a different immunoglobulin molecule amino acid residue sequence, wherein the another polypeptide is bonded to the polypeptide. In one variation, the immunoglobulin molecule amino acid residue sequence includes an immunoglobulin heavy chain variable region amino acid residue sequence; in another, the different immunoglobulin molecule amino acid residue sequence includes an immunoglobulin light chain variable region amino acid residue sequence.

Also disclosed are methods of passively immunizing humans or animals against a preselected ligand comprising contacting a prophylactic amount of a composition comprising a biologically active glycopolypeptide multimer that is capable of binding a preselected ligand with a mucosal surface of the animal; the multimer comprising a polypeptide having a glycosylated core portion as well as N-acetylglucosamine containing outer branches and an amino acid residue sequence of an immunoglobulin molecule, the multimer being free from detectable sialic acid residues. In one method, an encapsulated, biologically active glycopolypeptide multimer capable of binding a preselected ligand in an amount sufficient to establish within a subject a prophylactic concentration thereof is administered to a subject; the multimer comprising a polypeptide having a glycosylated core portion as well as N-acetylglucosamine containing outer branches and an amino acid residue sequence of an immunoglobulin molecule, the multimer being free from detectable sialic acid residues. In yet another variation, an encapsulated, biologically active glycopolypeptide multimer capable of binding a pathogen antigen in an amount sufficient to establish within a subject a prophylactic concentration thereof is administered to a subject; the multimer comprising a polypeptide having a glycosylated core portion as well as N-acetylglucosamine-containing outer branches and an amino acid residue sequence of an immunoglobulin molecule, the multimer being free from detectable sialic acid residues.

In various alternative embodiments, the multimer is encapsulated in a plant cell wall; the multimer encapsulated in a plant cell and a composition comprising the plant cells is administered; or the multimer is encapsulated in an enteric coating.

Other methods include methods of providing passive immunity against a preselected ligand to a subject (human or animal), which method comprises administering to the subject a biologically active glycopolypeptide multimer capable of binding a preselected ligand in an amount sufficient to establish within the subject a prophylactic concentration thereof; the multimer comprising a polypeptide having a glycosylated core portion as well as N-acetylglucosamine-containing outer branches and an amino acid residue sequence of an immunoglobulin molecule, the multimer being free from detectable sialic acid residues. Another method comprises administering to the subject a biologically active glycopolypeptide multimer capable of binding a pathogen in an amount sufficient to establish within the subject a prophylactic concentration thereof; the multimer comprising a polypeptide having a glycosylated core portion as well as N-acetylglucosamine-containing outer branches and an amino acid residue sequence of an immunoglobulin molecule, the multimer being free from detectable sialic acid residues. In one variation, the multimer is administered as a composition constituted by the multimer and a material having nutritional value; for example, the material having nutritional value is animal or plant material. In another variation, the multimer is administered as a composition constituted by the multimer and a physiologically inert material; it may also comprise plant material.

In various disclosed embodiments of the aforedescribed methods, the biologically active glycopolypeptide is an IgA molecule, or it may comprise secretory IgA. In one variation, the biologically active glycopolypeptide contains an IgA constant region amino acid residue sequence.

Preselected ligands, as described herein, may include mucosal pathogen antigens or specific intestinal pathogen antigens. For example, the pathogen antigen may be an *E. coli* antigen, a Vibrio cholerae antigen, a Salmonellae antigen, or a dental pathogen antigen. One exemplary dental pathogen antigen is a *Streptococcus mutans* antigen.

Another disclosed method of passively immunizing a subject against a preselected ligand comprising introducing into the gastrointestinal tract of a subject a composition comprising plant cell walls and a biologically active glycopolypeptide multimer that is capable of binding a preselected ligand; the multimer comprises at least two polypeptides, one of the polypeptides having (a) an immunoglobulin amino acid residue sequence, and (b) an oligosaccharide comprising a core portion and N-acetylglucosamine-containing outer branches, the multimer being free from sialic acid residues. Another method of passively immunizing an animal against a preselected ligand, which method comprises (a) introducing into the gastrointestinal tract of an animal a composition comprising plant cells containing a biologically active glycopolypeptide multimer that is capable of binding a preselected ligand, the multimer comprising at least two polypeptides, one of the polypeptides having (i) an immunoglobulin amino acid residue sequence, and (ii) an oligosaccharide comprising a core portion and N-acetylglucosamine-containing outer branches, the multimer being free from sialic acid residues; and (b) disrupting the plant cell within the gastrointestinal tract, thereby releasing the biologically active glycopolypeptide multimer into the gastrointestinal track and passively immunizing the subject.

The invention also discloses biologically active compositions comprising an encapsulated glycopolypeptide multimer comprising at least two polypeptides, one of the polypeptides having (a) an immunoglobulin amino acid residue sequence, and (c) an oligosaccharide comprising a core portion and a N-acetylglucosamine-containing outer branches, the multimer being free from sialic acid residues. In alternative embodiments, the coating is a plant cell; in another, the coating is an enteric coating.

The invention also discloses glycopolypeptide multimers produced according to the method comprising: (a) introducing into the genome of a first member of the plant species a first mammalian gene coding for an autogenously linking monomeric polypeptide having a N-linked glycosylation signal that is a constituent part of the glycopolypeptide multimer to produce a first transformant; (b) introducing into the genome of a second member of the same plant species another mammalian gene coding for another autogenously linking monomeric polypeptide that is a constituent part of the glycopolypeptide multimer to produce a second transformant (c) generating from the first and second transformants a progeny population; and (d) isolating from the progeny population a transgenic plant species that produces the glycopolypeptide multimer. In one alternative embodiment, the plant material is present in a ratio of greater than 1 milligram of plant material for each 1 milligram of glycopolypeptide multimer present.

In another, the plant material is present in a ratio of less than 1 milligram of plant material for each 1 milligram of glycopolypeptide multimer present.

EXAMPLES

The following examples are intended to illustrate, but not limit, the scope of the invention.

Example 1

Isolation of an Immunoglobulin Heavy Chain-Coding Gene and an Immunoglobulin Light Chain-Coding Gene From The Hybridoma Cell Line 6D4

Hybridoma cells secreting the 6D4 antibody described by Tramontano et al., *Science*, 234: 1566–1570 (1986) were grown to log phase in DMEM medium supplemented with 10% fetal calf serum. Total RNA was prepared from 2 liters of log phase 6D4 hybridoma cells using the methods described by Ullrich et al., *Science*, 196: 1313 (1977). Briefly, the 6D4 cells were collected by centrifugation and homogenized at room temperature for 20 seconds in 70 ml of 4 M guanidinium thiocyanate containing 5 mM sodium citrate at pH 7.0, 0.1 M 2-mercaptoethanol (2Me) and 0.5% sodium lauryl sarcosinate using a Polytron homogenizer. The homogenate was centrifuged briefly for 5 minutes at 8,000×g to remove the insoluble debris.

About 28 ml of homogenate was layered onto a 10 ml pad of 5.7 M CsCl (Bethesda Research Laboratories, Gaithersburg, Md.) in 4 mM ethylene diamine tetraacetic acid (EDTA at pH 7.5 in a Beckman SW70 Ti rotor. The solution was centrifuged for at least 5 hours at 50,000 revolutions per minute (rpm) at 15° C. The supernatant was carefully aspirated and the walls of the tubes dried to remove any remaining homogenate. The RNA pellet was dissolved in a solution containing 10 mM Tris-HCl at pH 7.4, 2 mM. EDTA and 0.5% sodium dodecyl sulfate (SDS). This solution was extracted twice with a phenol solution. The resulting aqueous phase was reextracted with solution containing Phenol:chloroform:isoamyl alcohol (25:25:1 by volume). The RNA was recovered from the resulting aqueous phase by adding 1/10 volume of 3 M sodium acetate and 2 volumes of ethanol. This solution was maintained at ~20° C. for 12 to 18 hours to precipitate the RNA. The solution containing the precipitated RNA was centrifuged for 20 minutes at 10,000×g at 4° C. to produce a RNA containing pellet. The excess salt was removed from the RNA pellet by admixing 5 ml of 70% ethanol to the RNA pellet and the solution was centrifuged for 10 minutes at 10,000×g at 4° C. The final RNA pellet was dissolved in 0.5 ml of DEPC—$H_2O$ and stored at -70° C. after removing a small aliquot to determine the RNA concentration by absorbance at 260 nm.

Messenger RNA (mRNA) enriched for sequences containing long poly A tracts was prepared from the total cellular RNA using the methods described in *Molecular Cloning: A Laboratory Manual*, Maniatis et al., eds., Cold Spring Harbor Laboratory, New York (1982). Briefly, the total RNA prepared above was resuspended in one ml of DEPC—$H_2O$ and maintained at 65' for five minutes. One ml of 2× high salt loading buffer consisting of 100 mM Tris-Cl, 1 M sodium chloride (NaCl), 2.0 mM EDTA at pH 7.5, and 1.0% sodium dodecyl sulfate (SDS) was added to the resuspended RNA and the mixture allowed to cool to room temperature. The mixture was then applied to an oligo-dT (Collaborative Research Type 2 or Type 3) column that had been previously prepared by washing the oligo-dT with a solution containing 0.1 M sodium hydroxide and 5 mM EDTA and then equilibrating the column with DEPC—$H_2O$. The eluate was collected in a sterile polypropylene tube and reapplied to the same column after heating the eluate for 5 minutes at 65° C. The oligo dT column was then washed with 20 ml of high salt loading buffer consisting of 50 mM Tris-Cl at pH 7.5, 500 mM NaCl, 1 mM EDTA at pH 7.5 and 0.5% SDS. The messenger RNA was eluted from the oligo dT column with 1 ml of buffer consisting of 10 mM Tris-Cl at pH 7.5, 1 mM EDTA at pH 7.5 and 0.05% SDS. The messenger RNA was concentrated by ethanol precipitation and resuspended in DEPC $H_2O$.

Complementary DNA (cDNA) was prepared from the mRNA prepared above. The first strand synthesis, second strand synthesis, and the fill-in reactions were carried out according to the procedures described by Watson et al., *DNA Cloning, Volume I*, D. M. Glover, ed., ( ). Briefly, a solution containing 10 μg of mRNA was maintained at 65° C. for 5 minutes and then quickly chilled on ice. The first cDNA strand was synthesized by admixing to this solution 100 μl of a reaction mixture containing 50 mM Tris-Cl at pH 8.3, 8 mM MgCl, 50 mM KCl, 2 μg oligo (dT) 1 mM dATP, 1 mM dGTP, 1 mM dTTP, 1 mM dCTP, 10 mM DTT, 60 units of RNasin (Promega Corporation, Madison, Wis.), 4 μg Actinomycin, 135 units of AMV reverse transcriptase and 10 μCi α$^{32}$P-dCTP. This reaction mixture was maintained at 44° C. for 1 hour. An additional 60 units of RNasin and 80 units of reverse transcriptase were added and the reaction mixture maintained at 44° C. for 30 minutes. The first strand cDNA synthesis reaction was terminated by adding 0.005 ml of a solution containing 50 mM EDTA and 10% SDS. The nucleic acids were purified by phenol extraction and then concentrated by ethanol precipitation.

The second strand cDNA was synthesized by admixing all of the first strand cDNA product produced above to a 100 μl solution containing 20 mM Tris-Cl at pH 7.5, 100 mM KCl, 5 mM $MgCl_2$, 10 mM ($NH2$ $SO_4$, 10 mM DTT, 0.05 mg/ml bovine serum albumin (BSA), 50 μM of dGTP, 50 μM dATP, 50 μM dTTP, 50 μM dCTP, 150 μM beta-nicotinamide adenine dinucleotide (β-$NAD^+$) (Sigma Chemical Company, St. Louis, Mo.), 15 μCi/μl [α-$^{32}$P]dCTP, 30 units *E. coli* DNA polymerase, 2.5 units RNase H, and 4 units *E. coli* DNA ligase. This solution was maintained at 14 C. for 1 hour and then further maintained at 25° C. for 1 hour. The second strand cDNA synthesis reaction was terminated by adding 5 μl of 0.05 M EDTA at pH 8.0, 5 μl of 10% SDS. The nucleic acids were purified from this reaction mixture by phenol extraction followed by ethanol precipitation.

The double stranded cDNA produced above was prepared for insertion into a cloning vector, by converting the ends of the double stranded cDNA to blunt ends in the following fill-in reaction. One half of the double stranded cDNA produced above was added to a solution containing 33.4 mM Tris-acetate at pH 7.8, 66.6 mM potassium acetate, 10 mM magnesium acetate, 0.5 M .DTT 87.5 μg/ml BSA, 310 μM dGTP, 310 μM dATP, 310 μM dTTP, 310 μM dCTP and 8 units of T4 DNA polymerase. This solution was maintained at 37 C. for 30 minutes and the reaction terminated by adding 5 μl of 0.05 M EDTA. The blunt-ended, cDNA produced was purified by phenol extraction and ethanol precipitation.

Eco RI adaptors were annealed and then ligated to the blunt-ended cDNA produced above. Briefly, polynucleotide N1(Table 1) was kinased by adding 1 μl of the polynucleotide and 20 units of T4 polynucleotide kinase to a solution containing 70 mM Tris-Cl at pH 7.6, 10 mM $MgCl_2$, 5 mM DTT, 10 mM 2Me and 500 μg/ml of BSA. The solution was maintained at 37° C. for 30 minutes and the reaction stopped by maintaining the solution at 65° C. for 10 minutes. 20 ng of polynucleotide N2 (Table 1) was added to the above kinasing reaction together with 1/10 volume of a solution containing 20 mM Tris-Cl at pH 7.4, 2 mM $MgCl_2$ and 15 mM NaCl. This solution was heated to 70° C. for 5 minutes and allowed to cool to room temperature, approximately 25° C., over 1.5 hours in a 500 μl beaker of water. During this time period, the 2 polynucleotides present in the solution annealed to form the double stranded Eco RI adaptor.

TABLE 1

| Eco RI Adaptor Polynucleotides | |
|---|---|
| (N1) 5'-CCTTGACCGTAAGACATG-3' | (SEQ ID NO 1) |
| (N2) 5'-AATTCATGTCTTACGGTCAAGG-3' | (SEQ ID NO 2) |

This double stranded Eco RI adaptor was covalently linked (ligated) to the blunt-ended cDNA produced above by adding 5 μl of the annealed adaptors to a solution containing 50 μl Tris-Cl at pH 7.5, 7 μl $MgCl_2$, 1 mM DTT, 1 mM ATP and 10 units of T4 DNA ligase. This solution was maintained at 37° C. for 30 minutes and then the T4 DNA ligase was inactivated by maintaining a solution at 72° C. for 15 minutes.

The 5' ends of the resulting cDNA were phosphorylated by admixing 5 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

The cDNA prepared above was size fractionated to obtain long cDNA inserts using a method similar to the method described in *Molecular Cloning: A Laboratory Manual*, Maniatis et al., eds., Cold Spring Harbor Laboratory, New York (1982). Briefly, the reaction mixture prepared above was added to an equal volume of 2×CL4B column buffer consisting of 20 mM Tris-Cl at pH 8.0, 1.2 M NaCl, 1 mM EDTA and 0.1% sarkosyl. This solution was loaded onto a 5 ml CL-4B column that was previously prepared using pre-swollen sepharose CL-4B (Pharmacia LKB Biotechnology Inc., Piscataway, N.J.). The sample was allowed to enter the column and then the column was filled with 1× column buffer consisting of 10 mM Tris-Cl at pH 8.0, 600 mM NaCl, 1 mM EDTA and 0.1% sarkosyl. The column was allowed to flow by gravity and approximately 200 µl fractions were collected manually. The size of the double stranded cDNA present in each of the fractions was determined by gel electrophoresis through a 0.8% agarose gel. Fractions containing high molecular weight cDNA as determined by the agarose gel electrophoreses were pooled and concentrated using butanol extraction and then ethanol precipitated to produce size-fractionated cDNA.

The size-fractionated cDNA prepared above was ligated directly into lambda Zap (Stratagene Cloning Systems, La Jolla, Calif.) that had been previously digested with the restriction endonuclease Eco RI. The ligation mixture was packaged according to the manufacturers' instructions using Gigapack II gold packaging extract available from Stratagene Cloning Systems and plated on BB4 cells (Stratagene Cloning Systems, La Jolla, Calif.) to produce plaques.

The plaques were screened with a radiolabeled probe containing the constant region gene of a human antibody. Briefly, the human IgG constant region probe previously described by Rabbitts et al., *Cold Spring Harbor Quantitative Biology* 45: 867–878 (1980), and the human Kappa light chain probe previously described by Rabbitts et al., *Cold Spring Harbor Quantitative Biology* 45: 867–378 (1980), was nick translated using standard protocols described by Molecular Cloning: A Laboratory Manual, Maniatis et al., eds., Cold Spring Harbor, N.Y. (1982). Probes prepared using this protocol and having a specific activity of greater than $1\times10^8$ cpm/µg were hybridized with plaques from the above-prepared library using methods well known to one skilled in the art. Briefly, the titer of the cDNA library prepared above was determined by making serial dilutions of the library into a buffer containing 100 mM NaCl, 50 mM Tris-Cl at pH 7.5 and 10 mM magnesium sulfate. 10 µl of each dilution was admixed to 200 µl of exponentially growing *E. coli* cells and maintained at 37° C. for 15 minutes to allow the phage to absorb to the bacterial cells. 3 ml of top agar consisting of 5 µl NaCl, 2 g/l of magnesium sulfate, 5 g/l of yeast extract, 10 µl of NZ Amine (casein hydrolysate) and 0.7% molten agarose was prepared and placed in a 50° C. water bath until used. The phage, the bacteria and the top agar were mixed and then evenly distributed across the surface of a prewarmed bacterial agar plate (5 g/l NaCl, 2 g/l magnesium sulfate, 5 g/l yeast extract, 10 µl NZ Amine and 15 g/l Difco agar. The plates were maintained at 37° C. for 12 to 24 hours during which time the lambda plaques developed on the bacterial lawn. The lambda plaques were counted to determine the total number of plaque forming units per milliliter in the original library.

The titered cDNA library was then plated out so that replica filters could be produced from the library. The replica filters were used to later segregate the individual clones containing cDNAs coding for either immunoglobulin heavy or immunoglobulin light chain. Briefly, a volume of the titer cDNA library that would yield 20,000 plaques per 150 millimeter plate was added to 600 µl of exponentially growing *E. coli* cells and maintained at 37° C. for 15 minutes to allow the phage to absorb to the bacterial cells. Then 7.5 ml of top agar was added to the solution containing the bacterial cells and phage. The bacterial cells with the phage absorbed to them were mixed with the top agar and the entire mixture distributed evenly across the surface of the pre-warmed bacterial agar plate. This entire process was repeated for sufficient number of plates to produce a total number of plaques at least equal to the library size. These plates were then maintained at 37° C. for 16 hours during which time the plaques appeared on the bacterial lawn. The plates were then overlaid with nitrocellulose filters and the orientation of each filter on the bacterial plates marked with ink dots. The filters were maintained on the bacterial plates for 1 to 5 minutes and then removed with a blunt-ended forceps and placed contact side up on a sponge pad soaked in a denaturing solution consisting of 1.5 M NaCl and 0.5 M NaOH for approximately 1 minute. The filter was then transferred, contact side up, onto a sponge pad containing a neutralizing solution consisting of 1.5 M NaCl and 0.5 M Tris-Cl at pH 8.0 for 5 minutes. The filter was then rinsed in a solution containing 0.36 M NaCl, 20 mM $NAH_2PO_4$ at pH 7.4, and 2 mM EDTA and placed on Whatman 3 MM paper to dry. This process was repeated for each bacterial plate to produce a second replica filter for hybridization. After all the filters were dry the sheets were placed between Whatman 3 MM paper and the filter was baked for 2 hours at 80° C. in a vacuum oven. The filters were now ready for hybridization with specific probes.

The baked filters were placed on the surface of a solution containing 0.9 M NaCl and 0.09 M sodium citrate at pH 7.0 until they have become thoroughly wetted from beneath. The filters were submerged in the same solution for 5 minutes. The filters were transferred to a pre-washing solution containing 50 mM Tris-Cl at pH 8.0, 1 M NaCl, 1 mM EDTA and 0.1% SDS. The pre-washing solution was then maintained at 42° C. for 2 hours.

The filters were removed from the pre-washing solution and placed in a pre-hybridization solution containing 25% formamide, 1.0 M NaCl 50% dextron sulfate, 0.05 M $NAPO_4$ at pH 7.7, 0.005 M EDTA, 0.1% ficoll, 0.1% BSA, 0.1% poly(vinyl pyrolidone), 0.1% SDS and 100 µg/ml denatured, salmon sperm DNA. The filters were maintained in the pre-hybridization solution for 4 to 6 hours at 42° C. with gentle mixing. The filters are then removed from the pre-hybridization solution and placed in a hybridization solution consisting of pre-hybridization solution containing $2\times10^8$ cpm/ml of $^{32}$P-labeled probe that has a specific activity of at least $1\times10^8$ cpm/µg. The filters were maintained in the hybridization solution for 12 to 24 hours at 42° C. with gentle mixing. After the hybridization was complete the hybridization solution is discarded and the filters were washed 3 to 4 times for 10 minutes in a large volume of a solution containing 0.9 MNaCl, 0.09 M sodium citrate at pH 7.0 and 0.1% SDS at 60° C. The filters were removed from the washing solution and air dried on a sheet of Whatman 3 MM paper at room temperature. The filters were taped to sheets of 3 MM paper and wrapped with plastic wrap and used to expose X-ray film (Kodak XR or equivalent) at −70° C. with an intensifying screen to produce an autoradiogram. The film was developed according to manufacturers' directions. Positive hybridization signals were aligned to the proper plaque by virtue of the asymmetrical ink spots placed on the nitrocellulose filters.

Hybridizing plaques were isolated to purity and the inserts excised from the lambda ZAP vector according to the underlying in vivo excision protocol provided by the manufacturer, Stratagene Cloning Systems, La Jolla, Calif. and described in Short et al., *Nucleic Acids Res.*, 16: 7583–7600 (1988). This in vivo excision protocol moves the cloned insert from the lambda ZAP vector into a phagemid vector to allow easy manipulation and sequencing. The hybridizing inserts were sequenced using the Sanger dideoxy method described by Sanger et al., *Proc. Natl. Acad. Aci. USA*, 74: 5463–5467 (1977) and using the Sequenase DNA Sequencing kit (united States Biochemical Corporation, Cleveland, Ohio). Two full length light chain clones designated pABZ100 and pABZ101 were identified by DNA sequencing. In addition, one full length heavy chain clone designated pABZ200 was also identified.

These full length cDNA clones were subcloned into mp18 using procedures similar to the procedures described in *Molecular Cloning: A Laboratory Manual.* Maniatis et al., eds., Cold Spring Harbor Laboratory New York (1982). Briefly, the phagemids containing the full length cDNA clones were digested with the restriction endonuclease Eco RI and the full length cDNA inserts isolated by gel electrophoresis. The isolated full length cDNA inserts were ligated to M13 mp 18 that had been previously digested with Eco RI. The ligation mixture was plated on appropriate bacterial host cells and phage plaques containing the full length cDNA inserts isolated. The accuracy of this cloning step was confirmed by restriction mapping.

Single stranded uracil-containing template DNA was prepared according to the protocols provided with the Muta-Gene M13 in vitro Mutagenesis kit (Bio-Rad Laboratories, Richmond, Calif.). Briefly, an isolated colony of bacterial strain CJ236 containing both the dut and ung mutations was admixed into 20 ml of LB media (10 g/l Bactotryptone, 10 g/l yeast extract and 5 g/l NaCl) containing 30 µg/ml chloramphenicol. This solution was maintained at 37° C. for 12 to 16 hours to produce an overnight culture. 1 ml of this overnight culture was admixed with 50 ml of 2×YT medium (16 g/l Bactotryptone, 10 g/l yeast extract and 5 g/l NaCl) containing 30 µg/ml chloramphenicol in a 250 ml flask. This solution was maintained at 37° C. with constant shaking for about 4 hours or until the optical density at 600 nanometers (nm) was 0.3. This optical density corresponds to approximately $1 \times 10^7$ colony forming units per millimeter. The M13 phage containing the full length cDNA inserts were added at a multiplicity of infection of 0.2 or less. This solution was maintained with shaking at 37° C. for 4 to 6 hours. 30 ml of the resulting culture was transferred to a 50 ml centrifuge tube and centrifuged at 17,000×g (12,000 revolutions per minute in the Sorvall SS-34 rotor) for 15 minutes at 4° C. The resulting phage particle containing supernatant was transferred to a fresh centrifuge tube and recentrifuged at 17,000×g for 15 minutes at 4° C. This second supernatant was transferred to a fresh polyallomer centrifuge tube and 150 micrograms of RNase A admixed to the supernatant. This supernatant was maintained at room temperature for 30 minutes to allow the RNase A to digest any RNA present. One/fourth volume of a solution containing 3.5 M ammonium acetate and 20% polyethylene glycol 8000 (PEG 8000) was admixed to this supernatant. This supernatant was maintained on ice for 30 minutes. During this time, any phage particles present in the supernatant were precipitated by the PEG 8000. The precipitated phage particles were collected by centrifuging this solution at 17,000×g for 15 minutes at 4° C. The resulting pellet was resuspended in 200 µl of high salt buffer (300 mM NaCl, 100 mM Tris-Cl at pH 8.0 and 1 mM EDTA). This solution was maintained on ice for 30 minutes and then centrifuged for 2 minutes in an microfuge to remove any insoluble material. The resulting supernatant was transferred to a fresh tube and stored at 4° C. until used as a phage stock.

Single stranded uracil containing template DNA was prepared by extracting the entire 200 µl phage stock twice with an equal volume of neutralized phenol. The aqueous phase was re-extracted once with a solution of phenol chloroform (25:25:1 phenol: chloroform: isoamyl alcohol) and further extracted several times with chloroform isoamyl alcohol (1:1/48 chloroform:isoamyl alcohol). One/tenth volume of 7.8 M ammonium acetate and 2.5 volumes of ethanol were admixed to the resulting aqueous phase. This solution was maintained at −70° C. for at least 30 minutes to precipitate the DNA. The precipitated DNA was collected by centrifuging the solution for 15 minutes at 4° C. The resulting DNA pellet was washed once with 90% ethanol and resuspended in 20 µl of a solution containing 10 mM Tris-Cl at pH 7.6 and 1 M EDTA. The amount of uracil containing template DNA present in this solution was determined by gel electrophoresis. This uracil containing template DNA was used in further mutagenesis steps to introduce restriction endonuclease sites into the full length cDNAs.

Mutagenic full length cDNAs were synthesized according to the procedures provided in the Muta-Gene kit (Bio-Rad Laboratories, Richmond, Calif.). Briefly, polynucleotides designed to introduce Eco RI restriction endonuclease sites were used to prime the synthesis of a mutagenic strand from the single-stranded uracil containing template DNA. The polynucleotide was phosphorylated by admixing 200 picomoles (pmoles) of the selected polynucleotide with a solution containing 100 mM Tris-Cl at pH 8.0, 10 mM MgCl$_2$, 5 mM DTT, 0.4 mM ATP and 4.5 units of T4 polynucleotide kinase to produce a kinasing reaction. This solution was maintained at 37° C. for 45 minutes. The kinasing reaction was stopped by maintaining the solution at 65° C. for 10 minutes. The kinased polynucleotide was diluted to 6 moles/µl with a solution containing 10 mM Tris-Cl at pH 7.6 and 1 mM EDTA.

The kinased polynucleotide was annealed to the single stranded uracil containing DNA template prepared above by admixing 200 ng of uracil containing template DNA, 3 moles of kinased polynucleotide, 20 mM Tris-Cl at pH 7.4, 2 mM MgCl$_2$ and 50 mM NaCl. This solution was maintained at 70° C. for 5 minutes and allowed to cool at a rate of approximately 1° C. per minute to 30° C. This solution was then maintained on ice until used. 1 µl of a solution containing 4 mM dATP, 4 mM dCTP, 4 mM dCTP, 4 mM TTP, 7.5 mM ATP, 175 mM Tris-Cl at pH 7.4, 37.5 mM MgCl, 215 mM DTT, was admixed to the solution along with 5 units of T4 DNA ligase and 1 unit of 4 DNA polymerase. This solution was maintained on ice for 5 minutes to stabilize the polynucleotide primer by initiation of DNA synthesis under conditions that favor binding of the polynucleotide to the uracil containing template. The solution was then maintained at 25° C. for 5 minutes and finally maintained at 37° C. for 90 minutes. The synthesis reaction was stopped by admixing 90 µl of stop buffer (10 mM Tris-Cl at pH 8.0 and 10 mM EDTA) to this solution and freezing it. This synthesis reaction was then stored at −20° C. until used.

The synthesis reaction was transformed into competent MV1190 cells using the protocol described in the Muta-Gene kit. Briefly, competent MV1190 cells were prepared by admixing an isolated colony of MV 190 cells to 10 ml of LB medium and maintaining this solution at 37° C. overnight with constant shaking. The next day, 40 ml of LB medium was admixed with a sufficient amount of the overnight MV 1190 culture to give an initial absorbance reading (optical density at 600 nm) of approximately 0.1. The solution was then maintained at 37° C. for approximately 2 hours with constant shaking. During this time, the culture should reach an absorbance reading of 0.8 to 0.9. When this absorbance reading is reached, the MV1190 cells were centrifuged at 5,000 rpm for 5 minutes at 0° C. The MV1190 cell pellet was resuspended in 1 ml of ice-cold 50 mM $CaCl_2$. An additional 19 ml of ice-cold 50 mM $CaCl_2$ was admixed to this solution. The resulting solution was maintained on ice for 30 minutes. The cells were centrifuged at 5,000 rpm for 5 minutes at 0° C. The MV1190 cell pellet was resuspended in 1 ml of ice-cold 50 mM $CaCl_2$. An additional 3 ml of ice-cold 50 mM $CaCl_2$ was admixed to the solution and the solution maintained on ice. The MV1190 cells were now competent for transformation.

A 10 μl aliquot of the synthesis reaction prepared above was admixed gently with 0.3 ml of competent MV1190 cells in a cold 1.5 ml sterile polypropylene tube. This solution was maintained on ice for 90 minutes. The solution was then placed in a 42° C. water bath for 3 minutes and returned immediately to ice. The transformed cells were then plated on the MV 1190 cell line at 3 different concentrations. 10 μl, 50 μl, and 100 μl of the transformed cells were added to individual tubes containing 0.3 ml of a MV1190 overnight cell culture. This solution was gently but thoroughly mixed and then 50 μl of 2% 5-bromo-4-chloro-3-indoyl-beta-D-galactopyranoside (X-GAL), 20 μl of 100 mM isopropyl-beta-thio-galactopyranoside (IPTG) and 2.5 ml of molten top agar (0.7 g Bacto-Agar/100 ml in LB medium) that had been cooled to about 50° C. was admixed to the solution. The resulting solution was immediately poured onto the surface of bacterial plates consisting of 15 g/L Bacto-Agar in LB medium. The agar was allowed to cool for about 10 minutes and then the plates were inverted and maintained overnight at 37° C. during which time plaques developed in the MV1190 cell lawn.

Isolated plaques resulting from the above transformation were picked and grown up according to standard procedures described in the instruction provided with the Muta-Gene Kit (Bio-Rad Laboratories, Richmond, Calif.). Double-stranded RF DNA was then produced from each plaque using the alkaline lysis mini-prep procedure described in *Molecular Cloning: A Laboratory Manual*, Maniatis et al., eds., Cold Spring Harbor Laboratory, Cold Spring Harbor, N.Y. (1982). The resulting DNA was then digested with restriction endonucleases that allow the identification of mutants containing the desired polynucleotide.

Mutants identified in this manner were then sequenced to confirm the DNA sequence of the mutant cDNA coding for either immunoglobulin heavy chain or immunoglobulin light chain.

Example 2

Construction of Expression Vectors Containing Kappa Light Chain Genes

An expression vector containing the entire kappa light chain gene including the kappa leader was produced in the following manner. The full length kappa light gene cDNA isolated above was mutagenized using polynucleotides P1 and P3 (Table 2) and the mutagenesis procedures described above. Polynucleotide P1 introduces an Eco RI restriction endonuclease site at the 5' end of the full length kappa cDNA. Polynucleotide P3 introduces an Eco RI restriction endonuclease site at the 3' end of the full length kappa light chain cDNA clone. Mutant transformants containing 2 additional Eco RI restriction endonuclease sites indicating that both polynucleotide P1 and polynucleotide P3 had been introduced into the mutants were isolated. These mutants were then sequenced to confirm that they did contain the DNA sequence of both polynucleotide P1 and polynucleotide P3.

Figure 2:
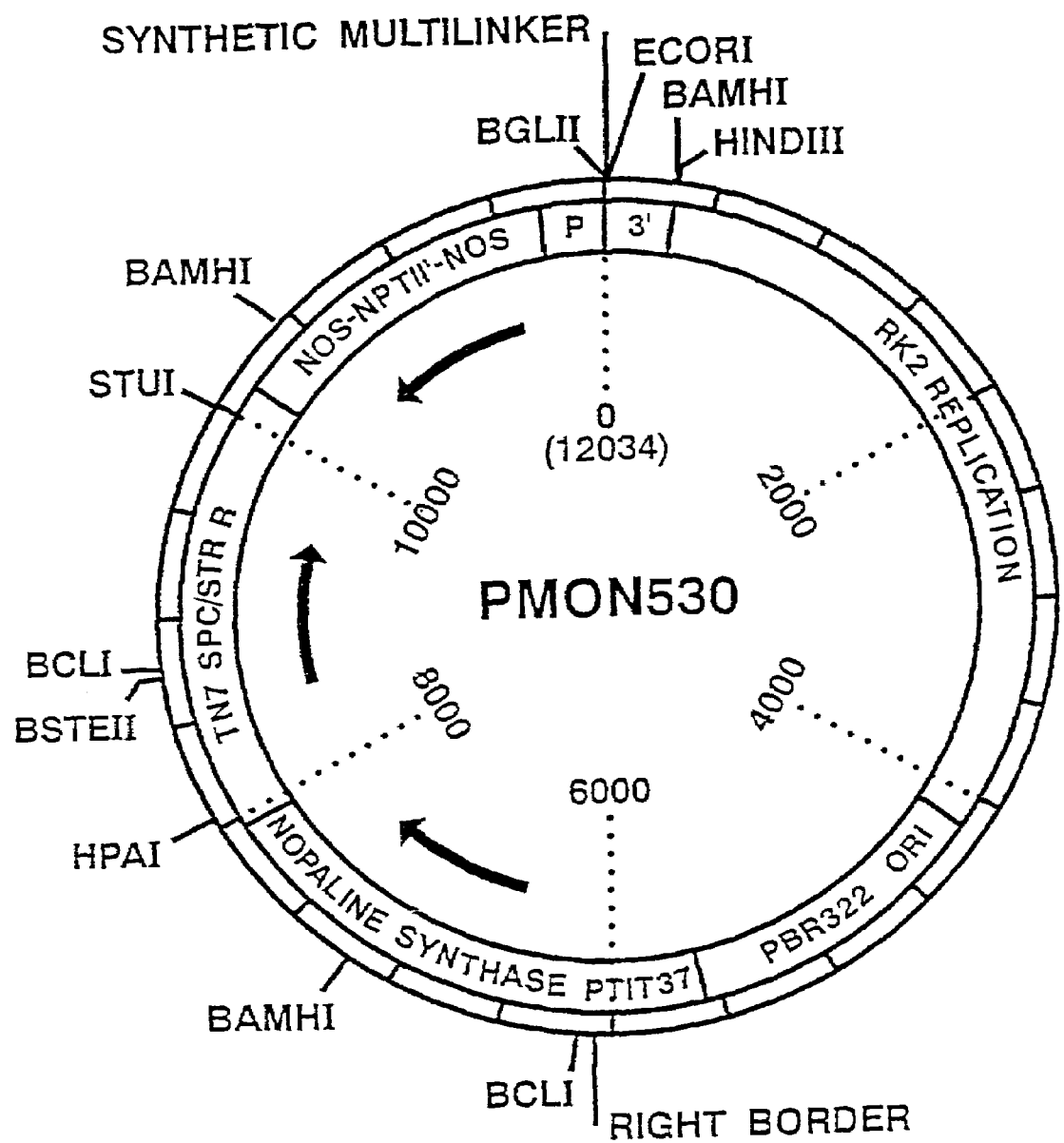
In FIG. 2, a schematic of the pMON530 binary 35 S—NOS cassette vector described in Rogers et al., *Meth. In Enzymol.* 153: 253 (1987) is shown. The CaMV 35 S promoter segment; 3'; and the NOS 3' nontranslated sequences are indicated. Also present are a 1.6 kb segment carrying the pBR322 origin of replication, a 2.4-kb segment of the nopaline-type pTiT37 plasmid that carries the right border of the nopaline T-DNA and intact nopaline synthase (NOS) gene, a 2.2-kb segment of Tn7 carrying the spectinomycin/streptomycin resistance determinant, a 1.6-kb segment encoding a chim eric NOS—NPTIT-NOS gene that provides selectable kanamycin resistance in transformed plant cells, and a synthetic multilinker containing unique restriction sites for insertion of other DNA segments.

The full length kappa light chain cDNA (FIG. 1A) was excised with the restriction endonuclease Eco RI sites at the 5' and 3' ends and the restriction fragment isolated using gel electrophoresis. This isolated restriction fragment was directly ligated to the pMON530 expression vector that had been previously digested with Eco RI (FIG. 2). (The pMON530 expression vector is commercially available from Monsanto, St Louis, Mo.) The resulting ligation mixture was transformed into suitable host cells and individual transformants isolated. DNA was prepared from the individual transformants using procedures similar to the standard of procedures described in *Molecular Cloning: A Laboratory Manual*, Maniatis et al., Cold Spring Harbor Laboratory, New York (1982). The transformant DNA was then digested with various restriction endonucleases to establish the orientation of the kappa light chain cDNA gene within the expression vector. The resulting kappa light chain expression vector contained a gene coding for the entire kappa chain including the kappa leader. An expression vector containing the kappa light chain gene without its leader sequence was produced in the following manner. The full length kappa light chain genes cDNA isolated above was mutagenized using polynucleotides P2 and P3 (Table 2) and the mutagenesis described above. Polynucleotide P2 introduces an Eco RI restriction endonuclease site just 5' of the sequence that codes for the N-terminal amino acid of the mature kappa light chain and thus removes the kappa light chain leader sequence normally transcribed in the wild type cDNA. Polynucleotide P3 introduces an Eco RI restriction endonuclease site at the 3' end of the full length kappa light chain cDNA clone. Mutant transformants containing 2 additional Eco RI restriction endonuclease sites indicating that both polynucleotide P2 and polynucleotide P3 had been introduced into the mutants were isolated. These mutants were then sequenced to confirm that they did, in fact, contain the DNA sequence of both polynucleotide P2 and polynucleotide P3.

The leaderless kappa light chain cDNA produced by this mutagenesis was excised with the restriction endonuclease Eco RI sites at the 5' and 3' ends and the restriction fragment isolated using gel electrophoresis. This isolated restriction fragment was directly ligated to the pMON530 expression vector that had been previously digested with Eco RI (FIG. 2). The resulting ligation mixture was transformed into suitable host cells and individual transformants isolated. DNA was prepared from the individual transform ants and the transformant DNA was then digested with various restriction endonucleases to establish the orientation of the leaderless kappa light chain cDNA gene within the expression vector. The resulting leaderless kappa light chain expression vector contained a gene coding for the kappa chain without its normal leader sequence.

TABLE 2

Mutagenic Polynucleotides (P1)-5'-TGTGAAAACCATATTGAATTCCACCAATACAAA-3' (SEQ ID NO 3)

(P2)-5'-ATTTAGCACAACATCCATGTCGACGAATTCAATCCAAAAAAGCAT-3' (SEQ ID NO 4)

(P3)-5'-GGGGAGCTGGTGGTGGAATTCGTCGACCTTTGTCTCTAACAC-3' (SEQ ID NO 5)

(P4)-5'-CCATCCCATGGTTGAATTCAGTGTCGTCAG-3' (SEQ ID NO 6)

(P5)-5'-CTGCAACTGGACCTGCATGTCGACGAATTCAGCTCCTGACAGGAG-3' (SEQ ID NO 7)

(P6)-5'-CCTGTAGGACCAGAGGAATTCGTCGACACTGGGATTATTTAC-3' (SEQ ID NO 8)

Example 3

Construction of Expression Vectors Containing Gamma Heavy Chain Gene

An expression vector containing the entire gamma heavy chain gene including the gamma leader was produced in the following manner. The full length gamma heavy chain gene cDNA isolated above was mutagenized using polynucleotides P4 and P6 (Table 2) and the mutagenesis procedures described above. Polynucleotide P4 introduces an Eco RI restriction endonuclease site at the 5' end of the native full length gamma cDNA. Polynucleotide P6 introduces an Eco RI restriction endonuclease site at the 3' end of the full length gamma heavy chain cDNA clone. Mutant transformants containing 2 additional Eco RI restriction endonuclease sites indicating that both polynucleotide P4 and polynucleotide P6 had been introduced into the mutants were isolated. These mutants were then sequenced to confirm that they did in fact contain the DNA sequence of both polynucleotide P4 and polynucleotide P6.

Figure 1B:
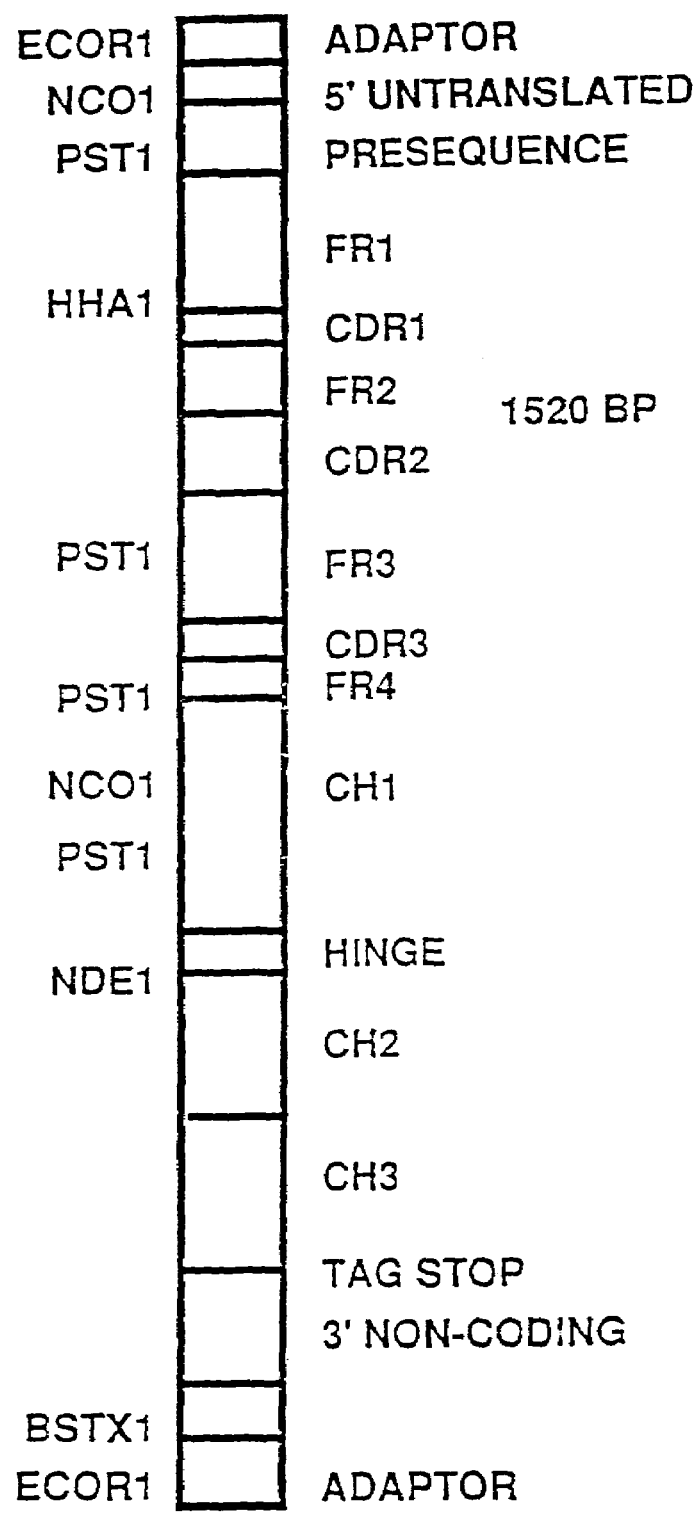

The full length gamma heavy chain cDNA was excised with the restriction endonuclease Eco RI at the 5' and 3' ends (FIG. 1B) and the restriction fragment isolated using gel electrophoresis. This isolated restriction fragment was directly ligated to the pMON530 expression vector that had been previously digested with Eco RI (FIG. 2). The resulting ligation mixture was transformed into suitable host cells and individual transformants isolated. DNA was prepared from the individual transformants and the transformant DNA was then digested with various restriction endonucleases to establish the orientation of the gamma heavy chain cDNA within the expression vector. The resulting gamma heavy chain expression vector contained a gene coding for the entire gamma heavy chain including the gamma leader.

An expression vector containing the gamma heavy chain gene without its leader sequence was produced in the following manner. The full length gamma heavy chain gene cDNA isolated above was mutagenized using polynucleotides P5 and P6 (Table 2) and the mutagenesis procedures described above. Polynucleotide P5 introduces an Eco RI restriction endonuclease site immediately 5' of the sequences that code for the N-terminal amino acid of the mature protein and thus remove the normal gamma leader sequence. Polynucleotide P6 introduces and Eco RI restriction endonuclease site at the 3' end of the full length gamma heavy chain cDNA clone. Mutant transformants containing 2 additional Eco RI restriction endonuclease sites indicating that both polynucleotide P5 and polynucleotide P6 had been introduced into the mutants were isolated. These mutants were then sequenced to confirm that they did contain both polynucleotide P5 and polynucleotide P6.

This leaderless gamma heavy chain cDNA was excised with the restriction endonuclease Eco RI sites located at the 5' and 3' ends and the resulting restriction fragment isolated using gel electrophoresis. This isolated restriction fragment was directly ligated to the pMON530 expression vector that had been previously digested with Eco RI (FIG. 2). The resulting ligation mixture was transformed into suitable host cells and individual transformants isolated. DNA was prepared from the individual transformants and the transformant DNA was then digested with various restriction endonucleases to establish the orientation of the gamma heavy chain cDNA within the expression vector. The resulting gamma heavy chain expression vector contained a gene coding for the gamma heavy chain without its native gamma leader.

Example 4

Introduction of Immunoglobulin Genes into Plants

The leaderless kappa expression vector, the leaderless gamma expression vector, the native kappa expression vector and the native gamma expression vector prepared in the above examples were mobilized into *Agrobacterium* strain GV3111-SE using the triparental conjugation system of Ditta et al., *Proc. Natl. Acad. Sci. USA*, 77: 7347–7351 (1980). Briefly, the *Agrobacterium* (acceptor) GV3111-SE, was grown on an agar plate containing MGL medium consisting of 2.6 g/L yeast extract, 5 g/L tryptone, 5 g/L NaCl, 5 g/L mannitol, 1.16 g/L monosodium glutamate, 0.25 g/L KH$_2$PO$_4$, 0.1 g/L MgSO$_4$-7H$_2$O per liter, and 1 mg/L biotin at pH 7.0 for 12 to 18 hr at 28 C. The *E. coli* (helper) strain containing the mobilization plasmid pRK2073 described by Better et al., *J. Bacteriol.* 155: 311 (1983), was grown on an agar plate containing LB agar (LB agar is 5 g/L yeast extract, 10 g/L tryptone, 10 g/L NaCl, 15 g/L Bacto-agar, at pH 7.0) for 12 to 18 hr at 37 C. The *E. coli* containing each of the expression vectors were grown on bacterial culture plates containing LB medium supplemented with 3 ug/ml tetracycline and 10 ug/ml kanamycin for 12 to 18 hr at 37 C. An equal amount (about 1×10$^8$ cells) of all three bacteria, the acceptor *Agrobacterium*, the helper *E. coli*, and the *E. coli* containing the expression vectors were mixed together and plated out on a bacterial plate containing AB agar medium containing 100 ug/ml kanamycin, 200 ug/ml spectinomycin and 50 ug/ml chloramphenicol (1 liter AB medium agar contains 1 g NH$_4$Cl, 0.3 g MgSO$_4$-7H$_2$O, 0.15 g KCl, 0.01 g CaCl$_2$, 2.5 mg FeS$_4$.7H$_2$O, 3 g K$_2$HPO$_4$, 1.15 g NaH$_2$PO$_4$—H$_2$O, 5 g glucose and 15 g Bacto-agar). The bacterial culture plates were incubated at 28 C. for two to four days. Single transformant colonies were admixed into a culture flask containing LB medium supplemented with 100 ug/ml kanamycin, 200 ug/ml spectinomycin and 50 ug/ml chloramphenicol was maintained with gentle shaking at 28 C. for 12 to 18 hours. Each of the expression vectors prepared in the above examples were now in a culture of *Agrobacterium* and thus ready to be introduced into a plant.

Tobacco leaf discs were transformed using the methods described in Rogers et al., in *Methods For Plant Molecular Biology*, Academic Press, Inc., San Diego (1988). Healthy, young tobacco leaves were surface sterilized by placing the leaves in a solution containing 20% household bleach (w/v) and 0.1% SDS (w/v) for 8 minutes. The leaves were then transferred to a solution containing 98% ethanol for 60 seconds and rinsed twice in sterile double distilled $H_2O$. The leaf discs were then punched with a 6-mm paper punch. The discs were placed basal side down, in MS 10 solution (MS salts, Gibco Laboratories, Grand Island N.Y., 0.01 mg/ml thiamine HCL, 0.001 mg/ml pyridoxine HCl, 0.001 mg/ml nicotinic acid, and 0.1 mg/ml inositol, 30 g sucrose, 0.01 ug/ml naphthalene acidic acid [NAA], 1.0 ug/ml benzyladenine [BA], and 10 g/l Bacto-agar at pH 6.0). Each disc was admixed to the culture of *Agrobacterium* containing the expression vectors for 5 seconds. The discs were then blotted dry on sterile filter paper and transferred basal side down to the MS10 medium and the medium maintained for 48 hours under normal growing conditions. Each leaf disc was then washed in sterile water to remove most of the *Agrobacterium* containing the expression vector. The leaf discs were blotted dry on sterile number 9 Whatman filter paper and then placed basal side up on MS10 medium selection plates containing 200 ug/ml kanamycin sulfate and 500 ug/ml carbenicillin. Selection plates were maintained under normal growing conditions for two weeks. Within the two weeks, callus appeared and shortly later shoots appeared. After the shoots appeared, they were transferred to regeneration plates containing MSO medium (MSIO with no NHA or BA) and 200 ug/ml kanamycin sulfate and 500 ug/ml carbenicillin. The shoots that rooted in the regeneration plates were transferred to soil to produce plantlets. The plantlets were maintained under standard growth conditions until they reached maturity.

A population of plantlets was prepared from each of the expression vectors constructed in the above examples using the procedure just outlined. Leaf extracts from each of the plantlet populations were screened for the presence of immunoglobulin heavy or light chain using an ELISA assay based on the methods described by Engvall et al., *J. Immunol.* 109: 129–135 (1972). Briefly, 50 ul of a solution containing 150 mM NaCl and 20 mM Tris-Cl at pH 8.0 (TBS), and either a goat anti-mouse heavy chain or a goat anti-mouse light chain specific IgG (Fisher Scientific, Pittsburgh, Pa.) was admixed into the wells of microtiter plates. The plates were maintained for about 16 hours at 4 C. to permit the goat antibodies to adhere to the microtiter well walls. After washing the wells four times with $H_2O$, 200 ul of TBS containing 5% non-fat dry milk admixed to the microtiter wells. The wells were maintained for at least 30 minutes at 20 C., the wells emptied by shaking and blotted dry to form a solid support, i.e., a solid matrix to which the goat antibodies were operatively attached.

Leaves from each of the transformants were homogenized in a mortar and pestle after removing the midvein. One-fourth volume of 5× TBS (750 mM NaCl and 100 mM Tris-Cl at pH 8.0) was admixed to the homogenized transformant leaves. Two-fold serial dilutions of the homogenate were made in TBS (150 mM NaCl and 20 mM Tris-Cl at pH 8.0). 50 ul of the two-fold serial dilutions were added to each separate microtiter well and the wells maintained for 18 hours at 4 C. to permit the formation of solid-phase immunoreaction products. The wells were then washed with room temperature distilled water. 50 ul of a 1:1000 dilution of either goat anti-mouse heavy chain or goat anti-mouse light chain specific antibody conjugated to horse radish peroxidase (BRPO) (Fisher Scientific, Pittsburgh, Pa.) in TBS was admixed to each of the microtiter wells. The wells were maintained for 2 hours at 37 C. followed by detection according to the manufacturer's instructions. Control Microtiter wells were produced in a similar fashion and contained extracts from plants transformed with the vector alone and did not express any detectable immunoglobulin products.

The immunoglobulin content of each plantlet was determined at least twice and the values shown in Table 3 are given as mean values. At least 9 plantlets from each population of plantlets were assayed in this manner. The plantlets expressing either immunoglobulin heavy chain or immunoglobulin light chain were now shown to be transformed with the immunoglobulin genes and are thus termed transformants or transgenic plants.

TABLE 3

Expression of Immunoglobulin Gamma and Kappa Chains in Tobacco[1]

| Gamma-NL[2] | Gamma-L |
|---|---|
| 30 ± 16 | 1412 ± 270 |
| (60) | (2400) |
| Kappa-NL | Kappa-L |
| 1.4 ± 1.2 | 56 ± 5 |
| (3.5) | (80) |

[1]Values are expressed in ng/mg total protein (mean ± S.D.).
[2]L indicates a leader or signal sequence is present; NL indicates a leader or signal sequence is absent.

The results presented in Table 3 demonstrate the importance of a signal sequence for the accumulation of the individual immunoglobulin chains. Kappa chain accumulation was 40-fold greater (on average) when the signal sequence was present in the cDNA construct; Gamma chain accumulation was 47-fold greater.

Example 5

Producing a Population of Progeny Expressing Both Immunoglobulin Heavy and Immunoglobulin Light Chain Transformants produced according to Example 4 expressing individual immunoglobulin chains were sexually crossed to produce progeny expressing both chains. Briefly, the hybrid progeny were produced by was to emasculating immature flowers by removing the anthers from one transformant expressing one immunoglobulin chain to produce a female transformant. The female transformant is then cross-pollinated from the other transformant (male) expressing the other immunoglobulin chain. After cross-pollination, the female transformant was maintained under normal growing conditions until hybrid seeds were produced. The hybrid seeds were then germinated and grown to produce hybrid progeny containing both the immunoglobulin heavy chain and the immunoglobulin light chain.

The leaves were homogenized and the homogenate assayed for immunoglobulin heavy chain or light chain expression using the ELISA assay described in Example 4 (see Table 4). The number of hybrid progeny expressing immunoglobulin heavy chain or immunoglobulin light chains is shown in Table 5. The hybrid progeny produced from the cross of the transformants expressing the kappa leader construct and the gamma leader construct contained assembled immunoglobulin molecules containing both gamma heavy chains and kappa light chains.

TABLE 4

Expression of
Immunoglobulin Gamma and Kappa Chains in Hybrid Progeny[1]

| Gamma-L[2] (Kappa-L) | Gamma-NL[3] (Kappa-NL) |
|---|---|
| 3330 ± 2000 (12800) | 32 ± 26 (60) |
| Kappa-L (Gamma-L) | Kappa-NL (Gamma-NL) |
| 3700 ± 2300 (12800) | 6.5 ± 5 (20) |

[1]Values are expressed in ng/mg total protein (mean ± S.D.).
[2]L indicates a leader or signal sequence is present
[3]NL indicates a leader or signal sequence is absent

TABLE 5

Expression and Assembly of Immunoglobulin
Gamma and Kappa Chains in Hybrid Progeny

| | Gamma only | Kappa only | Gamma Kappa | null |
|---|---|---|---|---|
| Kappa-NL X Gamma-NL | 4 | 6 | 3 | 5 (0% assembly) |
| Kappa-L X Gamma-L | 3 | 10 | 11 | 4 (95 ± 16% assembly) |

The results presented in Tables 4 & 5 demonstrate the importance of assembly of the two immunoglobulin chains. Compared to the parental transformants, the progeny that express both immunoglobulin chains together accumulate for more of each chain. On average, gamma chain showed a 2.5-fold increase in accumulation and kappa chain a 66-fold increase.

Compared to the transformants expressing cDNAs without leader sequences, the increased accumulation as a result of both the leader sequence and dual expression resulting from the sexual cross was surprisingly large. Gamma chains increased by 110-fold and kappa chains by 2,600-fold.

Example 6

Detection of Immunoglobulin Heavy Chain-Coding Genes and Immunoglobulin Light Chain-Coding Genes in the Transgenic Plants The presence of immunoglobulin heavy chain-coding genes or immunoglobulin light chain-coding chains in the transgenic plants and hybrid progeny was demonstrated by analyzing DNA extracted from the transgenic plants using the Southern blot procedure described in Maniatis et al., *Molecular Cloning—A Laboratory Manual*, Cold Spring Harbor Laboratory (1982). Briefly, DNA was extracted from 1 g of mature leaf tissue harvested from either the heavy chain gene transformants, the light chain gene transformants or the hybrid progeny after freezing the leaf segments in liquid nitrogen. The frozen leaf segments were homogenized in urea mix (420 g/L urea, 312.5 mM NaCl 50 mM Tris-Cl at pH 8.0, 20 mM EDTA and 1% sarcosine) with a mortar and pestle according to the procedures described by Shure, et al., *Cell*. 25: 225–233 (1986). The leaf homogenate was extracted with phenol: $CHCl_3$ (1:1 v/v) and the nucleic acids were precipitated by adding ⅙ volume of 4.4 M ammonium acetate at pH 5.2 and one volume of isopropyl alcohol and then maintaining the resulting solution at −20 C. for 30 minutes. The solution containing the precipitated nucleic acid was centrifuged for 15 minutes at 7500×g at 4 C. to collect the precipitated nucleic acid. The nucleic acid pellet was resuspended in a TE solution containing 10 mM Tris-Cl at pH 7.6 and 1 mM EDTA. The concentration of DNA in the resulting solution was determined by spectrophotometry.

DNA was prepared from each of the transformants using the above methods and 20 μg of transformant DNA was digested with the restriction endonuclease Hind III under conditions recommended by the manufacturer, Stratagene Cloning Systems, La Jolla, Calif. The resulting restriction endonuclease fragments were size fractionated on an agarose gel and blotted to nitrocellulose using the methods described in Maniatis et al., *Molecular Cloning: A Laboratory Manual*, Cold Spring Harbor Laboratory (1982). Briefly, after the DNA had been size fractionated by electrophoresis through an agarose gel, the DNA was stained ethidium bromide and a photograph of the gel produced. The gel containing the DNA was placed in a solution containing 1.5 M NaCl and 0.5 M NaOH for one hour at room temperature with constant gentle stirring. The gel was then placed in a solution containing 1 M Tris-Cl at pH 8.0 and 1.5 M NaCl for one hour at room temperature with constant gentle stirring. The pH of the gel was periodically checked by removing a small piece of the gel and determining its pH in a small volume of distilled $H_2O$. When the gel had reached a pH of approximately 8.0 the gel was placed upon a thick wick soaked with a solution containing 87.65 g/L NaCl, 13.8 g/L $NaH_2PO_4$—$H_2O$ and 3.7 g/L EDTA at pH 7.4 (10× SSC). A piece of nitrocellulose filter (Schleicher and Schuell B A 85, Keene, N.H.) that had been previously cut to the same size as the gel and soaked in a solution containing 10×SSC was placed upon the gel and any intervening air bubbles removed. Two pieces of Whatman 3 MM paper, cut to exactly the same size as the nitrocellulose filter were soaked in 2×SSC (2×SSC contains 17.53 g/L NaCl, 2.76 g/L $NaH_2PO_4$—$H_2O$ and 0.74 g/L EDTA at pH 7.4) and placed on top of the nitrocellulose filter and any intervening air bubbles removed. A stack of paper towels (5–8 centimeters high) cut to a size just slightly smaller than the Whatman 3 MM paper was placed on top of the Whatman 3 MM paper. A glass plate was placed on top of the resulting stack and a 500 gram weight placed on top of the plate. The resulting capillary action was allowed to proceed for 12 to 24 hours and this action transferred the DNA from the gel onto the nitrocellulose filter. The stack was disassembled and the nitrocellulose filter soaked in 6×SSC (6×SSC is 52.59 g/L NaCl, 8.28 g/L $NaH_2PO_4$—$H_2O$ and 2.22 g/L EDTA at pH 7.4) at room temperature for five minutes. The filter was placed upon a piece of dry Whatman 3 MM paper and allowed to air dry. The dried filter was placed between two sheets of 3 MM paper and baked for 2 hours at 80 C. under vacuum to operatively link the DNA to the nitrocellulose filter.

The baked filters were placed on the surface of a solution containing 0.9 M NaCl and 0.09 M sodium citrate at pH 7.0 until they were thoroughly wetted from beneath. The filters were submerged in the same solution for 5 minutes.

The filters were placed in a pre-hybridization solution containing 50% formamide, 0.9 M NaCl, 0.05 M NaPO$_4$ at pH 7.7, 0.005 M EDTA, 0.1% Ficoll, 0.1% BSA, 0.1% poly(vinyl pyrrolidone), 0.1% SDS and 100 µg/ml denatured, salmon sperm DNA. The filters were maintained in the pre-hybridization solution for 12 to 18 hours at 42° C. with gentle mixing. The filters were then removed from the pre-hybridization solution and placed in a hybridization solution consisting of pre-hybridization solution containing 1×10$^6$ cpm/ml of $^{32}$P-labeled gamma chain probe (the entire gamma expression vector was labeled) and 1×10$^6$ cpm/ml of $^{32}$P-labeled kappa chain probe (the entire expression kappa vector was labeled. The filters were maintained in the hybridization solution for 12 to 24 hours at 42 C. with gentle mixing. After the hybridization was complete the hybridization solution was discarded and the filters washed 4 times for 10 minutes per wash in a large volume of a solution containing 0.3 M NaCl, 0.03 M sodium citrate at pH 7.0 and 0.1% SDS at room temperature. The filters were then washed twice for 1.5 hours in a solution containing 0.15 M NaCl, 0.015 M sodium citrate at pH 7.0, and 0.1% SDS at 65 C. The filters were further washed by transferring them to a solution containing 0.2×SSC (0.03 M NaCl and 0.003 M sodium citrate at pH 7.0) and 0.1% SDS at 42 C. for 1 hour with gentle agitation. The filters were removed from the washing solution and air dried on a sheet of Whatman 3 MM paper at room temperature. The filters were then taped to sheets of 3 MM paper and wrapped with plastic wrap and used to expose X-ray film (Kodak XR or equivalent) at −70 C. with an intensifying screen to produce an autoradiogram. The film was developed according to manufacturers' directions.

The resulting autoradiogram (not shown) may be described as follows. A Southern blot of transgenic leaf DNA was prepared which demonstrated the incorporation of both kappa and gamma genes into the transgenic plant's genome. DNA from a transformant expressing a light chain cDNA without a leader sequence (pHi101) was applied to Lane 1. Lane 2 contained DNA from a cDNA transformant expressing the heavy chain cDNA with no leader (pHi201). Lane 3 contained DNA from a transformant expressing the full length light chain cDNA with a leader (pHi102). Lane 4 contained DNA from a transformant expressing the heavy chain cDNA with a leader (pHi202). Lane 5 contained DNA from an F$_1$ plant derived from a cross between a plant expressing the full length gamma cDNA and a plant expressing the full length kappa cDNA (pHi102×pHi201). In a Northern blot of transgenic tobacco leaf RNA demonstrating the expression of kappa and gamma mRNA in the transgenic plant leaf (not shown), lane 1 contained RNA from a transformant expressing a light chain cDNA without a leader sequence (pHi101). Lane 2 contained RNA from a heavy chain cDNA transformant, no leader (pHi201). Lane 3 contained RNA from a transformant expressing-full length light chain with leader (pHi102), lane 4 contained RNA from a transformant expressing heavy chain with leader (pHi202). Lane 5 contained RNA from an F$_1$ plant derived from a cross between plant expressing full length gamma cDNA and a plant expressing full length kappa cDNA (pHi102×pHi201). Lanes from separate hybridizations were aligned with respect to the 18S (1900 bp) and 25S (3700 bp) ribosomal RNA bands on the blots as detected by methylene blue staining.

Example 7

Detection of mRNA Coding for Immunouglobulin Heavy and Light Chains in the Transgenic Plants The presence of mRNA coding for immunoglobulin heavy chain or immunoglobulin light chain gene in the transgenic plants and hybrid progeny was demonstrated by analyzing RNA extracted from the transgenic plants using procedures similar to those described by Molecular Cloning, A Laboratory Manual, supra. Briefly, RNA was extracted from 1 g of mature leaf tissue harvested from either the heavy chain gene transformants, the light chain gene transformants or the hybrid progeny. The leaf tissue was cut into small pieces and admixed to 10 ml of a solution containing 10 ml of 0.1 M Tris-Cl at pH 9.0 and phenol saturated with this buffer. The leaf tissue was immediately homogenized in the solution using a Polytron homogenizer at high speed for 1 minute. The homogenate was centrifuged at 4,000×g for 15 minutes at room temperature. The resulting aqueous phase was recovered and the RNA precipitated by admixing 1 ml of 3 M sodium acetate at pH 5.2 and 25 ml of isopropanol. This solution was maintained at −20 C. for 20 minutes to precipitate the RNA present. The precipitated RNA was collected by centrifuging this solution at 4,000×g for 15 minutes at 4 C. The resulting RNA pellet was resuspended in 400 µl of DEPC—H$_2$O and transferred to a 1.5 ml Eppendorf tube. This solution was centrifuged in an Eppendorf microfuge for 5 minutes at top speed. The resulting supernatant was transferred to a new eppendorf tube and 40 µl of 3 M sodium acetate at pH 5.2 and 1 ml of absolute ethanol admixed to it. This solution was maintained at −20° C. for 20 minutes and then centrifuged for 5 minutes in an eppendorf microfuge. The resulting RNA pellet was resuspended in 400 µl of DEPC—H$_2$O and a small aliquot removed to determine the RNA concentration by absorbance at 260 nm. The remainder of the solution was frozen at −70° C. until used.

The RNA prepared above was size fractionated on denaturing formaldehyde agarose gels and transferred to nylon membrane. The procedures used were similar to the procedures described in *Molecular Cloning A Laboratory Manual*, Maniatis et al., eds., Cold Spring Harbor Laboratories, Cold Spring Harbor, N.Y. (1982). Briefly, the denaturing formaldehyde agarose gel was prepared by melting 1.4 g of agarose in 73.3 ml of DEPC—H$_2$O water and cooling this solution to 60 C. in a water bath. 10 ml of a buffer containing 50 mM NaH$_2$PO$_4$, 50 mM Na$_2$HPO$_4$, 50 mM sodium acetate and 10 mM EDTA was admixed to this solution. 16.66 ml of 37% formaldehyde was also admixed to the solution and the solution poured into a gel mold and allowed to solidify. The denaturing formaldehyde agarose gel was now ready for use.

A 20 µg aliquot of RNA prepared above was admixed to 15 µl of formamide, 5 µl of 37% formaldehyde and 3 µl of a buffer containing 50 mM Na$_2$HPO$_4$, 50 mM Na$_2$HPO$_4$, 50 mM sodium acetate and 10 mM EDTA. This solution was maintained at 55 C. for 15 minutes and then immediately placed on ice. One/tenth volume of a solution containing 50% glycerol 1 mM EDTA 0.4% bromophenol blue and 0.4% xylene cyanol was thoroughly admixed to this solution and the solution loaded onto the denaturing formaldehyde gel prepared above. The gel was electrophoresed in a buffer containing 5 mM NaH$_2$PO$_4$, 5 mM Na$_2$HPO$_4$, 5 mM sodium acetate and 1 mM EDTA for 2 hours at room temperature. After the electrophoresis was complete the gel was soaked in several changes of water for 10 to 15 minutes. The gel was then placed in a solution containing 0.1 M Tris-Cl at pH 7.5 for 45 minutes. The gel was then placed in a solution containing 3 M NaCl and 0.3 M sodium citrate at pH 7.0. The gel was then placed on a thick wick soaked with a solution containing 1.5 M NaCl and 0.15 M sodium citrate at pH 7.0. A sheet of nylon membrane (Hybond-N, Amersham Corporation, Arlington Heights, Ill.) that had been previously cut to the same size as the gel and soaked in a solution containing 10× SSC was placed on the gel and any intervening air bubbles removed. Two pieces of Whatman MM paper, cut to exactly the same size as the nylon membrane were soaked in 2×SSC (0.3 M NaCl and 0.03 M sodium citrate at pH 7.0) and placed on top of the nylon membrane and any intervening air bubbles removed. A stack of paper towels (5–8 cm high) cut to a size just slightly larger than the Whatman 3 MM paper was placed on the top of the Whatman 3 MM paper. A glass plate was placed on top of the resulting stack in a 500 g weight placed on top of the plate. The resulting capillary action was allowed to proceed for 12 to 24 hours and this action transferred the RNA from the gel to the nylon membrane. The stack was disassembled and the nylon membrane soaked in 6×SSC (0.9 M NaCl and 0.09 M sodium citrate at pH 7.0) at room temperature for 5 minutes. The nylon membrane was then placed on a ultraviolet radiation box for 10 minutes to operatively link the RNA to the nylon membrane.

Figure 4:
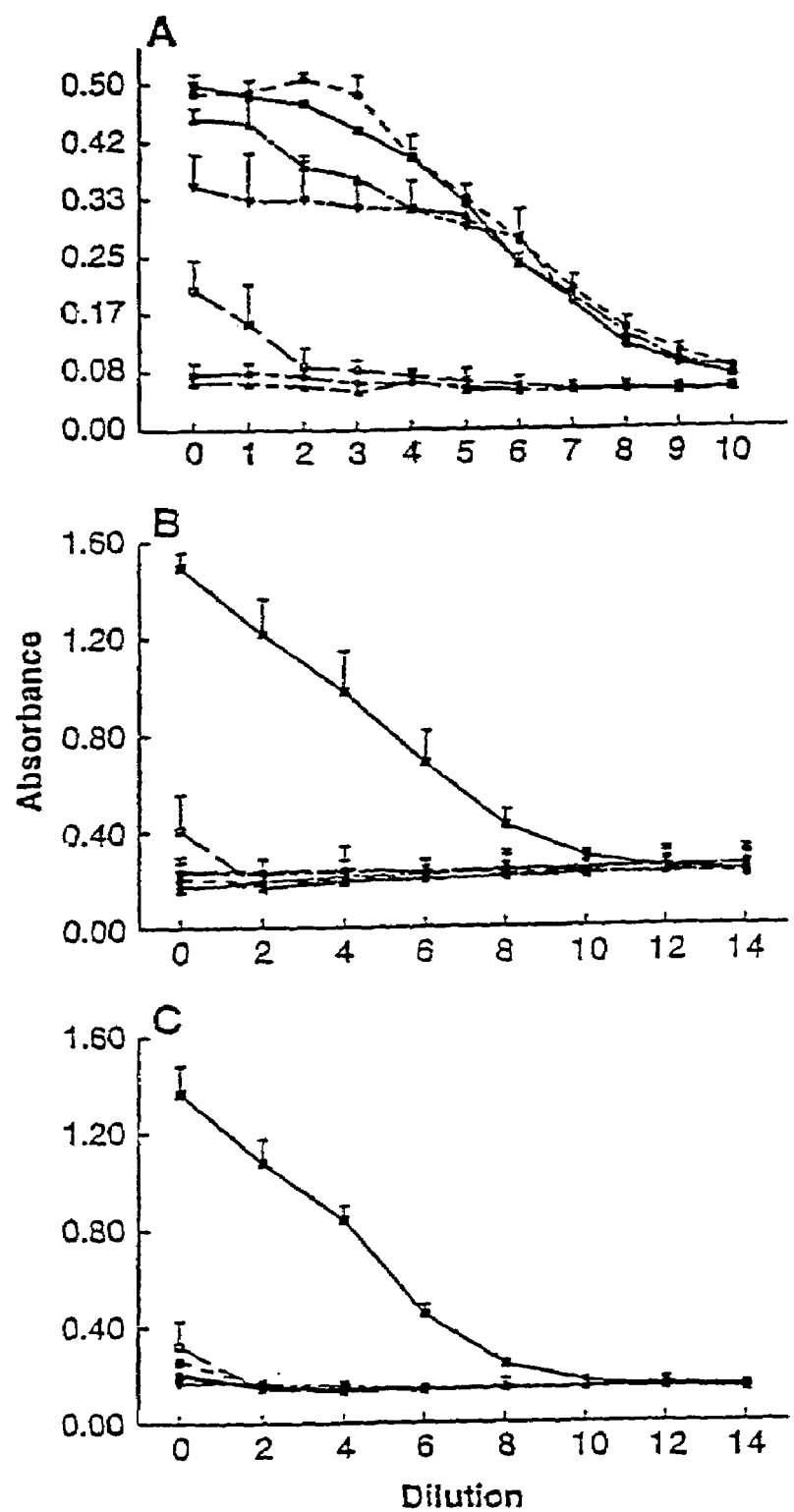
FIGS. 4A–4C illustrate the demonstration of functional antibody expression in transgenic *Nicotiana tabacum* as measured by absorbance at 405 nm ($A_{405}$). In all three figures, Guy's 13 hybridoma cell culture supernatant (IgG) was used as a positive control. The initial concentration of each antibody solution was 5 µg/ml. Dilution numbers represent serial double dilutions. Illustrated results are expressed as the mean±SD of three separate triplicate experiments. In all three figures, the solid squares (a) represent SigA-G; solid circles (●) represent dIgA-G; solid triangles (▲) represent IgA-G; open squares (a) represent SC; open circles (O) represent J chain; open triangles (A) represent WT; and inverted, closed triangles (T) represent Guy's 13. Dilution is plotted on the horizontal axis, while absorbance is plotted on the vertical axis.

RNA containing either kappa light chain coding sequences or gamma heavy chain coding sequences was detected by prehybridizing and hybridizing the nylon membrane using the protocol described in Example 6. (The results of the autoradiogram are illustrated in FIG. 4 of U.S. Pat. No. 5,202,422.) The hybridizing RNA species detected in RNA from transformants expression either the kappa light chain cDNA without a leader sequence (Lane 1) or with its native leader sequence (Lane 3) are shown. The hybridizing RNA species detected in RNA from transformants expressing either the gamma heavy chain cDNA without a leader sequence (Lane 2) or its native leader sequence (Lane 4) are shown. The hybridizing RNA species detected in hybrid progeny containing both kappa light chain with its native leader and gamma heavy chain with its native leader (Lane 5) are shown.

Example 8

Detection of Immunoglobulin Heavy and Light Chains in the Transgenic Plants

The expression of immunoglobulin heavy and light chains in the transgenic plants and hybrid progeny was demonstrated by Western blotting in which both heavy and light chains were detected. Using the Western blot procedure described in *Antibodies: A Laboratory Manual*, Harlow & Lane, eds., Cold Spring Harbor Laboratories, New York (1988). Briefly, 1 g of leaf segments mature plants were homogenized in a mortar and pestle with 1 ml of 0.05 M Tris-Cl at pH 7.5, and 1 mM phenylmethylsuflonyl fluoride (PMSF) μl of the resulting leaf extract was admixed to a solution with a final concentration of 4 M urea and 1% SDS with or without 2 mM D.T. as indicated and the solution boiled for 3 minutes. After boiling this solution was electrophoresed through a 10% polyacrylamide gel containing SDS (SDS-PAGE) as described in NH. Chua, *Methods in Enzymol*, 69: 434–446 (1980). The electrophoresed proteins were then transferred (affixed) to a sheet of nitrocellulose as described in *Antibodies: A Laboratory Manual*, Harlow and Lane, eds., Cold Spring Harbor Laboratory, Cold Spring Harbor, N.Y. (1988). Briefly, the nitrocellulose sheet was placed in a solution containing 20 mM Tris-Cl at pH 8.0, 150 mM NaCl and 0.01% polyoxyethylene sorbitan monolaurate (Tween 20) (TBST) containing 5% bovine serum albumin (BSA) and 0.5% non-fat dried milk. The nitrocellulose sheet was maintained in this solution for 6 hours at 4 C. The nitrocellulose was then placed in a solution containing a 1:500 dilution of a biotinylated goat anti-mouse whole IgG antibody (Cappel, Malvery, Pa.) in TBST and the solution containing the nitrocellulose sheet maintained at 4 C. for 24 hours. During this time, the immunoglobulin heavy chains and the immunoglobulin light chains immobilized on the nitrocellulose sheet immunoreacted with the biotinylated goat anti-mouse whole IgG antibody to form a immunoreaction product on the nitrocellulose sheet. The nitrocellulose sheet was removed from this solution and washed with TBST solution and then placed in a TBST solution containing streptavidin-conjugated alkaline phosphatase (Fisher Scientific, Pittsburgh, Pa.). This solution was maintained for 1 hour at 25 C. The nitrocellulose sheet was removed from this solution and washed with TBST.

The immunoreaction product was visualized by maintaining the nitrocellulose sheet in a solution containing 100 mM Tris-Cl at pH 9.5, 100 mM NaCl, 5 mM $MgCl_2$, 0.3 mg/ml of nitro blue tetrazolium (NBT) and 150 Hg/ml 5-bromyl-4-chloryl-3-indolyl phosphate (BCIP) for 30 minutes at room temperature. The residual color development solution was rinsed from the filter with a solution containing 20 mM Tris-Cl at pH 7.5 and 150 mM NaCl. The filter was then placed in a stop solution consisting 1 mM EDTA, pH8. The development of an intense purple color indicated the location of the immunoreaction products.

Figure 5:
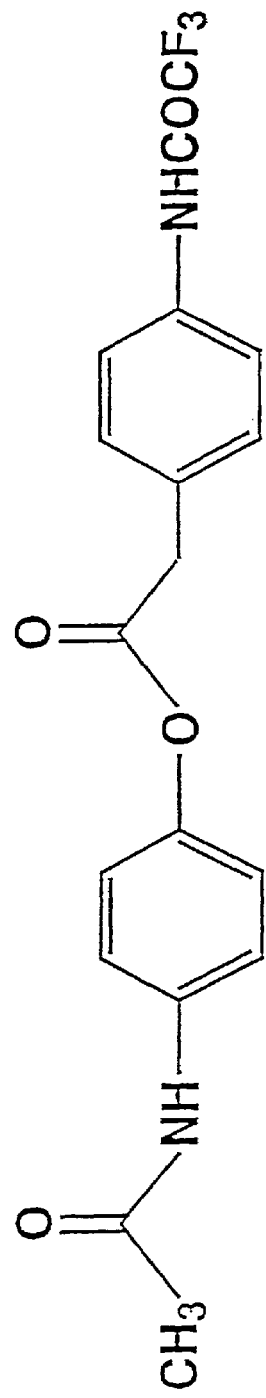
FIG. 5 illustrates the substrate (1) and inhibitor (2) used to demonstrate the 6D4 antibody produced in tobacco plants functions to catalyze the substrate (1).
Figure 5:
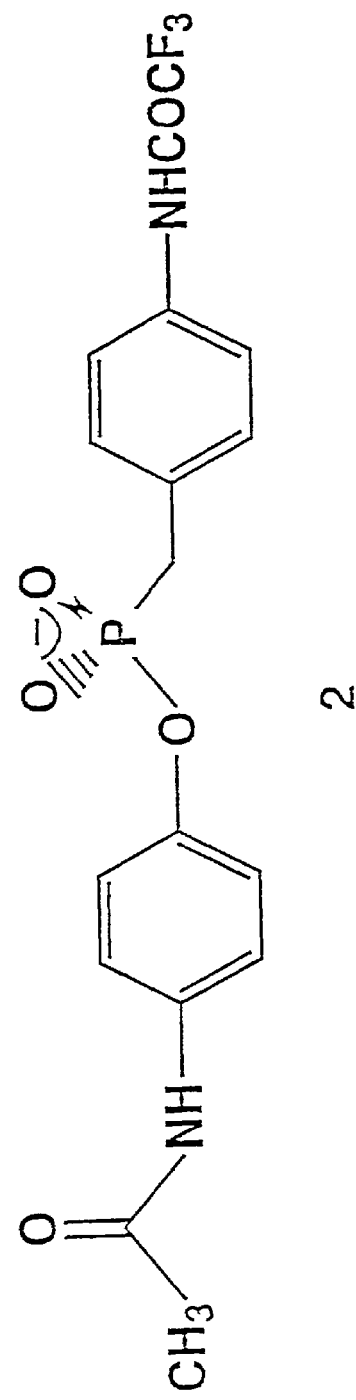

Expression of immunoglobulin heavy chain in the heavy chain transformants, immunoglobulin light chain in the light chain transformants and both immunoglobulin heavy and light chains in the hybrid progeny was demonstrated using the Western blot (not shown here; but see FIG. 5 of U.S. Pat. No. 5,202,422). In addition, the immunoglobulin heavy and light chains produced in the hybrid progeny were assembled into immunoglobulin molecules as evidenced by the high molecular weight immunoreactive gamma and kappa chain seen under non-reducing conditions (not shown).

The description of the aforementioned Western blot is as follows. A Western blot of leaf proteins was prepared using samples from transgenic tobacco plants expressing immunoglobulin kappa chains, immunoglobulin gamma chains, or assembled immunoglobulin IgG. In Lanes 1–7 the leaf protein extracts contained dithiothreitol (DTT) and in Lanes 8 and 9 the leaf protein extracts did not contain DTT. Lane 1 contained 100 ng of purified antibody from the 6D4 hybridoma. Lane 2 contained 15 ug of wild type plant extract protein. Lane 3 contained 15 ug of protein from a plant transformed with truncated kappa chain cDNA (pHi102) containing no leader sequence. Lane 4 contained 15 ug of plant extract from a plant transformed with truncated gamma chain cDNA (pHi102). Lane 5 contained 15 ug of plant extract from a full length kappa cDNA transformant (pHi102). Lane 6 contained 15 ug of plant extract from a full length gamma chain cDNA transformant (pHi202). Lane 7 contained 15 ug of plant extract from an F1 plant derived from a cross between kappa and gamma transformants. Lane 8 contained 100 ng of 6D4 antibody (no DTT); Lane 9 was the same as lane 7 except no DTT was present in the sample. Gamma and kappa on the left referred to the positions of the 6D4 heavy and light chains.

Example 9

Immunoglobulin Molecules Expressed in the Transgenic Plants Bind Antigen

The binding of antigen by the immunoglobulin molecules expressed in the transgenic plants was demonstrated using an ELISA assay similar to the ELISA assay described in Example 4. This antigen binding ELISA assay was modified in the following manner. Instead of adhering the goat antibodies to the microtitre well walls, the antigen P3 conjugated to BSA according to the methods described in Tramontano et al., *Proc. Natl. Acad. Sci. USA.* 83: 6736–6740 (1986), was adhered to the microtitre well walls. Leaf homogenate from each of the plantlet populations were then added to the wells and the binding of the immunoglobulin molecules present in the homogenate detected using goat anti-mouse heavy chain conjugated to HRPO as described in Example 4.

The immunoglobulin molecules expressed in the transgenic plant directly bound their specific antigen, P3 in this antigen binding ELISA assay. To demonstrate the specificity of this antibody antigen interaction, an additional competitive ELISA assay was performed. This assay was similar to the antigen binding ELISA assay described above except that before the serial dilutions of leaf homogenate, 5 µl of a 500 µM solution of P3 was added to a duplicate well to act as a competitor for antibody binding to P3-BSA adhered to the microtitre well walls. The remainder of this competition ELISA assay was carried out according to Example 4.

The interaction between the antibodies expressed in the transgenic plants and their specific antigen, P3, was specifically inhibited by free antigen in this competition ELISA assay.

Example 10

Catalytic Activity Immunoglobulin Expressed in Transgenic Plants

The catalytic activity of immunoglobulin molecules expressed in transgenic plants was demonstrated by purifying the 6D4 immunoglobulin molecule from tobacco plants expressing the functional immunoglobulin and assaying the purified immunoglobulin molecule to measure catalytic activity.

Briefly, plants containing assembled immunoglobulin molecules were produced using the method and procedures described in Examples 1, 2, 3, 4, 5, 6 and 8. The 6D4 immunoglobulin molecule was selected for expression in plants because a normally glycosylated 6D4 antibody produced in mice catalyzes the hydrolysis of carboxylic esters. See Tramontano et al., *Science.* 234: 1566 (1986).

The 6D4 immunoglobulin was purified from the leaves of a tobacco plant expressing the immunoglobulin by sephacryl fractionation and absorption to Protein A-Sepharose. Briefly, midveins were removed from 10 grams (g) of young leaves which were then homogenized by hand in 50 ml of a homogenation buffer containing 50 mM of Tris-Hcl at pH 8.0 and 1 mM PMSF. The resulting homogenate was centrifuged at 10,000×g and the resulting supernatant concentrated to a final volume of 10 ml using a Centricon 30 (Amicon, Danvers, Mass.). The concentrated homogenate was then loaded onto a previously prepared sephacryl S-300 column. The column was eluted with 0.1 M sodium acetate at pH 5.0 and 1 ml fractions of eluate collected. The amount of immunoglobulin present in each of the collected fractions was determined using the ELISA assay described in Example 4.

The fractions containing the majority of the eluted immunoglobulin were pooled and extensively dialyzed against a binding buffer containing 1.5 M glycine at pH 8.9 and 3.0 M NaCl. After dialysis, the immunoglobulin was slowly passed twice over a column containing 2 g of protein A-Sepharose (Pharmacia, Piscataway, N.J.) to allow the immunoglobulin to bind to the column. The protein A-SEPHAROSE was washed with 20 ml of binding buffer. The bound immunoglobulin was eluted with 10 ml of elution buffer containing 0.1 M citrate at pH 6.0. The eluate was concentrated to 50 ug of immunoglobulin per ml using a Centricon 30. The concentrated immunoglobulin was then dialyzed against a 50 mM phosphate buffer at pH 8.0. The final concentration of immunoglobulin present in the resulting solution was determined using an ELISA assay described in Example 8.

The amino acid sequence of the resulting 6D4 immunoglobulin was determined using the methods described by Matsudaira, P., *J. Biol. Chem.* 262: 10035–10038 (1987). Briefly, the gamma heavy chain and kappa light chain of the 6D4 immunoglobulin were separated using sodium dodecyl sulfate-polyacrylamide gel electrophoresis (SDS-PAGE) by loading approximately 1 ug of 6D4 immunoglobulin onto a 10% polyacrylamide gel. The immunoglobulin was electrophoresed until the gamma heavy chain and Kappa light chain were separated. The separated gamma heavy chain and kappa light chain were then blotted onto a polyvinylidene difluoride membranes as described by Matsudaira, P., *J. Biol. Chem.*, 262: 10035–10038 (1987) and the amino acid sequence determined.

Mouse derived 6D4 monoclonal antibody was purified from mouse ascites using the same procedure as that used to purify the antibody from plant leaves. Briefly, the mouse derived ascites fluid containing the 6D4 monoclonal antibody was fractionated on a Sephacryl (S-300) column and a protein A-SEPHAROSE column. The resulting purified mouse monoclonal 6D4 antibody was at a final concentration of 500 ug/ml in a 0.1 m citrate, pH 6.0 buffer containing.

The plant derived and mouse derived 6D4 antibodies were assayed for catalytic activity by incubating the purified antibodies with a substrate in the presence of absence of a specific inhibitor as previously described by Tramontano et al., *Science* 234: 1566–1569 (1986). Briefly, approximately 100 nM of mouse derived 6D4 antibody or plant derived 6D4 antibody was preincubated at 25° C. in 50 mM phosphate buffer at pH 8.0. A series of reaction admixtures were formed by admixing varying amounts of dioxane stock solution containing substrate to produce a series of reaction admixtures containing 5% dioxane and a substrate concentration ranging from 1 to 8 mM. The reaction admixtures were maintained for 1 hour at 25° C. and the hydrolysis of the ester substrate measured on a Hewlett-Packard 8452A diode array spectrophotometer by monitoring the adsorption change at 245 nanometers (nm). The maximum adsorption change was measured by adding a non-specific esterase (Sigma, St. Louis, Mo.) to a control reaction admixture. The kinetic parameters were obtained after subtraction of background hydrolysis, using the Lineweaver-Burke data treatment described by Tramontano et al., *Science.* 234: 1566 (1986). The inhibition constants were determined by plotting the slopes obtained with both 100 nM and 300 nM phosphonate (Table 6).

The catalytic activity of the purified plant derived and mouse derived 6D4 antibodies as measured by $K_M$, $K_I$, $V_{max}$, and $K_{cat}$, is shown in Table 6. The plant derived and mouse derived 6D4 antibodies differed by less than one order of magnitude.

TABLE 6

Catalytic Activity of 6D4[b].

| Source | Tobacco | Ascites |
|---|---|---|
| $K_M$ | $1.41 \times 10^{-6}$ M | $9.8 \times 10^{-6}$ M |
| $v_{max}$ | $0.057 \times 10^{-8}$ M sec$^{-1}$ | $0.31 \times 10^{-8}$ M sec$^{-1}$ |
| $K_I$ | $0.47 \times 10^{-6}$ M (competitive) | $1.06 \times 10^{-6}$ M (competitive) |
| $k_{cat}$ | 0.008 sec$^{-1}$ | 0.025 sec$^{-1}$ |

[b]This data was analyzed using a linear regression.

Example 11

Production of Immunoglobulin with Heterologous Leader Sequences in Plants

To determine the effects of a heterologous leader sequence on immunoglobulin assembly in plants, an immunoglobulin cDNA containing the signal and pre-sequence from the α-mating factor of *Saccharomyces cerevisiae* in place of the native mouse leader sequences described in Example 1 was prepared. The sequence of the α-mating factor of *Saccharomyces cerevisiae* has been described by Kurzan et al., Cell 30: 933–943 (1982) and is described as follows.

The sequence of the alpha-mating factor leader sequence was coupled to a nucleotide sequence encoding either the gamma chain or the or kappa chain. The nucleotide sequence of the a mating factor is as follows: GAATTCATTCAA-GAATAGTTCAAACAAGAAGATT ACAAACTAT-CAATTTCATACACAATATAAACGATTAAAAGA (SEQ ID NO. 9). The underlined symbols represent the 5' untranslated nucleotides of the yeast pre-pro sequence.

The translated amino acid residue sequence of the translated portion of the pre-pro sequence and the initial portion of the attached kappa chain was as follows: MRFPSIFTAV-LFAASSALAAPVNTTTDETAQIPAEAVI-GYSDLEGDFDVAVLPFSNSTNNGL LFINTTIASIAA-KEEGVSLDLKR/DVVL . . . (SEQ ID NO. 10). The translated amino acid residue sequence of the translated portion of the pre-pro sequence and the initial portion of the attached gamma chain was as follows: MRFPSOFTAVL-FAASSALAAPVNTTTEDETAQ IPAEAVIGYSDLEGD-FDVAVLPFSNSTNNGLLFINTTIASIAA-KEEGVSLDLKR/EVEL . . . (SEQ ID NO. 11). The junction point between the pre-pro sequence and the kappa or gamma chain is denoted by a virgule ("/"); the four amino acid residues following the virgule represent the initial portion of the kappa and gamma chains, respectively.

Briefly, the pre-pro sequence from the *Saccharomyces cerevisiae* α-mating factor described by Kurzan et al., Cell 30: 933–943 (1982) was subcloned into M13 mp18 by first isolating the Eco RI to Hind III restriction endonuclease fragment containing the α-mating factor from p69A. This α-mating factor containing restriction endonuclease fragment was then ligated to M13 mp18 vector DNA that had been previously digested with Eco RI and Hind III restriction endonucleases. The accuracy of this cloning step was determined by restriction endonuclease digestion of the resulting M13 clones containing the α-mating factor DNA.

The 6D4 kappa and gamma chain vectors without endogenous mouse leader sequences prepared in Example 1, were digested with Hind in and the resulting 5' phosphate groups removed. The α-mating factor vector was digested with Hind III restriction endonuclease to produce a Hind III restriction endonuclease fragment containing the α-mating factor. The α-mating factor containing restriction endonuclease fragment was isolated using an electroeluter (BRL, Bethesda, Md.) after separation by agarose gel electrophoresis.

The isolated α-mating factor containing restriction endonuclease fragment was ligated to the Hind III digested gamma and kappa vectors in separate ligation reactions. Oligonucleotide-directed mutagenesis was used to remove the surplus nucleotides between the end of the α-mating factor pre-pro sequence and the Gln codon (gamma chain) or the Asp codon (kappa chain) to produce chimeric cDNAs. The accuracy of the oligonucleotide-directed mutagenesis was confirmed by DNA sequencing.

The chimeric cDNA's containing the α-mating factor pre-pro sequence and either the gamma or kappa immunoglobulin coding sequence were inserted into the PMON530 vector described by Rogers et al., Meth. Enzymol., 153: 253 (1987). Briefly, the chimeric cDNAs were attached to the pMON530 vector using the T4 DNA ligase. The products of the ligation reaction were introduced into *E. coli* using the bacterial strain and methods of Bethesda Research Laboratories (Bethesda, Md.). Individual plasmids (recombinant pMON530 containing the chimeric cDNA) were analyzed by restriction endonuclease digestion and sequencing.

The resulting chimeric gamma and kappa cDNA expression vectors were used to transform leaf discs as described by Horsch et al., Science, 227: 1229–1231 (1985) and in Example 4.

Individual plants expressing the gamma chain and individual regenerated plants expressing the kappa chain were selected. After confirming that the regenerates expressed either gamma or kappa chain using the ELISA described in Example 4, the individual regenerates were sexually crossed to produce a gamma X kappa progeny. These progeny were screen for antibody production using the ELISA assay described in Example 4.

The individual regenerates expressing either the gamma$_{mat}$ chain or the kappa$_{mat}$ chain were crossed with plants expressing the native 6D4 antibody containing the endogenous mouse leader peptide to produce progeny containing the native gamma chain and the kappa$_{mat}$ or progeny containing the gamma$_{mat}$ and the native kappa chain. These progeny were also screened using the ELISA assay described in Example 4.

The level of antibody expression in each of these progeny was determined using the ELISA assay described in Example 4 and the results are reported in Table 7.

TABLE 7

Accumulation of Gamma or Kappa Chains and Antigen Binding of Gamma/Kappa Complexes.

| gamma mat[a] | kappa mat |
|---|---|
| 743 ± 260 (1030) | 48 ± 8 (72) |
| gamma mat (kappa mat)[c] | kappa mat (gamma mat) |
| 2410 ± 1230 (7700) | 2280 ± 1300 (7700) |
| gamma mat (kappa mouse) | kappa mat (gamma mouse) |
| 2615 ± 1505 (8300) | 2490 ± 1175 (8300) |

TABLE 7-continued

Accumulation of Gamma or Kappa Chains
and Antigen Binding of Gamma/Kappa Complexes.

| gamma mat (kappa NL) | kappa mat (gamma NL) |
|---|---|
| 705 ± 300 | 38 ± 8 |
| (0) | (0) |

*Values are expressed in ng/mg total protein (mean ± S.E.) where purified 6D4 antibody from mouse ascites was used as the ELISA standard. Numbers in parenthesis are highest levels of expression. "NL" identifies leaderless/signalless sequences.
°α(K) refers to the abundance of α chain in a plant which also expresses K chain and vice versa (i.e. progeny of sexual cross) as measured by ELISA. In these cases, values in parentheses are the result of antibody binding to ELISA plates coated with the phosphonate antigen (P3) (previously described by Tramontano et al., Proc. Natl. Acad. Sci., USA 83: 6736–6740 (1986)) conjugated to BSA Hiatt et al., Nature 342: 76–78 (1989). Only plants expressing the highestlevels of K complex were used in the antigen binding assays.

The individual gamma and kappa chains containing the Saccharomyces cereviseae leader sequence accumulated at nearly the same levels as constructs expressing the native mouse leader that were previously reported in Hiatt et al., Nature, 342: 76–78 (1989). In addition, functional antibody was produced by crossing either gamma and kappa chains containing the same signal (gamma$_{mat}$ X kappa$_{mat}$) or different signals (kappa$_{mat}$ X gamma$_{native}$ X kappa$_{native}$ X gamma$_{mat}$). This is in contrast to crosses of plants in which one parent expressed a immunoglobulin without a leader did ot result in production of functional antibody molecules as reported by Hiatt et al., Nature, 342: 76–78 (1989).

The fidelity of processing of the mouse immunoglobulin N-termini by the plant endomembrane system was determined by automated sequence analysis as described by P. Matsudaisa, J. Biol. Chem., 262: 10035–10038 (1987). Mammalian kappa chains N terminal amino acid is typically aspartic acid as described by Kabat et al., Sequences of Proteins of Immunological Interestl, Public Health Service, National Institutes of Health, Bethesda, Md. Many murine IgG1 gamma chains are blocked by pyroglutanic as reported by Johnston et al., Bioch. Biophys. Res. Commun. 66: 843–847 (1975). Sequence analysis suggested that the gamma chains derived from plants expressing the native mouse leader contained a blocked N-terminus. The end terminal sequence of kappa chains expressing the native mouse leader was Asp-Val-Val-Leu indicating the appropriate proteolytic processing of the kappa chain.

Example 12

Glycosylation of Plant Derived Immunoglobulin Molecules

To determine the gamma chain glycosylation pattern of the plant derived immunoglobulin, the purified antibody was blotted onto nitrocellulose and probed with biotinylated lectins as described by Faye et al., Anal. Biochem. 149: 218–224 (1985). Briefly, the nitrocellulose membranes were incubated in a solution of 50 mM Tris-Cl, 0.5 m NaCl, 0.1 mM CaCl$_2$, 0.1 mM MgCl$_2$, and 0.1 mM (TIBS) containing 1 ug/ml of a biotinylated lectin (Pierce, Rockford, Ill.) at room temperature for one hour. The filters were then washed with TIBS and incubated in TIBS containing 1 ug/ml streptavidin-alkaline phosphatase (Sigma, St. Louis, Mo.) for 1 hour at room temperature. The bound alkaline phosphatase was visualized using bromo-chloro-indolyl phosphate as described by Hiatt et al., Nature, 342: 76–78 (1989).

In some cases, the purified antibody was incubated with 40 milliunits of endoglycosidase H (Signal Chemical Co., St. Louis, Mo.) in 50 ul of 200 mM sodium acetate at pH 5.8 for 2 hours at 37° C. prior to blotting to remove high mannose type sugars.

The results (not shown) indicated that only Concanavalin A, specific for mannose and glucose bound to the plant-derived antibody whereas the mouse ascites-derived antibody was recognized by Concanavalin A as well as the lectins from the Ricinus communis, specific for terminal galactose residues (N-acetylgalactosamine), and to a lesser extent by wheat germ agglutinin that is specific for N-acetylglucosamine dimers having terminal sialic acid residues. The specificity of the various lectins is discussed in Kijimoto-Ochiai et al., Biochem. J., 257: 43–49 (1989). The lectins from Datura stramonium specific for N-acetylglycosamine oligomers and N-acetyl lactosamine and the lectin from Phaseolus vulgaris that is specific for Gal β1, 4 GlcNac β1, 2 mannose, did not bind to either the plant or mouse ascites derived gamma chain.

The elution of the lectins from the nitrocellulose blots using α-methylglucoside was used to compare the relative affinity of Concanavalin A binding to the plant-derived and mouse ascites derived antibodies as has been previously described by Johnston et al., Bioch. Biophys. Res. Commun., 66: 843–847 (1975). Using this assay, the plant-derived and mouse ascites-derived antibodies are indistinguishable with regards to Concanavalin A affinity as well as the quantity of Concanavalin A binding per microgram of gamma chain.

Digestion of either the plant-derived or mouse ascites-derived antibodies with endoglycosidase H using the conditions described by Trimvle et al., Anal. Biochem. 141: 515–522 (1984) was carried out and the antibodies then transferred to nitrocellulose. The antibodies digested with endoglycosidase H displayed no reduction in Concanavalin A binding under conditions where Concanavalin A binding to ovalbumin was diminished.

Taken together these results indicate that the plant-derived immunoglobulin is processed through similar cellular compartments as the mouse ascites-derived antibody. The gamma chain Concanavalin A binding and resistance of the glycan to digestion by endoglycosidase H as well as the correct kappa chain N-terminus indicate that the antibody is migrating from the endoplasmic reticulum to the Golgi and is being secreted through the plasma membrane as described by Walter et al., Annu. Rev. Cell. Biol. 2: 499–516 (1986).

The differential binding of several of the lectins to the plant-derived antibody indicates that the final glycosylation pattern of the plant-derived antibody and the mouse ascites-derived antibody are different. The plant-derived antibody did not bind to the lectins specific for terminal galactose and terminal sialic acid whereas the mouse ascites-derived antibody did.

Example 13

Retention of Immunoglobulin Molecules within the Plant Cell Wall

The rate of secretion of immunoglobulins from plants protoplast that did not contain cell walls was compared to the rate of secretion of immunoglobulin from plant cells having intact cell walls. The preparation of protoplasts from plant cells has been described by Tricoli et al., Plant Cell Resort, 5: 334–337 (1986). Briefly, 1 cm$^2$ pieces of tobacco leaf are incubated for 18 hours in a mixture of cellulysin (Calbiochem), macerase (Calbiochem) and driselase (Sigma) to digest cell walls and release protoplasts from the leaf. The protoplasts are purified by centrifugation (100×g for 2 minutes) in 0.4 m Mannitol.

The immunoglobulin produced by either protoplast or intact plant cells was labeled by resuspending 2×10$^6$ protoplasts in 0.5 ml of a mannitol media containing and 10 uCi mCi of $^{35}$S-methionine. The cells were maintained in this labeling medium for 2 hours and an aliquot of cells and medium was removed to determine the incorporated of labeled methionine into the 6D4 antibody. The amount of labeled 6D4 antibody in the incubation media was determined by adhering the immunoglobulin contained in the medium to a protein-A Sepharose column and determining the total radioactive counts adhering to the column. The amount of labeled methionine incorporated in the cells into the 6D4 antibody was determined by preparing the cells and loading the lysate onto a 10% SDS-PAGE gel and electrophoresing the lysate for 2 hours, as previously described by Hiatt et al., *J. Biol. Chem.* 261: 1293–1298 (1986). The region of the SDS-PAGE gel containing the 6D4 antibody was cut out and the labeled antibody eluded from the gel. The total amount of labeled antibody present was then determined. In addition, the same measurements was made after a further maintenance of 2 hours in the presence of 100 mM methionine.

The callus cell lines were initiated over a period of 8 weeks by incubating leaf segments in the appropriate growth hormones as has been previously described by Hiatt et al., *J. Biol. Chem.* 261: 1293–1298 (1986). The liquid suspensions cell lines were then initiated from clumps of the callus cells and used for the incorporation of $^{35}$S-methionine as described above.

The results of this secretion analysis are shown in Table 8. After a 2 hour labeling period, a significant fraction of newly synthesized antibody was secreted from the protoplast. After a chase of 2 hours with 100 mM methionine, most of the total labeled antibody was secreted from the protoplast into the medium indicating that secretion of the antibody had occurred. In contrast, approximately 40% of the labeled antibody was retained within established callus suspension cell lines that had intact cell walls. These cells contain thin, primary cells walls and therefore retained the antibody within the cell wall.

TABLE 8

| 35 S-Methionine Incorporation Into 6D4 at 2 Hours (Medium/Cells) | | |
|---|---|---|
| PROTOPLASTS | PROTEIN A | 0.33 |
| " | SDS-PAGE | 0.31 |
| CALLUS SUSPENSION CELLS | PROTEIN A | 0.39 |
| " | SDS-PAGE | 0.25 |
| INCORPORATION INTO 6D4 AFTER 2 HOUR CHASE | | |
| PROTOPLASTS | PROTEIN A | 6.60 |
| " | SDS-PAGE | 6.31 |
| CALLUS SUSPENSION CELLS | PROTEIN A | 2.77 |
| " | SDS-PAGE | 2.14 |

Example 14

Production of a Secretory IgA in a Plant Cell

A. Isolation of Messenger RNA Coding for Pathogen Specific Variable Regions

A secretory IgA immunospecific for a preselected antigen is produced in plant cells by first isolating the variable region coding genes from a preselected hybridoma. Messenger RNA is prepared according to the methods described by Chomezynski et al., *Anal. Biochem.* 162: 156–159 (1987) using the manufacturers instructions and the RNA isolation kit produced by Stratagene (La Jolla, Calif.). Briefly, approximately 1×10$^7$ cells are homogenized in 10 ml of a denaturing solution containing 4.0 M guanine isothiocyanate, 0.25 M sodium citrate at pH 7.0, and 0.1 M 2-mercaptoethanol using a glass homogenizer. One ml of sodium acetate at a concentration of 2 M at pH 4.0 is admixed with the homogenized cells. One ml of water-saturated phenol is admixed to the denaturing solution containing the homogenized cells. Two ml of a chloroform: isoamyl alcohol (24:1 v/v) mixture is added to the homogenate. The homogenate is nixed vigorously for 10 seconds and is maintained on ice for 15 minutes. The homogenate is then transferred to a thick-walled 50 ml polypropylene centrifuge 2 (Fisher Scientific Company, Pittsburgh, Pa.). The solution is centrifuged at 10,000×g for 20 minutes at 4 C. the upper RNA-containing aqueous layer is transferred to a fresh 50 ml polypropylene centrifuge 2 and is mixed with an equal volume of isopropyl alcohol. This solution is maintained at −20 C. for at least 1 hour to precipitate the RNA. The solution containing the precipitated RNA is centrifuged at 10,000×g for 20 minutes at 4C. The pelleted total cellular RNA is collected and is dissolved in 3 ml of the denaturing solution described above.

Three ml of the isopropyl alcohol is added to the resuspended total cellular RNA and is vigorously mixed. This solution is maintained at −20 C. for at least 1 hour to precipitate the RNA. The solution containing the precipitated RNA is centrifuged at 10,000×g for 10 minutes at 4 C. The pelleted RNA is washed once with a solution containing 75% ethanol. The pelleted RNA is dried under vacuum for 15 minutes and then is re-suspended in dimethyl pyrocarbonate treated (DEPC—H$_2$O)H$_2$O.

The messenger RNA (mRNA) prepared above is enriched for sequences containing long poly A tracks as described in *Molecular Cloning: A Laboratory Manual, Second Edition*, Sambrook et al., eds., Cold Spring Harbor, N.Y. (1989). Briefly, one half of the total RNA isolated from the hybridoma cells is resuspended in 1 ml of DEPC—H$_2$O and is maintained at 65 C. for 5 minutes. One ml of 2× high salt loading buffer consisting of 100 mM Tris-HCl, 1 M sodium chloride, 2.0 mM disodium ethylene diamine tetraacetic acid (EDTA) at pH 7.5, and 0.2% sodium dodecyl sulphate (SDS) is added to the resuspended RNA and the mixture is allowed to cool to room temperature. The mixture is then applied to an oligo-dT (Collaborative Research Type 2 or Type 3) column that is previously prepared by washing the oligo-dT with a solution containing 0.1 M sodium hydroxide and 5 mM EDTA and is then equilibrated in DEPC—H$_2$O. The column eluate is collected in a sterile polypropylene tube and is reapplied to the same column after heating the eluate for 5 minutes at 65 C. The oligo-dT column is then washed with 2 ml of high salt loading buffer consisting of 50 mM Tris-HCl at pH 7.5, 500 mM sodium chloride, 1 mM EDTA at pH 7.5 and 0.1% SDS. The oligo-dT column is then washed with 2 ml of 1× medium salt buffer consisting of 50 mM Tris-HCl at pH 7.5, 100 mM sodium chloride, 1 mM EDTA and 0.1% SDS. The messenger RNA is eluded from the oligo-dT column with 1 ml of buffer consisting of 10 mM Tris-HCl at pH 7.5, 1 mM EDTA at pH 7.5 and 0.05% SDS. The messenger RNA is purified by extracting this solution with a phenol/chloroform solution followed by a single extraction with 100% chloroform. The messenger RNA is concentrated by ethanol precipitation and then resuspended in DEPC—H$_2$O and stored at −70 C. until used.

The messenger RNA isolated by the above process contains messenger RNA coding for both the heavy and light chain variable regions that make up the antibody produced by the hybridoma.

B. Isolation of the Variable Regions Using the Polymerase Chain Reaction

In preparation for PCR amplification, the mRNA prepared according to the above examples is used as a template for cDNA synthesis by a primer extension reaction. In a typical 50 µl transcription reaction, 5–10 µg of the hybridoma mRNA in water is first hybridized (annealed) with 500 ng (50.0 pmol) of a 3' VH primer as described by Orlandi et al., *Proc. Natl. Acad. Sci. USA* 86:3833–3937 (1989) at 65 C. for 5 minutes. Subsequently the mixture is adjusted to 1.5 mM dATP, dCTP and dTTP, 40 mM Tris-HCl at pH 8.0, 8 mM $MgCl_2$, 50 mM NaCl, and 2 mM spermidine. Moloney-Murine Leukemia Virus reverse transcriptase (26 units, Stratagene) is added to the solution and the solution is maintained for 1 hour at 37 C.

PCR amplification is performed in a 100 µl reaction containing the products of the reverse transcription reaction (approximately 5 g of the cDNA/RNA hybrid), 300 ng of the 3' VH primer described by Orlandi et al., *Proc. Natl. Acad. Sci. USA*, 86: 3833–3937 (1989). 300 ng each of the eight 5' VH primers also described by Orlandi et al., supra, 200 mM of a mixture of dNTP's, 50 mM KCl, 10 mM Tris-HCl pH 8.3, 15 mM $MgCl_2$ 0.1% gelatin and 2 units of Taq DNA polymerase. The reaction mixture is overlaid with mineral oil and subjected to 40 cycles of amplification. Each amplification cycle involves a denaturation at 92 C. for 1 minute, annealing at 52 C. for 2 minutes and polynucleotide synthesis by primer extension (elongation) at 72 C. for 1.5 minutes. The amplified $V_H$-coding DNA homolog containing samples are extracted twice with phenol-chloroform, once with chloroform, ethanol precipitated and are stored at −70 C. and 10 mM Tris-HCl (pH 7.5) and 1 mM EDTA.

The light chain variable region is isolated in a similar fashion except that a 3' $V_L$ primer and a 5' $V_L$ primer specific for either the lambda or kappa light chain was used. The PCR amplification conditions were identical to those described for the heavy chain variable region isolation.

C. Insertion of the Pathogen Specific Heavy and Light Chain Variable Region into A plant Expression Vector The pathogen specific heavy and light chain variable regions are isolated as described above and are inserted into a plant expression vector containing the constant region of IgA. This vector is constructed using standard molecular biology techniques and is a derivative of pMON 530 that has both the immunoglobulin signal sequence from the 6D4 antibody as described n Example 1 and the immunoglobulin alpha constant region isolated from MOPC 315 that has been fully sequenced and previously described by Auffray et al., *Gene.* 13: 365–374 (1981). This vector also contains a polylinker region position between the immunoglobulin signal sequence and the IgA constant region gene to allow the pathogen specific heavy chain variable region to be easily inserted. The restriction endonuclease sites present in the polylinker are compatible with the restriction endonuclease sites present in the PCR primers used to isolate the heavy chain variable region. The pathogen specific heavy chain variable region is inserted into the vector by cutting the vector with the appropriate restriction enzymes and also cutting the pathogen specific variable region with the appropriate restriction enzymes sites that are present in the PCR primers used to isolate the variable. The pathogen specific variable region is then ligated into the vector.

This vector is then introduced into a plant using the methods described in Example 4. Plants containing the pathogen specific IgA heavy chain are identified and then crossed with plants containing the pathogen specific light chain.

Plants containing the pathogen specific light chain variable region coupled to an appropriate light chain are produced using similar techniques as the pathogen specific heavy chain variable region containing plants.

A sexual cross is used to place the pathogen specific heavy and light chains in the same plant to produce a plant containing an assembled IgA.

Plants containing the secretory component of IgA are produced by introducing the gene coding for the secretory component into a plant expression vector such as the pMON 530 vector. The sequence of the secretory component has been described by Mostov et al., *Nature.* 308: 37 (1984). The secretory component gene is inserted into the pMON 530 vector together with an appropriate signal sequence using standard molecular biology techniques. The resulting secretory component-containing vector is used to transform plant cells and produce plants containing and expressing the secretory component.

Plants containing the J or joining chain of IgA immunoglobulin are produced by inserting the gene coding for the J chain into a plant expression vector as described for the secretory component, the light chain and heavy chain. The J chain gene has been sequenced by Max et al., *J. Exp. Med.* 161: 832–849 (1985). In addition, the sequence of other J chains is available in *Sequences of Proteins of Immunological Interest,* 4th edition, U.S. Dept. of Health and Human Services, (1987). This vector is used to produce plants expressing the J chain.

These J chain expression plants are crossed with the plants expressing the secretory component to produce plants expressing both secretory component and J chain. These plants are then crossed with the plants expressing the pathogen-specific IgA antibody to produce plants expressing true secretory IgA that is made up of two IgA molecules, secretory component and J chain.

D. Production of Passive Immunity to a Selected Pathogen

Plants producing secretory IgA were produced according to Example 11. These plants produced secretory IgA that was immunospecific for a *Shigella* toxin. This secretory IgA was produced by isolating the heavy and light chain variable regions from the hybridoma designated 13 C2 (ATCC #CRL1794). Plants expressing the secretory IgA contained approximately 1 mg of secretory IgA for each 10 to 100 gams of plant material. These plants are harvested and used to produce passive immunity while the plant is still fresh.

Adults in which passive immunity is desired are immunized by ingesting 10 to 100 grams of plants expressing the secretory IgA, 1 to 4 times per day. This immunoglobulin ingestion is carried out for a total of 3 days and then the production of passive immunity is analyzed by ingesting a dose of bacteria containing *Shigella* toxin. The adults ingest approximately $1.2\times10^9$ colony-forming units of the Shigella bacteria suspended in 1 ounce of water containing sodium bicarbonate. Approximately 15 minutes to V2 hour later the adults ingested 10 to 100 grams more of plant containing the secretory IgA.

The adults are monitored for the presence of diarrhea for 1 to 2 days after ingesting the bacteria. The occurrence of diarrhea is greatly reduced in the adults ingesting the plant containing the secretory IgA as compared to other adults who did not ingest the secretory IgA-containing plant but were subjected to the same bacterial challenge.

Plants containing a secretory IgA immunospecific for *Shigella* toxin and *Shigella*-like toxin (SLT1) are prepared by isolating the heavy and light chain variable regions from the hybridoma 13C2 (ATCC #CRL 1794). The plants contain approximately 1 mg of anti-*Shigella* antibody per 10 to 100 grams of plant material. Plants containing the anti-*Shigella* antibody are isolated and homogenized and placed in an infant formula.

Infants are given the equivalent of 6–600 mg of antibody present in the required amount of plant material daily in 3 or more doses as a supplement to their normal feeding. These infants are then followed to determine the incidence of *Shigella* disease in the infants after normal exposure to Shigella bacteria. Infants receiving the plant material containing the secretory IgA specific for *Shigella* toxin have a greatly reduced incidence of disease caused by *Shigella* when compared to infants exposed to the same amount of *Shigella* that did not receive the plant material containing the secretory IgA.

Example 15

Generation and Assembly of Secretory Antibodies

Secretory immunoglobulin A (SIgA) is the most abundant form of immunoglobulin (Ig) in mucosal secretions, where it forms part of the first line of defense against infectious agents. The molecule exists mainly in the 11S dimeric form, in which two monomeric IgA antibody units are associated with the small polypeptide joining (J) chain and with a fourth polypeptide, secretory component (SC). The ability to produce monoclonal SIgA is of substantial value. However, in mammals, two different cell types are required to produce SIgA; the synthesis is complicated because it requires plasma cells secreting dimeric IgA (dIgA) as well as epithelial cells expressing the polymeric Ig receptor (pIgR). In contrast, in plants, only one cell is required for assembly of secretory molecules. Normally, pIgR on the epithelial basolateral surface binds dIgA initiating a process of endocytosis, transcytosis, phosphorylation, proteolysis, and ultimate release of the SIgA complex at the apical surface into the secretion (Mostov, *Ann. Rev. Immunol.* 12: 63 (1994)). Thus, it is important to focus on the ability of transgenic plants to assemble secretory antibodies.

We have also found that it is the heavy chain that "drives" the assembly process, particularly with regard to assembly of secretory immunoglobulins, and that Cα2 and Cα3 are sufficient to allow dimerization of the molecule (data not shown). Although many of the constructs described hereinbelow included heavy and light chain portions, it should be noted that inclusion of light chain sequences is not required. Thus, for example, single-chain antibodies and immunoglobulins containing more than one variable heavy region—are useful as described herein.

A. Preparation of Vectors for Expression of Secretory Antibodies

Genes encoding the heavy and light chains of a murine antibody (Guy's 13), a murine J chain, and a rabbit SC were cloned into a binary 35 S—NOS expression cassette vector, either pMON 530 or pMON 530L, for subsequent transformation of separate transgenic tobacco plants as described below.

Guy's 13 is a murine IgG1 monoclonal antibody (mAb) that recognizes the 185 kD streptococcal antigen (SA) I/II cell surface adhesion molecule of *Streptococcus mutans* and *S. sobrinus* (Smith and Lehner, *Oral Microbiol. Immunol.* 4: 153 (1989)). *S. mutans* is the principal cause of dental caries in humans and SA I/II mediates the initial attachment of *S. mutans* to teeth. SA I/II belongs to a family of streptococcal adhesins and Guy's 13 recognizes a protein epitope that is conserved in all but one of the serotypes of the mutans group of streptococci. Guy's 13 also binds weakly to other oral streptococci. (See Ma, et al., *Eur. J. Immunol.* 24 131–138 (1994). Transgenic full-length Guy's 13 has been generated in *N. tabacum* plants and was found to be correctly assembled (Ma, et al., Id.)

As previously determined, modification of the heavy chain by replacement of its Cγ3 domain with Cγ2 and Cγ3 domains from an IgA-secreting hybridoma (MOPC 315) did not affect the assembly or function of the antibody (IgA-G) produced in transgenic plants (Ma, et al., Id.). The same construct for encoding a hybrid IgA/IgG heavy chain gene was used in the preparation of expressed secretory immunoglobulin molecules as described herein.

The cloning of Guy's 13 heavy and light chain genes was conducted essentially as described in Ma, et al., Id. Briefly, messenger RNA was purified form the Guy's 13 and a murine IgA (MOPC315) hybridoma cell line, using an acid guanidinium thiocyanate-phenol-chloroform extraction (Chomczynski and Sacchi, *Anal. Biochem.* 162: 156 (1987)). Complementary DNA was made using Moloney murine leukemia virus reverse transcriptase (Promega, UK).

DNA encoding the gamma and kappa chains of Guy's 13 were amplified by polymerase chain reaction (PCR). The degenerate oligonucleotides used in the PCR were designed to incorporate a 5'-terminal XhoI, and a 3'-terminal EcoRI restriction site in the amplified DNA fragments. Exemplary oligonucleotides are described in the Detailed Description, the design of which is well known to one of ordinary skill in the art.

Following restriction enzyme digestion, the immunoglobulin light chain encoding DNA was ligated into pMON 530L, a constitutive plant expression vector, which contains a mouse immunoglobulin leader sequence upstream of the cloning site. The pMON530L sequence is derived from pMON 530, a constitutive plant expression vector that includes the cauliflower mosaic virus 35S promoter, described by Rogers et al., *Methods. Enymol.* 153: 253–277 (1987), the disclosure of which is hereby incorporated by reference.

The pMON 530 vector is identical to the parent vector with the exception of a mouse immunoglobulin leader nucleotide sequence encoding the amino acid residue sequence MELDLSLPLSGAAGGT (SEQ ID NO 12) where the nucleotides encoding the last two amino acids are a Kpn cloning site. The inserted leader is in-frame with the endogenous pMON 530 promoter sequence. The recombinant vector containing the inserted light chain sequences was used to transform *E. coli* (DH5-α, Gibco BRL). Transformants were screened by Southern blotting using radiolabeled DNA probes derived from the original PCR products. Plasmid DNA was purified from positive transformants and introduced into *Agrobacterium tumefaciens* (Rogers, et al., *Methods Enzymol.* 153: 253 (1987)). The pMON 530 vector contained native leader sequences and a promoter sequence derived from the $^{35}$S transcript of the cauliflower mosaic virus, which directs expression of transgenes in a variety of cell types of most plant organs (Benfey and Chua, *Science* 250: 959 (1990); Barnes, *PNAS USA* 87: 9183 (1990)). The use of the same promoter for all four transgenes described herein and below maximized the likelihood of coincidental expression in a common plant cell.

A similar approach was used to construct two forms of a hybrid Guy's 13 heavy chain. The synthetic oligonucleotides shown in Table 9 below were used in PCR to amplify the following regions: (a) Guy's 13 signal sequence to the 3' end of Cγ1 domain (J1 and J5); (b) Guy's 13 signal sequence to the 3' end of Cγ2 domain (J1 and J2); and (c) 5' end of Cα2 domain to the 3' terminus of DNA from the MOPC 315 hybridoma (J3 and 34). Primers J2, J3 and J5 incorporate a HindIII site while J1 and J4 respectively incorporate a BglII and XhoI site to facilitate ligation and directional cloning into the expression vector.

The amplified fragments were purified (Geneclean II, Bio 101, La Jolla, Calif.) and digested with HindIII for 1 hour at 37° C. The Guy's 13 fragments were ligated to the MOPC 315 fragment with T4 DNA ligase (Gibco, BRL), at 16° C. for 16 hours, and an aliquot of the reaction mixture was used as template DNA for a further PCR, using the 5' terminal oligonucleotide for Guy's 13 (J1) and the 3' terminal oligonucleotide for MOPC 315 (J4). Amplified DNA fragments were purified and ligated into the pMON 530 vector as described above. Since the DNA encoding the native Guy's 13 leader sequence was included in the PCR amplification for the cloning of the heavy chain chimeric nucleotide sequence, the latter vector was selected for use as it lacked inserted mouse leader sequence present in pMON 530L.

TABLE 9

Synthetic Oligonucleotides

| | | |
|---|---|---|
| J1 | ACCAGATCTATGGAATGGACCTGGGTTTTTC | (SEQ ID NO 13) |
| J2 | CCCAAGCTTGGTTTTGGAGATGGTTTTCTC | (SEQ ID NO 14) |
| J3 | GATAAGCTTGGTCCTACTCCTCCTCCTCCTA | (SEQ ID NO 15) |
| J4 | AATCTCGAGTCAGTAGCAGATGCCATCTCC | (SEQ ID NO 16) |
| J5 | GGAAAGCTTTGTACATATGCAAGGCTTACA | (SEQ ID NO 17) |

The resultant separate expression vectors containing the light and chimeric heavy chain genes were then separately used to transform tobacco plants as described below.

The SC construct used in this study consisted of coding-length cDNA amplified with synthetic oligonucleotide 5' and 3' primers respectively corresponding to the NH$_2$-terminal MALFLL sequence and the AVQSAE sequence near the COOH-terminus of rabbit pIgR (Mostov, et al., Nature 308: 37 (1984)). The 5' and 3' primers were respectively designed to incorporate BglII and EcoRI restriction cloning sites for allowing directional ligation into pMON 530. In addition, the 3' primer was designed to incorporate a stop codon immediately 5' to the EcoRI site and 3' to the codon selected as the arbitrary end of the SC construct. Thus, the 5' and 3' primers had the respective nucleotide sequences, listed in the 5' to 3' direction, GATCTATGGCTCTCTTCTTGCTC (SEQ ID NO 18) and AATTCTTATTCCGCACTCTGCACTGC (SEQ ID NO 19). The restriction sites are underlined.

The rabbit pIgR sequence from which the SC construct was amplified is available through GenBank Accession Number K01291 and listed in SEQ ID NO 20. The primers above respectively amplify the nucleotide region inclusive of positions 124 through 1995 shown in SEQ ID NO 20. This amplified fragment is also listed in SEQ ID NO 21 with a 3' stop codon, TAA, provided. The encoded amino acid sequence thereof is listed in SEQ ID NO 22. The PCR amplified SC fragments including the restriction sites for cloning were then digested with BglII and EcoRI for directional ligation into pMON 530 for subsequent transformation of tobacco plants.

A mouse J chain construct that consisted of coding-length complementary DNA (cDNA) was amplified with synthetic oligonucleotide primers corresponding to the NH$_3$-terminal MKTHLL and the COOH-terminal SCYPD sequences of the mouse J chain (Matsuuchi, et al., PNAS USA 83: 456 (1986)). Mouse J chain constructs may also be prepared using the J chain cDNAs described in Matsuuchi, et al., PNAS USA 83: 456–460 (1986).

As described above for the SC construct, the 5' and 3' primers for the J chain gene were respectively designed to incorporate BglII and EcoRI restriction cloning sites for allowing directional ligation into pMON 530. In addition, the 3' primer was designed to incorporate a stop codon immediately 5' to the EcoRI site and 3' to the codon selected as the arbitrary end of the SC construct. Thus, the 5' and 3' primers had the respective nucleotide sequences, listed in the 5' to 3' direction, GATCTATGAAGACCCACCTGCTT (SEQ ID NO 23) and AATTCTTAGACAGGGTAGCAAGA (SEQ ID NO 24). The restriction sites are underlined.

The immunoglobulin J chain sequence from which the J chain construct was amplified is available through GenBank Accession Number M12555. The PCR amplified J chain cDNA sequence, corresponding to exon 1 through exon 4 of the GenBank sequence, is listed in SEQ ID NO 25 including a 3' TAA codon encoding stop sequence. The encoded amino acid sequence thereof is listed in SEQ ID NO 26. The PCR amplified J chain fragments including the restriction sites for cloning were then digested with BglII and EcoRI for directional ligation into pMON 530 for subsequent transformation of tobacco plants.

B. Preparation of Transgenic Plants

Transgenic plants were then regenerated, essentially as follows. Tobacco leaf tissue was separately transformed with the use of an *agrobacterium* containing the recombinant plasmids prepared above for each of the necessary proteins to create a secretory immunoglobulin. Regenerated plants were screened for the production of RNA transcript encoding the J chain by reverse transcriptase polymerase chain reaction and for the production of SC by protein immunoblot analysis. Positive transformants were self-fertilized to generate homozygous progeny.

C. Analysis of Expressed Proteins in Transgenic Plants and Crossed Progeny

For analyzing the proteins expressed in the transgenic plants produced in Section B above and for those expressed in crossed plant progeny, protein immunoblot analysis of plant extracts was conducted under both nonreducing and reducing conditions. For both types of analyses, leaf segments were homogenized in Tris-buffered saline (TBS) (150 mM NaCl and 20 mM Tris-HCl (pH 8)) with leupeptin (10 μg/ml) (Calbiochem, San Diego, Calif.).

For nonreducing conditions, the extracts were boiled for 3 minutes in 75 MM Tris-HCl (pH 6.8) and 2% SDS. SDS-polyacrylamide gel electrophoresis (PAGE) in 4 or 10% acrylamide was then performed. The gels were blotted onto nitrocellulose. The blots were incubated for 2 hours in TBS with 0.05% Tween 20 (Merck Ltd., Leicester, UK) and 1% nonfat dry milk, followed by the appropriate antiserum, and were incubated for 2 hours at 37° C. Antibody binding was detected by incubation with nitroblue tetrazolium (300 mg/ml) and 5-bromo-4-chloro-3-indolyl phosphate (150 mg/ml). Detection under nonreducing conditions was carried out with antisera to the mouse K light chain or to rabbit SC.

Protein immunoblot of plant extracts prepared under reducing conditions was similarly conducted. Samples were prepared as above, but with the addition of 5% β-mercaptoethanol SDS-PAGE in 10% acrylamide was performed and the gels were blotted as before. Detection was with antisera to the mouse γ1 heavy chain, the mouse K light chain, or rabbit SC, followed by the appropriate second-layer alkaline phosphatase-conjugated antibody.

Protein immunoblot analysis of the IGA-G plant extract with antiserum to the κ light chain under nonreducing conditions showed a band of about 210 kD, which is consistent with the presence of the extra constant region domains in the IGA-G antibody construct as compared with the original IgG1 antibody. A number of smaller proteolytic fragments were also detected, which is consistent with previous findings (Ma, Id.).

The following samples were tested under reducing conditions in one such assay: (1) Guy's 13 mAb prepared in hybridoma cell culture supernatant; (2) nontransformed wild-type plant; (3) transgenic plant expressing modified heavy and light chain genes of Guy's 13; (4) trans genic plant expressing modified heavy and light chain genes of Guy's 13 and the J chain; (5) transgenic plant expressing modified heavy and light chain genes of Guy's 13, the J chain, and SC; (6) transgenic plant expressing SC; and (7) transgenic plant expressing the J chain (data not shown).

The plants that expressed the J chain were crossed with those expressing IgA-G and immunoblot analysis of plant extracts was performed. The progeny showed a second major Ig band at about 400 kD, approximately twice the relative molecular mass of the IgA-G molecule (not shown), which suggested that a dimeric antibody (dIgA-G) had been assembled. Mature plants that expressed dIgA-G were crossed with a homozygous plant that expressed SC. The progeny plants (SIgA-G) included those that produced a higher molecular mass band of about 470 kD in protein immunoblot analysis under nonreducing conditions; such a molecular size is consistent with that expected for a secretory Ig. Detection with antiserum to SC confirmed that this high molecular mass protein contained SC. The plant extracts also contained the 400 kD band (dIgA-G) and the 210 kD band (IgA-G), but these were detected only by antiserum to the ic light chain and not by antiserum to SC. In the transgenic plant that secreted SC alone, no high molecular mass proteins were detected in protein immunoblotting under nonreducing conditions, and hence there was no evidence that SC assembled with endogenous plant proteins or formed multimers.

Further protein immunoblot analysis under reducing conditions demonstrated that extracts from the plants that expressed antibodies (IgA-G, dIgA-G, and SIgA-G), but not those that expressed the J chain or SC, contained identical antibody heavy and light chains (not shown). Only the SC and SIgA-G plants expressed proteins that were recognized by antiserum to SC (not shown). The dissociation of SC from Ig heavy chains only under reducing conditions suggests that the SC chain was at least partially covalently linked in the assembled SIgA-G molecule. The molecular mass of the major SC band under reducing conditions is about 50 kD, which is lower than expected (66.5 kD). This is probably a result of proteolysis, which may occur in the intact plant or during sample preparation. Sc bound to dimeric IgA is often found proteolyzed to smaller but biologically active forms in vivo (Ahnen, et al., *J. Clin. Invest.* 77: 1841 (1986)). However, in the protein immunoblot analysis under nonreducing conditions, the molecular mass difference between dIgA-G and SIgA-G was about 70 kD, as expected. No cross-reacting proteins were detected in extracts from the wild-type control plant.

D. Generation of Transgenic Progeny for Antibody Assembly

In mammals, the assembly of SC with antibody requires the presence of the J chain (Brandtzaeg and Prydz, *Nature* 311: 71 (1984)); this aspect was also investigated in the case of expression in plants. Thus, plants expressing monomeric IgA-G were crossed with SC-expressing plants.

In an effort to confirm the coexpression of IgA-G with SC, protein immunoblotting of transgenic plant extracts was performed under nonreducing and reducing conditions. Samples were prepared as described in section B. 1. In nonreducing conditions, protein immunoblotting was performed on 4% SDS-PAGE and detected with goat antiserum to the κ light chain, followed by alkaline phosphatase-labeled rabbit antiserum to goat IgG. In reducing conditions, protein immunoblotting was performed on 10% SDS-PAGE and detected with sheep antiserum to SC, followed by alkaline phosphatase-labeled donkey antiserum to sheep IgG.

In the progeny, only the 210 kD monomeric form of the antibody was recognized by antiserum to the K light chain; antiserum to SC recognized free SC but did not recognize proteins associated with 1 g (results not shown). These results were confirmed in all 10 plants examined, whereas all 10 plants that coexpressed the J chain, the antibody chains, and SC assembled the 470 kD SIgA-G molecule. This finding confirms the requirement of the J chain for SC association with Ig and suggests that the nature of the association in plants is similar to that in mammals.

Functional antibody studies were carried out with the five plant constructs by enzyme-linked immunosorbent assay (ELISA) (FIG. 4). The procedure was carried out essentially as follows.

Microtiter plates were coated either with purified SA I/II (2 µ/ml) in TBS or with log phase growth *S. mutans* (NCTC 10499) in bicarbonate buffer (pH 9.8). Blocking was done with 5% nonfat dry milk in TBS at room temperature for 2 hours. Plant leaves were homogenized in TBS with leupeptin (10 µg/ml). The supernatants were added in serial twofold dilutions to the microtiter plate; incubation was at room temperature for 2 hours.

After washing with TBS with 0.05% Tween 20, bound Ig chains were detected either with a goat antibody to mouse light chain conjugated with horseradish peroxidase (HRP) (Nordic Pharmaceuticals, UK) or with a sheep antiserum to SC, followed by donkey antibody to sheep Ig, conjugated with alkaline phosphatase. Conjugated antibodies were applied for 2 hours at room temperature. HRP-conjugated antibodies were detected with 2,2'-azino-di-(3-ethyl-benzthiazoline sulfonate) (Boehringer Mannheim, Indianapolis, Ind.); alkaline phosphatase-conjugated antibodies were detected with disodium p-nitrophenylphosphate (Sigama, UK). The concentrations of the antibody solutions were initially determined by ELISA in comparison with a mouse IgA mAb (TEPC-21) used at known concentrations (Ma, et al., Id. (1994)). In the antigen-binding ELISAs, the starting concentration of each antibody solution was 5 µg/ml.

The results illustrated in FIGS. 4A–C may be described as follows. FIGS. 4A–C illustrate the demonstration of functional antibody expression in transgenic *N. tabacum* as measured by absorbance at 405 nm (A405). In all three figures, Guy's 13 hybridoma cell culture supernatant (IgG) was used as a positive control. The initial concentration of each antibody solution was 5 µg/ml. Dilution numbers represent serial double dilutions. Illustrated results are expressed as the mean±SD of three separate triplicate experiments. In all three figures, the solid squares (■) represent SIgA-G; solid circles (●) represent dIgA-G; solid triangles (▲) represent IGA-G; open squares (□) represent SC; open circles (○) represent J chain; open triangles (Δ) represent a nontransformed, wild-type plant (WT); and inverted, closed triangles (▼) represent Guy's 13. Dilution is plotted on the horizontal axis, while absorbance is plotted on the vertical axis.

All plants expressing antibody light and heavy chains assembled functional antibodies that specifically recognized SA I/II (FIG. 4A). The levels of binding and titration curves were similar to those of the native mouse hybridoma cell supernatant. No SA I/II binding was detected with wild-type plants or with plants expressing the J chain or SC. The binding of antibody to immobilized purified SA or native antigen on the bacterial cell surface was also detected with antiserum to SC (FIGS. 4B and 4C). In these assays, only the SIGA-G plant antibody binding was detected and not the functional antibodies in the IgA-G or dIgA-G plants. These results conform that SC was assembled with antibody in the SIgA-G plant but did not interfere with antigen recognition or binding.

The assembly of functional Ig molecules in plants is very efficient (Hiatt, et al., Nature 342: 76 (1989)). Initial estimates for the plants expressing SIgA-G suggest that approximately 50% of the SC is associated with dimeric IgA-G in the plant extracts (data not shown). Preliminary results indicate that the SIgA-G yield from fully expanded leaf lamina is 200 to 500 µg per gram or fresh weight material. This yield is considerably greater than that determined for monomeric IgA-G and is consistent with the suggestion that SIgA-G might be more resistant to proteolysis.

Here, the fidelity of plant assembly has been extended to include dimerization of monomeric antibody by the J chain. Coexpression of recombinant IgA with the J chain through the use of baculovirus in insect cells has been reported (Carayannopoulos, et al., PNAS USA 91: 8,48 (1994)); however, only a small proportion of the expressed antibody was dimerized, and most remained in a monomeric form. By contrast, in plants the dimeric antibody population represents a major proportion (about 57%) of the total antibody (data not shown). This is also the first report of an assembled secretory antibody (SIgA-G) that binds as well to the corresponding antigen as does the parent mAb and constitutes a major proportion of the total assembled antibody (about 45%; data not shown). Protein immunoblot analysis potentially underestimates the total extent of assembly of SIgA-G because it only detects antibody that is covalently linked to SC, whereas SIgA can occur in vivo as a mixture of covalently and noncovalently linked molecules (Schneiderman, et al., PNAS USA 86: 7561 (1975)).

The four transgenes for SIgA-G were introduced into plants with the identical pMON530 expression cassette, native leader sequences, and a promoter sequence derived from the $^{35}$S transcript of the cauliflower mosaic virus, which directs expression of transgenes in a variety of cell types of most plant organs (Benfey and Chua, Science 250: 959 (1990); Barnes, PNAS USA 37: 9183 (1990)). The use of the same promoter for all four transgenes maximized the likelihood of coincidental expression in a common plant cell.

E. Microscopic Observation

Plant specimens were prepared for microscopic observation essentially as follows. Leaf blades were cut into segments (2×10 mm) and fixed in 3% (w/v) paraformaldehyde, 0.5% (w/v) glutaraldehyde, and 5% (w/v) sucrose in 100 mM sodium phosphate (pH 7.4). After dehydration through a graded ethanol series, leaf segments were infiltrated with xylene, embedded in paraffin, cut into 5-mm sections, and mounted on glass slides for immunochemical staining. The leaf sections were incubated with primary antibodies (affinity-purified rabbit antibody to mouse a chain, which reacts with the A-G hybrid heavy chain, or sheep antibody to rabbit SC) and then with secondary antibodies (goat antibody to rabbit Ig or rabbit antibody to sheep Ig, both labeled with 10-nm gold). The immunogold signal was intensified by silver enhancement.

Microscopic observation of SIgA-G plants revealed that many cell types of the leaves contained SIgA-G components. The predominant accumulation of these proteins was in the highly vacuolated cells of the mesophyll, particularly in bundle sheath cells; the cytoplasmic band surrounding the large central vacuole was strongly labeled. At the level of light microscopy, it is not possible to distinguish between antigens that are cytoplasmic and those that are contained in the luminal apoplastic space between the cell wall and the plasmalemma, but it is evident that the recombinant antibody components do not penetrate the cell wall.

F. Discussion

Restriction of the largest SIgA-G components, SC and heavy chain, within the confines of the protoplastic or apoplastic compartments of individual cells would constrain the assembly of sig to single cells. In contrast, two cell types are required to produce SIgA in mammals. In the plant system, a mature SC devoid of signals for membrane integration, transcytosis, or subsequent proteolysis can thus be assembled with a hybrid Ig containing a domains within the secretory pathway of the cell. Assembly of monomeric antibody is known to require the targeting of both light and heavy chains to the endoplasmic reticulum (ER) (Hein, et al., Biotechnol. Pros. 7: 455 (1991)). Thus SIgA-G assembly might occur at two sites: either in the ER, after dimerization with the J chain, or in the extracellular apoplasm, where the secreted antibody is accumulated.

The inherent functions of IgG-constant regions, that is, protein A binding, complement fixation, and the ability to bind to specific cell surface receptors (Fc receptors), may be retained in a dimeric Ig that is capable of binding SC. These additional properties of SIgA-G may enhance the function of the complex in passive immunotherapy, although under some circumstances these biological properties might be undesirable. In principle it should not be difficult to produce a SIgA-G antibody that lacks the Cα2 domain in these cases.

The development of plants capable of generating functional SIgA may have significant implications for passive immunotherapy. Previously, SIgA has been generated only with difficulty, by in vitro conjugation of SC with dimeric IgA (Mach, Nature 228: 1278 (1970)) or by the insertion of subcutaneous "backpack" tumors of hybridoma cells secreting monoclonal IgA (Winner, et al., Infect. Immun. 59: 977 (1991)). The plants express SIGA in large amounts, and the production can be scaled up to agricultural proportions. This method offers an economic means of producing large quantities of mAbs that could be applied to mucosal surfaces to prevent infection, as has been demonstrated in passive immunotherapy against streptococci (Lehner, et al., Infect. Immun. 50: 796 (1985); Bessen and Fischetti, J. Exp. Med. 167: 1945 (1988); Ma, et al., Infect. Immun. 58: 3407 (1990)). Multivalent antibodies might be more protective than IgG at mucosal surfaces (Kilian, et al., Microbiol. Rev.

52: 296 (1988)), and SC may also have postsecretory functions in stabilizing the polymeric antibody against proteolysis (Underdown and Dorrington, *J. Immunol.* 112: 949 (1974); Mestecky and McGhee, *Adv. Immunol.* 40: 153 (1987)). The principle of sexual crossing of transgenic plants to accumulate recombinant subunits can readily be applied to the assembly of a variety of Ig as well as other complex protein molecules.

The foregoing is intended as illustrative of the present invention but not limiting. Numerous variations and modifications can be effected without departing from the true spirit and scope of the invention.

We claim:

1. A plant comprising:
    (a) plant cells containing nucleotide sequences encoding a biologically functional multimeric protein comprising at least two different polypeptides not naturally produced by plants, wherein each nucleotide sequence encoding a polypeptide of the multimeric protein encodes a leader sequence forming a secretion signal that is cleaved from said polypeptide following proteolytic processing; and
    (b) biologically functional multimeric protein encoded by said nucleotide sequences and resulting from assembly of said at least two different polypeptides wherein the multimeric protein is an abzyme.

2. A plant comprising:
    (a) plant cells containing nucleotide sequences encoding a biologically functional multimeric protein comprising at least two different polypeptides not naturally produced by plants, wherein each nucleotide sequence encoding a polypeptide of the multimeric protein encodes a leader sequence forming a secretion signal that is cleaved from said polypeptide following proteolytic processing; and
    (b) biologically functional multimeric protein encoded by said nucleotide sequences and resulting from assembly of said at least two different polypeptides wherein the multimeric protein comprises an immunoglobulin.

3. The plant of claim 2 wherein the immunoglobulin comprises a Fab.

4. The plant of claim 2 wherein the immunoglobulin comprises a Fab'.

5. The plant of claim 2 wherein the immunoglobulin comprises a F(ab')2.

6. The plant of claim 2 wherein the immunoglobulin comprises a Fv.

7. The plant of claim 2 wherein the Immunoglobulin comprises an antibody.

8. The plant of claim 2 wherein the immunoglobulin contains a paratope.

9. A plant comprising:
(a) plant cells containing nucleotide sequences encoding a biologically functional multimeric protein comprising at least two different polypeptides not naturally produced by plants, wherein each nucleotide sequence encoding a polypeptide of the multimeric protein encodes a leader sequence forming a secretion signal that is cleaved from said polypeptide following proteolytic processing; and
(b) biologically functional multimeric protein encoded by said nucleotide sequences and resulting from assembly of said at least two different polypeptides wherein the multimeric protein comprises a glycosylated immunoglobulin molecule free of sialic acid residues.

10. A plant cell containing nucleotide sequences encoding an antigen-specific immunoglobulin, said nucleotide sequences encoding an immunoglobulin heavy and light chain polypeptide wherein each polypeptide contains a leader sequence that forms a secretion signal; and immunoglobulin encoded by said nucleotide sequences, wherein each leader sequence is cleaved from said immunoglobulin heavy chain and light chain polypeptide following proteolytic processing resulting in assembly of said antigen-specific immunoglobulin.

11. The plant cell of claim 10 wherein the immunoglobulin is an abzyme.

12. The plant cell of claim 10 wherein the immunoglobulin comprises a Fab.

13. The plant cell of claim 10 wherein the immunoglobulin comprises a Fab'.

14. The plant cell of claim 10 wherein the immunoglobulin comprises a F(ab')2.

15. The plant cell of claim 10 wherein the immunoglobulin comprises an Fv.

16. The plant cell of claim 10 wherein the immunoglobulin comprises an antibody.

17. The plant cell of claim 10 wherein the immunoglobulin contains a paratope.

18. The plant cell of claim 10 wherein the immunoglobulin is glycosylated, said glycosylation being free of sialic acid residues.

19. The plant cell of claim 10 wherein the cell is a dicotyledonous plant cell.

20. The plant cell of claim 10 wherein the cell is a monocotyledonous plant cell.

21. The plant cell of claim 10 obtained from an algal plant.

22. The plant cell of claim 10 wherein the immunoglobulin heavy chain is selected from the group consisting of IgA heavy chain, IgD heavy chain, IgE heavy chain, IgG heavy chain, and IgM heavy chain.

23. The plant cell of claim 10, wherein said heavy chain is an IgA heavy chain.

24. The plant cell of claim 10, wherein said heavy chain is an IgM heavy chain.

25. The plant cell of claim 10, wherein said heavy chain is an IgG heavy chain.

26. The plant cell of claim 10, wherein said leader sequence is non-native to the plant cell.

27. The plant cell of claim 26, wherein said non-native leader sequence is an immunoglobulin leader sequence.

28. The plant cell of claim 26, wherein said non-native leader sequence is a yeast leader sequence.

29. The plant cell of claim 10, wherein said leader sequence is a plant leader sequence.

30. The plant cell of claim 10 wherein said cell is from a tobacco plant.

31. A plant comprising the plant cell of claim 10.

* * * * *